US008946187B2

(12) United States Patent
Croce et al.

(10) Patent No.: US 8,946,187 B2
(45) Date of Patent: Feb. 3, 2015

(54) MATERIALS AND METHODS RELATED TO MICRORNA-21, MISMATCH REPAIR, AND COLORECTAL CANCER

(75) Inventors: Carlo M. Croce, Columbus, OH (US); Nicola Valeri, Columbus, OH (US)

(73) Assignee: The Ohio State University, Columbus, OH (US)

( * ) Notice: Subject to any disclaimer, the term of this patent is extended or adjusted under 35 U.S.C. 154(b) by 0 days.

(21) Appl. No.: 13/884,668

(22) PCT Filed: Nov. 11, 2011

(86) PCT No.: PCT/US2011/060349
§ 371 (c)(1),
(2), (4) Date: Jun. 19, 2013

(87) PCT Pub. No.: WO2012/065049
PCT Pub. Date: May 18, 2012

(65) Prior Publication Data
US 2014/0045918 A1    Feb. 13, 2014

Related U.S. Application Data

(60) Provisional application No. 61/413,180, filed on Nov. 12, 2010.

(51) Int. Cl.
A61K 48/00 (2006.01)
C12N 15/113 (2010.01)
A61K 31/513 (2006.01)
A61K 31/713 (2006.01)
G01N 33/574 (2006.01)

(52) U.S. Cl.
CPC ............ *C12N 15/113* (2013.01); *A61K 31/513* (2013.01); *A61K 31/713* (2013.01); *G01N 33/57419* (2013.01); *G01N 2800/52* (2013.01); *G01N 2800/56* (2013.01)
USPC ........................................... 514/44; 536/24.5

(58) Field of Classification Search
None
See application file for complete search history.

(56) References Cited

U.S. PATENT DOCUMENTS

| | | |
|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,455,995 B2 | 11/2008 | Tanner et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |

(Continued)

FOREIGN PATENT DOCUMENTS

| AU | 2007/243475 B2 | 5/2013 |
|---|---|---|
| CA | 2533701 A1 | 2/2005 |

(Continued)

OTHER PUBLICATIONS

Australian Examination Report No. 1, Application No. 2007205257 dated Oct. 24, 2011.
Australian Examination Report No. 1, Application No. 2007314212 dated Aug. 28, 2012.
Australian Examination Report No. 2, Application No. 2008248319 dated Apr. 9, 2013.
Australian Examination Report No. 1, Application No. 2007227423 dated Apr. 13, 2012.
Australian Examination Report No. 1, Application No. 2007346101 dated Jun. 21, 2012.

(Continued)

*Primary Examiner* — Kimberly Chong
(74) *Attorney, Agent, or Firm* — MacMillan, Sobanski & Todd, LLC

(57) ABSTRACT

The present invention discloses the discovery that miR-21 targets and down-regulates the core mismatch repair (MMR) recognition protein complex hMSH2 and hMSH6. Anti-sense miR-21 is therefore proven as therapeutic herein. Therefore, compositions, kits, therapies and other methods, including methods of treatment/amelioration of symptoms, are disclosed in the present invention.

10 Claims, 14 Drawing Sheets
(12 of 14 Drawing Sheet(s) Filed in Color)

(56) References Cited

U.S. PATENT DOCUMENTS

| | | |
|---|---|---|
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 7,811,759 B2 | 10/2010 | Han |
| 7,888,010 B2 | 2/2011 | Brown et al. |
| 7,919,245 B2 | 4/2011 | Brown et al. |
| 8,084,199 B2 | 12/2011 | Croce et al. |
| 8,361,710 B2 | 1/2013 | Croce et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2003/0143646 A1 | 7/2003 | Laskey et al. |
| 2003/0206958 A1 | 11/2003 | Cattaneo et al. |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0013247 A1 | 1/2005 | Sipola et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0182005 A1* | 8/2005 | Tuschl et al. .................. 514/44 |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0116321 A1 | 6/2006 | Robbins et al. |
| 2006/0121085 A1 | 6/2006 | Warren et al. |
| 2006/0127895 A1 | 6/2006 | Sabapathy |
| 2006/0134639 A1 | 6/2006 | Huffel et al. |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0199233 A1 | 9/2006 | Dahlberg et al. |
| 2006/0247448 A1 | 11/2006 | Boivin et al. |
| 2006/0292616 A1 | 12/2006 | Neely et al. |
| 2007/0015841 A1 | 1/2007 | Tawa et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0092882 A1 | 4/2007 | Wang et al. |
| 2007/0099196 A1 | 5/2007 | Kauppinen et al. |
| 2007/0123482 A1 | 5/2007 | Stoffel et al. |
| 2007/0161004 A1 | 7/2007 | Brown et al. |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023149 A1 | 1/2009 | Knudsen et al. |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1 | 5/2009 | Bader et al. |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0220589 A1 | 9/2009 | Trieu et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0239818 A1 | 9/2009 | Cheng |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004320 A1 | 1/2010 | Elmen et al. |
| 2010/0004322 A1 | 1/2010 | Croce |
| 2010/0021734 A1 | 1/2010 | Uemoto et al. |
| 2010/0048681 A1 | 2/2010 | Croce |
| 2010/0099200 A1 | 4/2010 | Nazabal et al. |
| 2010/0104662 A1 | 4/2010 | Oren et al. |
| 2010/0120898 A1 | 5/2010 | Croce et al. |
| 2010/0137410 A1 | 6/2010 | Croce |
| 2010/0144850 A1 | 6/2010 | Croce |
| 2010/0151480 A1 | 6/2010 | Taylor et al. |
| 2010/0173319 A1 | 7/2010 | Croce et al. |
| 2010/0179213 A1 | 7/2010 | Patrawala et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0196426 A1 | 8/2010 | Skog et al. |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0285471 A1 | 11/2010 | Croce et al. |
| 2010/0298410 A1 | 11/2010 | Obad et al. |
| 2010/0305188 A1 | 12/2010 | Nakano et al. |
| 2010/0317610 A1 | 12/2010 | Croce |
| 2011/0003704 A1 | 1/2011 | Skog et al. |
| 2011/0021601 A1 | 1/2011 | Park et al. |
| 2011/0054006 A1 | 3/2011 | Slack et al. |
| 2011/0054009 A1 | 3/2011 | Croce et al. |

(56) References Cited

U.S. PATENT DOCUMENTS

| | | | |
|---|---|---|---|
| 2011/0107440 A1 | 5/2011 | Pivaresi et al. |
| 2011/0136124 A1 | 6/2011 | Roa et al. |
| 2011/0166200 A1 | 7/2011 | Zhang |
| 2011/0251150 A2 | 10/2011 | Bennett et al. |
| 2011/0275534 A1 | 11/2011 | Cohn et al. |

FOREIGN PATENT DOCUMENTS

| | | |
|---|---|---|
| CA | 2587189 A1 | 12/2006 |
| CN | 1719973 A | 1/2006 |
| CN | 101215560 B | 9/2010 |
| CN | 1282422 A | 1/2011 |
| EP | 1662259 A1 | 5/2006 |
| EP | 1676914 A1 | 7/2006 |
| EP | 1795203 A2 | 6/2007 |
| EP | 2354246 A1 | 8/2011 |
| EP | 2487240 A1 | 8/2012 |
| EP | 2481806 A3 | 10/2012 |
| FR | 2877350 A1 | 5/2006 |
| JP | 2005/503827 A | 2/2005 |
| JP | 2005/517452 A | 6/2005 |
| JP | 2005/192484 A | 7/2005 |
| JP | 2005/296014 A | 10/2005 |
| JP | 2008/083201 A | 4/2008 |
| JP | 5395439 B2 | 1/2014 |
| WO | 90/15156 A1 | 12/1990 |
| WO | 91/00364 A1 | 1/1991 |
| WO | 91/07424 A1 | 5/1991 |
| WO | 93/12136 A1 | 6/1993 |
| WO | 94/10343 A1 | 5/1994 |
| WO | 94/24308 A1 | 10/1994 |
| WO | 94/26930 A1 | 11/1994 |
| WO | 96/13514 A1 | 5/1996 |
| WO | 96/35124 A1 | 11/1996 |
| WO | 97/29119 A1 | 8/1997 |
| WO | 98/09510 A1 | 3/1998 |
| WO | 00/03685 A2 | 1/2000 |
| WO | 00/50565 A2 | 8/2000 |
| WO | 00/55169 A1 | 9/2000 |
| WO | 00/76524 A1 | 12/2000 |
| WO | 01/07914 A1 | 2/2001 |
| WO | 01/44466 A1 | 6/2001 |
| WO | 01/68666 A1 | 9/2001 |
| WO | 01/77343 A1 | 10/2001 |
| WO | 01/87958 A2 | 11/2001 |
| WO | 02/064171 A1 | 8/2002 |
| WO | 02/064172 A2 | 8/2002 |
| WO | 03/029459 A2 | 4/2003 |
| WO | 03/078662 A1 | 9/2003 |
| WO | 03/092370 A1 | 11/2003 |
| WO | 2004/033659 A2 | 4/2004 |
| WO | 2004/043387 A2 | 5/2004 |
| WO | 2004/079013 A1 | 9/2004 |
| WO | 2004/098377 A2 | 11/2004 |
| WO | 2005/013901 A3 | 2/2005 |
| WO | 2005/017711 A2 | 2/2005 |
| WO | 2005/020795 A2 | 3/2005 |
| WO | 2005/060661 A2 | 7/2005 |
| WO | 2005/078139 A2 | 8/2005 |
| WO | 2005/079397 A2 | 9/2005 |
| WO | 2005/080601 A2 | 9/2005 |
| WO | 2005/094263 A2 | 10/2005 |
| WO | 2005/103298 A2 | 11/2005 |
| WO | 2005/111211 A2 | 11/2005 |
| WO | 2005/118806 A2 | 12/2005 |
| WO | 2006/105486 A2 | 10/2006 |
| WO | 2006/108718 A1 | 10/2006 |
| WO | 2006/119266 A2 | 11/2006 |
| WO | 2006/119365 A3 | 11/2006 |
| WO | 2006/133022 A2 | 12/2006 |
| WO | 2006/137941 A2 | 12/2006 |
| WO | 2007/016548 A2 | 2/2007 |
| WO | 2007/033023 A2 | 3/2007 |
| WO | 2007/044413 A2 | 4/2007 |
| WO | 2007/081680 A2 | 7/2007 |
| WO | 2007/081720 A2 | 7/2007 |
| WO | 2007/081740 A2 | 7/2007 |
| WO | 2007/084486 A2 | 7/2007 |
| WO | 2007/109236 A2 | 9/2007 |
| WO | 2007/112097 A2 | 10/2007 |
| WO | 2007/112754 A2 | 10/2007 |
| WO | 2007/115134 A2 | 10/2007 |
| WO | 2007/127190 A2 | 11/2007 |
| WO | 2008/008430 A2 | 1/2008 |
| WO | 2008/029295 A2 | 3/2008 |
| WO | 2008/036168 A2 | 3/2008 |
| WO | 2008/036776 A2 | 3/2008 |
| WO | 2008/054828 A2 | 5/2008 |
| WO | 2008/064519 A1 | 6/2008 |
| WO | 2008/070082 A2 | 6/2008 |
| WO | 2008/073915 A2 | 6/2008 |
| WO | 2008/073920 A2 | 6/2008 |
| WO | 2008/094545 A2 | 8/2008 |
| WO | 2008/097277 A2 | 8/2008 |
| WO | 2008/136971 A1 | 11/2008 |
| WO | 2008/153987 A2 | 12/2008 |
| WO | 2008/157319 A1 | 12/2008 |
| WO | 2009/018303 A2 | 2/2009 |
| WO | 2009/020905 A2 | 2/2009 |
| WO | 2009/026487 A1 | 2/2009 |
| WO | 2009/033140 A1 | 3/2009 |
| WO | 2009/036236 A1 | 3/2009 |
| WO | 2009/049129 A1 | 4/2009 |
| WO | 2009/055773 A2 | 4/2009 |
| WO | 2009/064590 A2 | 5/2009 |
| WO | 2009/070653 A1 | 6/2009 |
| WO | 2009/100029 A1 | 8/2009 |
| WO | 2009/108853 A1 | 9/2009 |
| WO | 2009/108856 A2 | 9/2009 |
| WO | 2009/108860 A2 | 9/2009 |
| WO | 2009/108866 A2 | 9/2009 |
| WO | 2009/152300 A1 | 12/2009 |
| WO | 2010/019694 A1 | 2/2010 |
| WO | 2010/059779 A1 | 5/2010 |
| WO | 2010/065156 A1 | 6/2010 |
| WO | 2010/099161 A1 | 9/2010 |
| WO | 2011/057304 A2 | 5/2011 |
| WO | 2011/059776 A2 | 5/2011 |
| WO | 2011/063382 A1 | 5/2011 |
| WO | 2011/119553 A2 | 9/2011 |
| WO | 2011/163116 A3 | 12/2011 |
| WO | 2012/019053 A2 | 2/2012 |
| WO | 2012/065049 A2 | 5/2012 |
| WO | 2012/097047 A1 | 7/2012 |
| WO | 2012/122239 A1 | 9/2012 |

OTHER PUBLICATIONS

Australian Examination Report No. 3, Application No. 2007205257 dated Jan. 9, 2013.
Australian Examination Report No. 1, Application No. 2008266014 dated Jul. 6, 2012.
Australian Examination Report No. 2, Application No. 2008282318 dated Nov. 19, 2013.
Australian Examination Report No. 1, Application No. 2008262252 dated Feb. 15, 2013.
Australian Examination Report No. 1, Application No. 2008248319 dated Jul. 12, 2012.
Australian Examination Report No. 2, Application No. 2007205163 dated Nov. 15, 2012.
Australian Examination Report No. 1, Application No. 2007205234 dated Jun. 17, 2011.
Australian Examination Report No. 2, Application No. 2006291165 dated Feb. 13, 2012.
Australian Examination Report No. 2, Application No. 2007205257 dated Jul. 16, 2012.
Australian Examination Report No. 3, Application No. 2007205163 dated Mar. 28, 2013.
Australian Examination Report No. 2, Application No. 2009281969 dated Jun. 30, 2014.
Australian Examination Report No. 2, Application No. 2007346101 dated May 24, 2013.

(56) References Cited

OTHER PUBLICATIONS

Australian Examination Report No. 1, Application No. 2008310704 dated Jun. 24, 2013.
Australian Examination Report No. 2, Application No. 2008288806 dated Mar. 25, 2014.
Australian Examination Report No. 1, Application No. 2008282318 dated Feb. 7, 2013.
Australian Examination Report No. 2, Application No. 2007227423 dated Mar. 1, 2013.
Australian Examination Report No. 2, Application No. 2007314212 dated Apr. 29, 2013.
Australian Examination Resport No. 1, Application No. 2008316577 dated Feb. 11, 2013.
Australian Examination Report No. 1, Application No. 2008283997 dated Aug. 20, 2007.
Australian Examination Report No. 1, Application No. 2007242475 dated Mar. 30, 2012.
Australian Examination Report No. 4, Application No. 2006291165 dated Jan. 7, 2013.
Australian Examination Report No. 1, Application No. 2009219197 dated Sep. 19, 2013.
Australian Examination Report No. 3, Application No. 2006291165 dated Sep. 12, 2012.
Australian Examination Report No. 2, Application No. 2007272947 dated May 21, 2012.
Australian Examination Report No. 1, Application No. 2009281969 dated Jan. 16, 2014.
Canadian Office Action, Application No. 2,617,581 dated Apr. 2, 2012.
Canadian Office Action, Application No. 2,657,030 dated Jan. 13, 2014.
Canadian Office Action, Application No. 2,646,051 dated Feb. 25, 2011.
Canadian Office Action, Application No. 2,621,441 dated Feb. 1, 2011.
Canadian Office Action, Application No. 2,617,581 dated Feb. 1, 2011.
Canadian Office Action, Application No. 2,621,441 dated Apr. 8, 2013.
Canadian Office Action, Application No. 2,667,617 dated Jan. 2, 2014.
Canadian Office Action, Application No. 2,635,616 dated Feb. 27, 2012.
Canadian Office Action, Application No. 2,685,840 dated Jun. 5, 2014.
Chinese 1st Office Action, Application No. 200880119206 dated May 3, 2012.
Chinese 1st Office Action, Application No. 201080059339.9 dated Aug. 26, 2013.
Chinese 1st Office Action, Application No. 201210312507.1 dated Jul. 29, 2013.
Chinese 1st Office Action, Application No. 200980135456.6 dated Nov. 13, 2012.
Chinese 1st Office Action, Application No. 200980155340.9 dated Jan. 21, 2013.
Chinese 1st Office Action, Application No. 200980126520.4 dated Dec. 4, 2012.
Chinese 1st Office Action, Application No. 200980113258 dated Mar. 13, 2013.
Chinese 1st Office Action, Application No. 200780040146.7 dated May 25, 2011.
Chinese 1st Office Action, Application No. 200880025276.8 dated Nov. 23, 2011.
Chinese 1st Office Action, Application No. 200780005821.2 dated Jan. 26, 2011.
Chinese 1st Office Action, Application No. 200780005791.5 dated Mar. 24, 2011.
Chinese 1st Office Action, Application No. 200880108689.2 dated Feb. 13, 2012.
Chinese 1st Office Action, Application No. 201110319534.7 dated Jun. 8, 2013.
Chinese 1st Office Action, Application No. 200880108625.2 dated Feb. 13, 2012.
Chinese 1st Office Action, Application No. 200980111708.1 dated Aug. 27, 2012.
Chinese 1st Office Action, Application No. 200880022612.3 dated Apr. 24, 2012.
Chinese 1st Office Action, Application No. 200880103023.8 dated Oct. 9, 2012.
Chinese 1st Office Action, Application No. 200780018496.3 dated Mar. 22, 2011.
Chinese 1st Office Action, Application No. 200980112966.1 dated Sep. 20, 2012.
Chinese 1st Office Action, Application No. 200980114564.5 dated Dec. 19, 2013.
Chinese 1st Office Action, Application No. 200780023093.8 dated Dec. 27, 2010.
Chinese 1st Office Action, Application No. 201310230787.6 dated May 19, 2014.
Chinese 1st Office Action, Application No. 200880116343.7 dated Jan. 31, 2012.
Chinese 1st Office Action, Application No. 200880112581.0 dated Aug. 13, 2012.
Chinese 1st Office Action, Application No. 200780033066.9 dated Sep. 18, 2011.
Chinese 1st Office Action, Application No. 201210380806.9 dated Nov. 5, 2013.
Chinese 1st Office Action, Application No. 200880112585.9 dated May 24, 2012.
Chinese 2nd Office Action, Application No. 200980135456.6 dated Aug. 1, 2013.
Chinese 2nd Office Action, Application No. 200680036598.3 dated Feb. 24, 2011.
Chinese 2nd Office Action, Application No. 201210380806.9 dated Jun. 23, 2014.
Chinese 2nd Office Action, Application No. 200880108689.2 dated Sep. 12, 2012.
Chinese 2nd Office Action, Application No. 201080059339.9 dated Apr. 9, 2014.
Chinese 2nd Office Action, Application No. 200880116343.7 dated Oct. 22, 2012.
Chinese 2nd Office Action, Application No. 200880025276.8 dated Aug. 1, 2012.
Chinese 2nd Office Action, Application No. 200880103023.8 dated Jun. 20, 2013.
Chinese 2nd Office Action, Application No. 200880022612.3 dated Oct. 29, 2012.
Chinese 2nd Office Action, Application No. 200680039776.8 dated Jun. 30, 2011.
Chinese 2nd Office Action, Application No. 200880112585.9 dated Jan. 21, 2013.
Chinese 2nd Office Action, Application No. 200780018496.3 dated Mar. 1, 2012.
Chinese 2nd Office Action, Application No. 200980111708.1 dated May 20, 2013.
Chinese 2nd Office Action, Application No. 200880112581.0 dated May 10, 2013.
Chinese 2nd Office Action, Application No. 200780040146.7 dated Dec. 31, 2011.
Chinese 2nd Office Action, Application No. 200780023093.8 dated Dec. 9, 2011.
Chinese 2nd Office Action, Application No. 200880003736.7 dated Nov. 5, 2012.
Chinese 2nd Office Action, Application No. 200780005791.5 dated May 3, 2012.
Chinese 2nd Office Action, Application No. 200980112966.1 dated May 9, 2013.
Chinese 2nd Office Action, Application No. 200980155340.9 dated Aug. 26, 2013.
Chinese 2nd Office Action, Application No. 200880119206.9 dated Feb. 1, 2013.

(56) References Cited

OTHER PUBLICATIONS

Chinese 2nd Office Action, Application No. 200780005821.2 dated Apr. 1, 2012.
Chinese 2nd Office Action, Application No. 200980126520.4 dated Aug. 14, 2013.
Chinese 2nd Office Action, Application No. 200880108625.2 dated Aug. 21, 2012.
Chinese 2nd Office Action, Application No. 200780033066.9 dated Jun. 26, 2012.
Chinese 3rd Office Action, Application No. 200780033066.9 dated Dec. 17, 2012.
Chinese 3rd Office Action, Application No. 200780005791.5 dated Dec. 5, 2012.
Chinese 3rd Office Action, Application No. 200780023093.8 dated Jul. 2, 2012.
Chinese 3rd Office Action, Application No. 200780005821.2 dated Nov. 5, 2012.
Chinese 3rd Office Action, Application No. 200880003736.7 dated Apr. 12, 2013.
Chinese 3rd Office Action, Application No. 200880022612.3 dated May 17, 2013.
Chinese 3rd Office Action, Application No. 200880116343.7 dated Apr. 8, 2013.
Chinese 3rd Office Action, Application No. 200780040146.7 dated Apr. 25, 2012.
Chinese 3rd Office Action, Application No. 200980126520.4 dated Feb. 18, 2014.
Chinese 3rd Office Action, Application No. 200980135456.6 dated Feb. 8, 2014.
Chinese 3rd Office Action, Application No. 200980112966.1 dated Dec. 4, 2013.
Chinese 3rd Office Action, Application No. 200980113258.X dated Jun. 10, 2014.
Chinese 3rd Office Action, Application No. 200880119206.9 dated Aug. 12, 2013.
Chinese 3rd Office Action, Application No. 200980111708.1 dated Nov. 4, 2013.
Chinese 3rd Office Action, Application No. 200880108689.2 dated Apr. 1, 2013.
Chinese 3rd Office Action, Application No. 200880108625.2 dated Jan. 5, 2013.
Chinese 4th Office Action, Application No. 200780040146.7 dated Nov. 23, 2012.
Chinese 4th Office Action, Application No. 200780023093.8 dated Jan. 14, 2013.
Chinese 4th Office Action, Application No. 200780005821.2 dated May 13, 2013.
Chinese 4th Office Action, Application No. 200880116343.7 dated Jul. 10, 2013.
Chinese 4th Office Action, Application No. 200880022612.3 dated Nov. 19, 2013.
Chinese 5th Office Action, Application No. 200780040146.7 dated Apr. 16, 2013.
Chinese Rejection Decision, Application No. 200880103023.8 dated Feb. 13, 2014.
Chinese Rejection Decision, Application No. 200780018496.3 dated Sep. 5, 2012.
Chinese Rejection Decision, Application No. 200780033066.9 dated Jun. 13, 2013.
European Examination Report, Application No. 07716208.9 dated Sep. 13, 2011.
European Examination Report, Application No. 06800599.0 dated Nov. 25, 2011.
European Examination Report, Application No. 11151771.0 dated Jan. 3, 2013.
European Examination Report, Application No. 08799295.4 dated Nov. 18, 2011.
European Examination Report, Application No. 11151769.4 dated Jan. 3, 2013.
European Examination Report, Application No. 08767439.6 dated Dec. 2, 2011.
European Examination Report, Application No. 07867402.5 dated Jan. 5, 2011.
European Examination Report, Application No. 11170608.1 dated May 3, 2012.
European Examination Report, Application No. 07716208.9 dated Sep. 13, 2012.
European Examination Report, Application No. 12154348.2 dated Oct. 9, 2013.
European Examination Report, Application No. 11151749.6 dated Dec. 10, 2012.
European Examination Report, Application No. 07810382.7 dated Dec. 8, 2010.
European Examination Report, Application No. 12154341.7 dated Aug. 9, 2013.
European Examination Report, Application No. 08767439.6 dated Mar. 15, 2011.
European Examination Report, Application No. 08768266.2 dated Apr. 18, 2011.
European Examination Report, Application No. 08799295.4 dated Dec. 10, 2012.
European Examination Report, Application No. 08841700.1 dated Jun. 1, 2012.
European Examination Report, Application No. 12154246.8 dated Nov. 22, 2013.
European Examination Report, Application No. 09715064.3 dated Nov. 5, 2012.
European Examination Report, Application No. 12154298.9 dated Nov. 22, 2013.
European Examination Report, Application No. 09715064.3 dated Feb. 12, 2014.
European Examination Report, Application No. 07717903.4 dated Aug. 16, 2011.
European Examination Report, Application No. 07717903.4 dated Jan. 29, 2010.
European Examination Report, Application No. 12165748.0 dated Sep. 17, 2013.
European Examination Report, Application No. 07716208.9 dated Apr. 20, 2010.
European Examination Report, Application No. 08796821.0 dated Jan. 7, 2013.
European Examination Report, Application No. 12154307.8 dated Feb. 20, 2013.
European Examination Report, Application No. 12154343.3 dated Mar. 21, 2014.
European Examination Report, Application No. 07716208.9 dated Sep. 27, 2010.
European Examination Report, Application No. 07753450.1 dated Jan. 12, 2009.
European Examination Report, Application No. 07867402.5 dated Apr. 10, 2012.
European Examination Report, Application No. 07717903.4 dated Apr. 25, 2012.
European Examination Report, Application No. 09713926.5 dated Jul. 30, 2012.
European Examination Report, Application No. 11196265.0 dated Feb. 22, 2013.
European Examination Report, Application No. 12154304.5 dated Feb. 25, 2013.
European Examination Report, Application No. 09830750.7 dated Apr. 18, 2013.
European Examination Report, Application No. 12154342.5 dated Mar. 20, 2014.
European Examination Report, Application No. 08798444.9 dated May 15, 2014.
European Examination Report, Application No. 12165734.0 dated Apr. 29, 2014.
European Examination Report, Application No. 12154321.9 dated May 26, 2014.
European Examination Report, Application No. 12154334.2 dated May 16, 2014.

(56) References Cited

OTHER PUBLICATIONS

European Examination Report, Application No. 12154329.2 dated May 26, 2014.
European Examination Report, Application No. 12165740.7, dated Apr. 28, 2014.
European Examination Report, Application No. 06814375.9 dated Oct. 14, 2011.
European Examination Report, Application No. 12154339.1 dated May 16, 2014.
European Examination Report, Application No. 13159600.9 filed May 15, 2014.
European Examination Report, Application No. 12165638.3 dated Apr. 2, 2014.
European Examination Report, Application No. 12185438.4 dated Sep. 18, 2013.
European Examination Report, Application No. 12154354.0 dated Oct. 23, 2013.
European Examination Report, Application No. 08841700.1 dated Jun. 13, 2014.
European Examination Report, Application No. 08768266.2 dated Jul. 29, 2010.
European Examination Report, Application No. 12154327.6 filed May 26, 2014.
European Examination Report, Application No. 12154346.6 dated Jun. 27, 2013.
European Examination Report, Application No. 12165734.0 dated Aug. 14, 2013.
European Examination Report, Application No. 12154337.5 filed May 19, 2014.
European Examination Report, Application No. 08770974.7 dated Feb. 25, 2013.
European Examination Report, Application No. 12154350.8 dated Aug. 21, 2013.
European Examination Report, Application No. 09715356.3 dated Jul. 10, 2013.
European Examination Report, Application No. 08782609.5 dated May 24, 2012.
European Examination Report, Application No. 12154322.7 filed May 27, 2014.
European Examination Report, Application No. 08796821.0 dated Jul. 19, 2013.
European Examination Report, Application No. 12154347.4 dated Oct. 9, 2013.
European Examination Report, Application No. 12179595.9 dated May 12, 2014.
European Examination Report, Application No. 12179592.6 dated May 12, 2014.
European Examination Report, Application No. 08782609.5 dated Jun. 24, 2011.
European Extended Search Report, Application No. 12154352.4 dated Jan. 28, 2013.
European Extended Search Report, Application No. 12154349.0 dated Jan. 25, 2013.
European Extended Search Report, Application No. 10832355.1 dated May 13, 2014.
European Extended Search Report, Application No. 12154354.0 dated Jan. 28, 2013.
European Extended Search Report, Application No. 12185438.4 dated Mar. 28, 2013.
European Extended Search Report, Application No. 12165636.7 dated Sep. 25, 2012.
European Extended Search Report, Application No. 12185446.7 dated Mar. 28, 2013.
European Extended Search Report, Application No. 13159600.9 dated Sep. 19, 2013.
European Extended Search Report, Application No. 13175161.2 dated Sep. 24, 2013.
European Extended Search Report, Application No. 12179592.6 dated Jan. 21, 2013.
European Extended Search Report, Application No. 12165748.0 dated Jan. 11, 2013.
European Extended Search Report, Application No. 12179595.9 dated Jan. 23, 2013.
European Extended Search Report, Application No. 12154350.8 dated Jan. 25, 2013.
European Extended Search Report Application No. 07776079.1 dated Sep. 6, 2011.
European Extended Search Report, Application. No. 12154246.8 dated Jun. 4, 2012.
European Extended Search Report, Application No. 12154351.6 dated Jan. 31, 2013.
European Extended Search Report, Application No. 12154343.3 dated Jul. 10, 2012.
European Extended Search Report, Application No. 12154300.3 dated Dec. 7, 2012.
European Extended Search Report, Application No. 12154301.1 dated Jan. 11, 2013.
European Extended Search Report, Application No. 12154353.2 dated Jan. 31, 2013.
European Extended Search Report, Application No. 12165740.7 dated Jan. 11, 2013.
European Extended Search Report, Application No. 12165734.0 dated Jan. 11, 2013.
European Extended Search Report, Application No. 07867402.5 dated Nov. 24, 2009.
European Extended Search Report, Application No. 08767439.6 dated May 12, 2010.
European Extended Search Report, Application No. 11840508.3 dated Mar. 19, 2014.
European Seach Report, Application No. 09714868.8 dated Aug. 1, 2011.
European Seach Report, Application No. 11151749.6 dated Aug. 2, 2011.
European Search Report, Application No. 12154304.5 dated Jun. 26, 2012.
European Search Report, Application No. 07810382.7 dated Sep. 14, 2009.
European Search Report, Application No. 12154347.4 dated Sep. 27, 2012.
European Search Report, Application No. 12154354.0 dated Oct. 12, 2012.
European Search Report, Application No. 12154334.2 dated Sep. 21, 2012.
European Search Report, Application No. 12154342.5 dated Jul. 6, 2012.
European Search Report, Application No. 07867402.5 dated Nov. 22, 2011.
European Search Report, Application No. 09807241.6 dated Dec. 6, 2012.
European Search Report, Application No. 12154301.1 dated Aug. 22, 2012.
European Search Report, Application No. 12154300.3 dated Aug. 20, 2012.
European Search Report, Application No. 12154350.8 dated Sep. 27, 2012.
European Search Report, Application No. 09713926.5 dated Jul. 21, 2011.
European Search Report, Application No. 08770974.4 dated Oct. 21, 2011.
European Search Report, Application No. 08713330.2 dated Jul. 22, 2011.
European Search Report, Application No. 11151772.8 dated Aug. 2, 2011.
European Search Report, Application No. 12154337.5 dated Oct. 9, 2012.
European Search Report, Application No. 12154307.8 dated Jun. 26, 2012.
European Search Report, Application No. 12154321.9 dated Jul. 20, 2012.
European Search Report, Application No. 12185440.0 dated Apr. 12, 2013.

(56) References Cited

OTHER PUBLICATIONS

European Search Report, Application No. 12154341.7 dated Oct. 25, 2012.
European Search Report, Application No. 12154329.2 dated Sep. 19, 2012.
European Search Report, Application No. 08796821.0 dated Aug. 4, 2010.
European Search Report, Application No. 12165748.0 dated Aug. 23, 2012.
European Search Report, Application No. 08768266.2 dated Jul. 1, 2010.
European Search Report, Application No. 07872618.9 dated Jul. 5, 2010.
European Search Report, Application No. 07716208.9 dated Nov. 10, 2009.
European Search Report, Application No. 09715356.3 dated Jul. 12, 2012.
European Search Report, Application No. 12154326.8 dated Sep. 6, 2012.
European Search Report, Application No. 06825457.2 dated Sep. 16, 2009.
European Search Report, Application No. 12154322.7 dated Aug. 29, 2012.
European Search Report, Application No. 07717903.4 dated Oct. 23, 2009.
European Search Report, Application No. 06800599.0 dated Oct. 19, 2009.
European Search Report, Application No. 09830750.7 dated Aug. 27, 2012.
European Search Report, Application No. 12154327.6 dated Sep. 19, 2012.
European Search Report, Application No. 06814375.9 dated Oct. 8, 2009.
European Search Report, Application No. 07867402.5 dated Dec. 11, 2009.
European Search Report, Application No. 07717734.3 dated Nov. 9, 2009.
European Search Report, Application No. 12154351.6 dated Oct. 15, 2012.
European Search Report, Application No. 12165638.3 dated Jun. 12, 2012.
European Search Report, Application No. 07717903.4 dated Nov. 10, 2009.
European Search Report, Application No. 12165636.7 dated Jun. 8, 2012.
European Search Report, Application No. 12154332.6 dated Sep. 21, 2012.
European Search Report, Application No. 08841700.1 dated Jan. 4, 2011.
European Search Report, Application No. 11196265.0 dated Mar. 5, 2012.
European Search Report, Application No. 11196254.4 dated Feb. 28, 2012.
European Search Report, Application No. 12154349.0 dated Sep. 27, 2012.
European Search Report, Application No. 11170608.1 dated Aug. 29, 2011.
European Search Report, Application No. 12154300.3 dated Jan. 7, 2013.
European Search Report, Application No. 08782609.5 dated Oct. 28, 2010.
European Search Report, Application No. 11196256.9 dated Feb. 28, 2012.
European Search Report, Application No. 12154353.2 dated Oct. 15, 2012.
European Search Report, Application No. 11196261.9 dated Feb. 28, 2012.
European Search Report, Application No. 09715064.3 dated May 24, 2011.
European Search Report, Application No. 08798444.9 dated Dec. 16, 2010.
European Search Report, Application No. 08799295.4 dated Nov. 9, 2010.
European Search Report, Application No. 12154352.4 dated Oct. 12, 2012.
European Search Report, Application No. 11196264-3 dated Feb. 28, 2012.
European Search Report, Application No. 11196262.7 dated Feb. 28, 2012.
European Search Report, Application No. 11151771.0 dated Aug. 2, 2011.
European Search Report, Application No. 12154298.9 dated Jun. 4, 2012.
European Search Report, Application No. 12165734.0 dated Aug. 27, 2012.
European Search Report, Application No. 11151769.4 dated Aug. 2, 2011.
European Search Report, Application No. 12165740.7 dated Aug. 27, 2012.
European Search Report, Application No. 12154339.1 dated Oct. 9, 2012.
European Search Report, Application No. 12154346.6 dated Oct. 23, 2012.
European Search Report, Application No. 12154344.1 dated Sep. 19, 2012.
European Search Report, Application No. 08841700.1 dated Jun. 2, 2010.
European Search Report, Application No. 11196253.6 dated Apr. 24, 2012.
European Search Report, Application No. 08838376.5 dated Mar. 4, 2011.
European Search Report, Application No. 11196250.2 dated Apr. 24, 2012.
European Search Report, Application No. 11196190.0 dated Apr. 24, 2012.
European Search Report, Application No. 09763590.8 dated Aug. 29, 2011.
European Search Report, Application No. 12154348.2 dated Oct. 9, 2012.
European Search Report, Application No. 12154345.8 dated Sep. 19, 2012.
Japanese Notification of Reasons for Rejection, Application No. 2008-525107 dated Oct. 19, 2012.
Japanese Notification of Reasons for Rejection, Application No. 2010-548904 dated Sep. 2, 2013.
Japanese Notification of Reasons for Rejection, Application No. 2010-524221 dated Jun. 19, 2013.
Japanese Notification of Reasons for Rejection, Application No. 2010-519269 dated Jul. 12, 2013.
Japanese Notification of Reasons for Rejection, Application No. 2009-529212 dated Jul. 19, 2013.
Japanese Notification of Reasons for Rejection, Application No. 2008-549555 dated Dec. 12, 2012.
Japanese Notification of Reasons for Rejection, Application No. 2010-522058 dated Aug. 13, 2013.
Japanese Notification of Reasons for Rejection, Application No. 2010-531311 dated Sep. 2, 2013.
Japanese Notification of Reasons for Rejection, Application No. 2010-529072 dated Jun. 4, 2014.
Japanese Notification of Reasons for Rejection, Application No. 2010-519269 dated Jun. 23, 2014.
Japanese Notification of Reasons for Rejection, Application No. 2010-506300 dated Mar. 12, 2014.
Japanese Notification of Reasons for Rejection, Application No. 2013-081761 dated May 20, 2014.
Japanese Notification of Reasons for Rejection, Application No. 2008-532200 dated Jan. 30, 2012.
Japanese Notification of Reasons for Rejection, Appliction No. 2011-539528 dated Oct. 25, 2013.
Japanese Notification of Reasons for Rejection, Application No. 2012-284018 dated May 21, 2014.

(56) References Cited

OTHER PUBLICATIONS

Japanese Notification of Reasons for Rejection, Application No. 2008-549532 dated Feb. 24, 2012.
Japanese Notification of Reasons for Rejection, Application No. 2008-5251070 dated Jan. 4, 2012.
Japanese Notification of Reasons for Rejection, Application No. 2008-549549 dated Feb. 22, 2012.
Japanese Notification of Reasons for Rejection, Application No. 2008-549555 dated Feb. 24, 2012.
Japanese Notification of Reasons for Rejection, Application No. 2012-183280 dated Mar. 18, 2014.
Japanese Notification of Reasons for Rejection, Application No. 2010-548904 dated Apr. 1, 2014.
Japanese Notification of Reasons for Rejection, Application No. 2011-523144 dated Feb. 6, 2014.
Japanese Notification of Reasons for Rejection, Application No. 2010-511218 dated Mar. 13, 2014.
Japanese Notification of Reasons for Rejection, Application No. 2009-519525 dated Jul. 9, 2012.
Japanese Notification of Reasons for Rejection, Application No. 2009-519525 dated Nov. 1, 2012.
Japanese Notification of Reasons for Rejection, Application No. 2008-549532 dated Sep. 27, 2013.
Japanese Notification of Reasons for Rejection, Application No. 2009-501495 dated Jul. 27, 2012.
Japanese Notification of Reasons for Rejection, Application No. 2010-548907 dated Sep. 2, 2013.
Japanese Notification of Reasons for Rejection, Application No. 2009-548281 dated Sep. 3, 2013.
Japanese Notification of Reasons for Rejection, Application No. 2009-535366 dated Dec. 21, 2012.
Japanese Notification of Reasons for Rejection, Application No. 2010-511218 dated Jun. 3, 2013.
Japanese Notification of Reasons for Rejection, Application No. 2010-506300 dated Apr. 16, 2013.
Japanese Notification of Reasons for Rejection, Application No. 2009-529212 dated Oct. 17, 2012.
Japanese Notification of Reasons for Rejection, Application No. 2010-512377 dated Jun. 4, 2013.
Japanese Notification of Reasons for Rejection, Application No. 2010-529072 dated Jul. 30, 2013.
Japanese Notification of Reasons for Rejection, Application No. 2009-501495 dated Jun. 11, 2013.
Japanese Notification of Reasons for Rejection, Application No. 2010-548899 dated Oct. 8, 2013.
Notice of Allowance and Fees Due in U.S. Appl. No. 12/298,221, filed Nov. 10, 2008, mailing date Nov. 30, 2009.
Notice of Allowance and Fees Due in U.S. Appl. No. 12/160,064, filed Jul. 3, 2008, mailing date Nov. 20, 2009.
Office Action issued in U.S. Appl. No. 12/160,034, filed Jul. 3, 2008, mailing date Jun. 7, 2010.
Office Action issued in U.S. Appl. No. 12/442,018, filed Mar. 27, 2009, mailing date Apr. 15, 2010.
Office Action issued in U.S. Appl. No. 12/373,358, filed Feb. 11, 2009, mailing date Aug. 20, 2010.
Office Action issued in U.S. Appl. No. 12/293,471, filed Oct. 9, 2008, mailing date Jun. 8, 2010.
Office Action issued in U.S. Appl. No. 12/160,064, filed Jul. 3, 2008, mailing date Aug. 10, 2009.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Oct. 30, 2009.
Office Action issued in U.S. Appl. No. 12/083,067, filed Jun. 20, 2008, mailing date Jul. 8, 2010.
Office Action issued in U.S. Appl. No. 12/160,061, filed Jul. 3, 2008, mailing date Apr. 24, 2009.
PCT International Preliminary Report on Patentability, PCT/US2009/035470 filed Feb. 27, 2009, dated Aug. 31, 2010.
PCT International Preliminary Report on Patentability, PCT/US2010/057758 filed Nov. 23, 2010, dated Jun. 7, 2012.
PCT International Preliminary Report on Patentability, PCT/US2008/079482 filed Oct. 10, 2008, dated Apr. 13, 2010.
PCT International Preliminary Report on Patentability, PCT/US2012/068736, filed Dec. 10, 2012, dated Jun. 19, 2014.
PCT International Preliminary Report on Patentability, PCT/US2008/081294 filed Oct. 27, 2008, dated Apr. 27, 2010.
PCT International Preliminary Report on Patentability, PCT/US2007/015892 filed Jul. 12, 2007, dated Jan. 13, 2009.
PCT International Preliminary Report on Patentability, PCT/US2010/025173 filed Feb. 24, 2010, dated Sep. 9, 2011.
PCT International Preliminary Report on Patentability, PCT/US2009/038214 filed Mar. 25, 2009, dated Jun. 16, 2011.
PCT International Preliminary Report on Patentability, PCT/US2009/065072 filed Nov. 19, 2009, dated Jun. 3, 2011.
PCT International Preliminary Report on Patentability, PCT/US2009/035482 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2006/029889 filed Jul. 31, 2006, dated Feb. 5, 2008.
PCT International Preliminary Report on Patentability, PCT/US2007/006824 filed Mar. 19, 2007, dated Sep. 23, 2008.
PCT International Preliminary Report on Patentability, PCT/US2009/53586 filed Aug. 12, 2009, dated Feb. 24, 2011.
PCT International Preliminary Report on Patentability, PCT/US2007/009910 filed Apr. 24, 2007, dated Oct. 28, 2008.
PCT International Preliminary Report on Patentability, PCT/US2008/005503 filed Apr. 29, 2008, dated Nov. 3, 2009.
PCT International Preliminary Report on Patentability, PCT/US2011/034451 filed Apr. 29, 2011, dated Nov. 15, 2012.
PCT International Preliminary Report on Patentability, PCT/US2008/001157 filed Jan. 29, 2008, dated Aug. 4, 2009.
PCT International Preliminary Report on Patentability, PCT/US/2008/072081 filed Aug. 4, 2008, dated Feb. 9, 2010.
PCT International Preliminary Report on Patentability, PCT/US2006/038824 filed Oct. 4, 2006, dated Apr. 9, 2008.
PCT International Preliminary Report on Patentability, PCT/US2008/071532 filed Jul. 30, 2008, dated Feb. 2, 2010.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.
PCT International Preliminary Report on Patentability, PCT/US2007/020215 filed Sep. 17, 2007, dated Mar. 24, 2009.
PCT International Preliminary Report on Patentability, PCT/US2007/000024 filed Jan. 3, 2007, dated Jul. 8, 2008.
PCT International Preliminary Report on Patentability, PCT/US2007/000159 filed Jan. 3. 2007, dated Jul. 8, 2008.
PCT International Preliminary Report on Patentability, PCT/US2006/035100 filed Sep. 11, 2006, dated Mar. 18, 2008.
PCT International Preliminary Report on Patentability, PCT/US2007/000103 filed Jan. 3, 2007, dated Jul. 8, 2008.
PCT International Preliminary Report on Patentability, PCT/US2008/075565 filed Sep. 8, 2008, dated Mar. 9, 2010.
PCT International Preliminary Report on Patentability, PCT/US2008/073964 filed Aug. 22, 2008, dated Feb. 24, 2010.
PCT International Preliminary Report on Patentability, PCT/US2009/035458 filed Feb. 27, 2009, dated Aug. 31, 2010.
PCT International Preliminary Report on Patentability, PCT/US2007/023660 filed Nov. 1, 2007, dated May 5, 2009.
PCT International Search Report and the Written Opinion, PCT/US2007/00103 filed Jan. 3, 2007, dated Dec. 3, 2007.
PCT International Search Report and the Written Opinion, PCT/US2009/53586 filed Aug. 12, 2009, dated Oct. 28, 2009.
PCT International Search Report and the Written Opinion, PCT/US2011/060349 filed Nov. 11, 2011, dated Feb. 10, 2012.
PCT International Search Report and the Written Opinion, PCT/US2009/46999 filed Jun. 11, 2009, dated Nov. 23, 2009.
PCT International Search Report and the Written Opinion, PCT/US2006/29889 filed Jul. 31, 2006, dated Jul. 10, 2007.

(56) References Cited

OTHER PUBLICATIONS

PCT International Search Report and the Written Opinion, PCT/US2007/00159 filed Jan. 3, 2007, dated Apr. 11, 2008.
PCT International Search Report and the Written Opinion, PCT/US2010/025173 filed Feb. 24, 2010, dated Jul. 6, 2010.
PCT International Search Report and the Written Opinion, PCT/US2009/65072 filed Nov. 19, 2009, dated Mar. 3, 2010.
PCT International Search Report and the Written Opinion, PCT/US2008/73964 filed Aug. 22, 2008, dated Dec. 24, 2008.
PCT International Search Report and the Written Opinion, PCT/US2007/15892 filed Jul. 12, 2007, dated Sep. 30, 2008.
PCT International Search Report, PCT/US2007/006824 filed Mar. 19, 2007, dated May 14, 2008.
PCT International Search Report and the Written Opinion, PCT/US2008/79482 filed Oct. 10, 2008, dated Dec. 22, 2008.
PCT International Search Report and the Written Opinion, PCT/US2007/20215 filed Sep. 17, 2007, dated Jul. 25, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2011/29348 filed Mar. 22, 2011, dated Jun. 3, 2011.
PCT International Search Report and the Written Opinion, PCT/US2008/75565 filed Sep. 8, 2008, dated Dec. 9, 2008.
PCT International Search Report and the Written Opinion, PCT/US2007/006824 filed Mar. 19, 2007, dated Mar. 3, 2008.
PCT International Search Report and the Written Opinion, PCT/US2008/81294 filed Oct. 27, 2008, dated Mar. 26, 2009.
PCT International Search Report and the Written Opinion, PCT/US2012/060225 filed Oct. 15, 2012, dated Jan. 7, 2013.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/38214 filed Mar. 25, 2009, dated Aug. 14, 2009.
PCT International Search Report and the Written Opinion, PCT/US2008/72081 filed Aug. 4, 2008, dated Jan. 14, 2009.
PCT International Search Report and the Written Opinion, PCT/US2013/22492 filed Jan. 22, 2013, dated May 20, 2013.
PCT International Search Report and the Written Opinion, PCT/US2012/62853 filed Oct. 31, 2012, dated Mar. 14, 2013.
PCT International Search Report and the Written Opinion, PCT/US2011/41046 filed Jun. 20, 2011, dated Mar. 5, 2012.
PCT International Search Report and the Written Opinion, PCT/US2011/60838 filed Nov. 15, 2011, dated Mar. 21, 2012.
PCT International Search Report and the Written Opinion, PCT/US2012/68736 filed Dec. 10, 2012, dated Apr. 8, 2013.
PCT International Search Report and the Written Opinion, PCT/US2012/69484 filed Dec. 13, 2012, dated Apr. 29, 2013.
PCT International Search Report and the Written Opinion, PCT/US2007/23660 filed Nov. 1, 2007, dated Sep. 16, 2008.
PCT International Search Report and the Written Opinion, PCT/US2009/35482 filed Feb. 27, 2009, dated Jul. 17, 2009.
PCT International Search Report and the Written Opinion, PCT/US2007/09910 filed Apr. 24, 2007, dated Feb. 13, 2008.
PCT International Search Report and the Written Opinion, PCT/US2012/28016 filed Mar. 7, 2012, dated Aug. 3, 2012.
PCT International Search Report and the Written Opinion, PCT/US2012/67651 filed Dec. 3, 2012, dated May 13, 2013.
PCT International Search Report and the Written Opinion, PCT/US2008/84821 filed Nov. 26, 2008, dated Feb. 17, 2009.
PCT International Search Report and the Written Opinion, PCT/US2006/38824 filed Oct. 4, 2006, dated Aug. 9, 2007.
PCT International Search Report and the Written Opinion, PCT/US2006/35100 filed Sep. 11, 2006, dated Sep. 5, 2007.
PCT International Search Report and the Written Opinion, PCT/US2007/00024 filed Jan. 3, 2007, dated Nov. 5, 2007.
PCT International Search Report and the Written Opinion, PCT/US2012/020911 filed Jan. 11, 2012, dated Apr. 25, 2012.
PCT Invitation to Pay Additional Fees, PCT/US2012/028016 filed Mar. 7, 2012, dated May 29, 2012.
PCT Written Opinion, PCT/US2009/051942 filed Jul. 28, 2009, dated Jan. 26, 2010.
Ahmad, et al., "Distant Metastases of Nasopharyngeal Carcinoma: A Study of 256 Male Patients," Journal of Surgical Oncology, 1986, vol. 33, pp. 194-197.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Alberts, B. et al., Molecular Biology of the Cell, 3rd Edition, 1994, p. 465.
Alvarez-Secord, A. et al., "Maspin Expression in Epithelial Ovarian Cancer and Associations with Poor Prognosis: A Gynecologic Oncology Study," Gyencologic Oncology, 2006, pp. 390-397, vol. 101.
Ambros, MicroRNA Pathways in Flies and Worms: Growth, Death, Fat, Stress, and Timing, Nature, 2004, vol. 431, pp. 350-355.
Ambros, V. et al., "A Uniform System for MicroRNA Annotation," RNA, 2003, pp. 277-279, vol. 9.
Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.
Andriani, "Increased Sensitivity to Cisplatin", Neoplasia, vol. 8, No. 1, pp. 9-17.
Aqeilan, R. I. et al., "Targeted Deletion of WWOX Reveals a Tumor Suppressor Function," PNAS, Mar. 2007, pp. 3949-3954, vol. 104, No. 10.
Arata, et al., Cdk2-dependent and -independent Pathways in E2F-mediated S Phase Induction, J. Biol. Chem, 2000.
Asangani, IA,, et al., MicroRNA-21 (miR-21) post-transcriptionally downregulates tumor suppressor Pdcd4 and stimulates invasion, intravasation and metastasis in colorectal cancer, Oncogene, 2008, vol. 27, pp. 2128-2136.
Attwooll, et al., The E2F family: specific functions and overlapping interests, EMBO, 2004.
Baira, E. et al., "Ultraconserved Elements: Genomics, Function and Disease," RNA Biology, Jul. 2008, pp. 132-134, vol. 5, No. 3.
Bakkus, M. et al., "MicroRNA Expression Analysis in Multiple Myeloma Plasma Cells and Cell Lines by a Quantitative Real-Time PCR Approach," Blood, 2007, p. 729A, vol. 110, No. 11, Abstract.
Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.
Bao, B. et al. Anti-Tumor Activity of a Novel Compound, PLOS One, 2011, vol. 6, Issue 3, pp. 1-12.
Barad, O. et al., "MicroRNA Exrpession Detected by Oligonucleotide Microarrays: System Establishment and Expression Profiling in Human Tissues," Genome Research, 2004, pp. 2846-2494, vol. 14.
Bartel, D. P., "MicroRNAs: Target Recognition and Regulatory Functions," Cell, Jan. 2009, pp. 215-233, vol. 136.
Bartel, MicroRNAs: Genomics, Biogenesis, Mechanism, and Function, Cell, vol. 116, 2004, pp. 281-297.

(56) References Cited

OTHER PUBLICATIONS

Basu, et al., MicroRNA-375 and MicroRNA-221:Potential Noncoding RNAs Associated with Antiproliferative Activity of Benzyl Isothiocyanate in Pancreatic Cancer, Croce, Genes & Cancer, 2011, pp. 108-119.
Baudhuin, L.M. et al., "Use of Microsatellite Instability and Immunohistochemistry Testing for the Identification of Individuals at Risk for Lynch Syndrome," Fam. Cancer, 2005, pp. 255-265, vol. 4, No. 3.
Bednarek, A. K. et al., "WWOX, the FRA16D Gene, Behaves as a Suppressor of Tumor Growth," Cancer Research, Nov. 2001, pp. 8068-8073, vol. 61.
Bejenaro, etal., "Ultraconserved Elements in the Human Genome," Electronic Suppl. Data, Science, 2004.
Bejerano, Computational Screening of Conserved Genomic DNA—Nature Methods, 2005, vol. 2, No. 7, pp. 535-545.
Bejerano, G. et al., "Ultraconserved Elements in the Human Genome," Science, May 2004, pp. 1321-1325, vol. 304.
Belinsky, et al., Inhibition of DNA Methylation and Histone Deacetylation Prevents Murine Lung Cancer, Cancer Research 63, 2004, pp. 7089-7093.
Bell, D. A., "Origins and Molecular Pathology of Ovarian Cancer," Modern Pathology, 2005, pp. S19-S32, vol. 18.
Bendoraite, et al, Regulation of miR-200 family microRNAs and ZEB transcription factors in ovarian cancer: evidence supporting a mesothelial-toepithelial transition, Gyneol Oncol, 2010, vol. 116, pp. 117-125.
Bichi, R. et al., "Human Chronic Lymphocytic Leukemia Modeled in Mouse by Targeted TCL1 Expression," PNAS, May 2002, pp. 6955-6960, vol. 99, No. 10.
Bloomston, et al., Identification of Molecular Markers Specific for Pancreatic Neuroendocrine Tumors by Genetic Profiling of Core Biopsies, Ann. Surg. Oncol. 2004, vol. 11, 4, pp. 413-419.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blow, Replication licensing—defining the proliferative state, Cell Biol, 2002.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Boominathan, L., The Tumor Suppressors p53-p63 and p72, PLOS ONE, May 2010, vol. 5, Issue 5, pp. 1-13.
Braun et al., "p53-Responsive MicroRNAs 192 and 215 are Capable of Inducing Cell Cycle Arrest," Cancer Research, 2008, pp. 10094-10104, vol. 68.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Budhu, et al., Prediction of venous metastases, recurrence, and prognosis inhepatocellular carcinoma based on a unique immune response signature of the liver microenvironment, Cancer Cell, 2006, vol. 10, 2, pp. 99-111.
Butz, H. et al., "Down-Regulation of Wee1 Kinase by a Specific Subset of MicroRNA Sporadic Pituitary Adenomas," Journal of Clinical Endocrinol Metab, Oct. 2010, pp. E181-E191, vol. 95, No. 10.
Caldas, C. et al., "Sizing Up miRNAs as Cancer Genes," Nature Medicine, Jul. 2005, pp. 712-714, vol. 11, No. 7.
Calin, G. A. et al., "Ultraconserved Regions Encoding ncRNAs are Altered in Human Leukemias and Carcinomas," Cancer Cell, Sep. 2007, pp. 215-229, vol. 12.
Calin, G. A. et al., "MicroRNA Signatures in Human Cancers," Nature Reviews Cancer, Nov. 2006, pp. 857-866, vol. 6.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Cannistra, S.A., "Cancer of the Ovary," The New England Journal of Medicine, 2004 pp. 2519-2529, vol. 351, No. 25.
Castoldi, M. et al., "A Sensitive Array for MicroRNA Expression Profiling (miChip) Based on Locked Nucleic Acids (LNA)," RNA, 2006, pp. 913-920, vol. 12.
Chambers, et al., Dissemination and Growth of Cancer Cells in Metastatic Sites, Nat. Rev. Cancer, 2002, vol. 2, pp. 563-572.
Chan, et al., Concordant and Discordant Regulation of Target Genes by miR-31 and Its Isoforms, PLOS One, 2013, vol. 8, pp. 1-11.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.
Chang, T. C., et al., Transactivation of miR-34a by p53, Molecular Cell 26, pp. 745-752, 2007.
Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Chen, et al., Expanded Polyglutamine-Binding Peptoid as a Novel Therapeutic Agent for Treatment of Huntington's Disease, Chemistry Biology, 2011, vol. 18, pp. 1113-1125.
Chen, et al., Real-time quantification of microRNAs by stem-loop RT-PCR, Nucleic Acids, 33, 2005, e179.
Chen,et al., Downregulation of miR-221/222 sensitizes glioma cells to tempzolomide by regulating apoptosis independently of p53 status, Onocolgy Reports, 2012, vol. 27, pp. 854-860.
Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Chim, S.S.C. et al., "Detection and Characterization of Placental MicroRNAs in Maternal Plasma," Clinical Chemistry, 2008, pp. 482-490, vol. 54, No. 3.
Cho "OncomiRs: The Discovery and Progress of MicroRNAs in Cancers," Molecular Cancer, Sep. 2007, vol. 6, No. 60, pp. 1-7.
Chun-Zhi, et al., MicroRNA-221 and microRNA-222 regulate gastric carcinoma cell proliferation and radioresistance by targeting PTEN, BMC Cancer, 2010, gastric, vol. 10, pp. 1-10.
Ciafre, S. A. et al., "Extensive Modulation of a Set of MicroRNAs in Primary Glioblastoma," Biochemical and Biophysical Research Communications, 2005, pp. 1351-1358, vol. 334.

(56) References Cited

OTHER PUBLICATIONS

Cillo, et al., The critical issue of hepatocellular carcinoma prognostic classification: which is the best tool available, J. Hepatol., 2004, vol. 40, 1, pp. 124-131.
Cimmino, A. et al., Corrections to "miR-15 and miR-16 Induce Apoptosis by Targeting BCL2," PNAS, Feb. 2006, pp. 2464-2465, vol. 103, No. 7.
Cimmino, A. et al., "miR-15 and miR-16 Induce Apoptosis by Targeting BCL2," PNAS, Sep. 2005, pp. 13944-13949, vol. 102, No. 39.
Costinean, S. et al., "Pre-B Cell Proliferation and Lymphoblastic Leukemia/ High-Grade Lymphoma in Eµ-miR155 Transgenic Mice," PNAS, May 2006, pp. 7024-7029, vol. 103, No. 18.
Cowgill, The genetics of pancreatic cancer Am. J. Surg, 2003, vol. 186, 3, pp. 279-286.
Croce, C. M. et al., "Role of FHIT in Human Cancer," Journal of Clinical Oncology, May 1999, pp. 1618-1624, vol. 17, No. 5.
Croce, C. M. et al., "miRNAs, Cancer, and Stem Cell Division," Cell, 2005, pp. 6-7, vol. 36.
Croce, C. M., "Causes and Consequences of MicroRNA Dysregulation in Cancer," Nature Reviews Genetics, Oct. 2009, pp. 704-714, vol. 10.
Croce, C. M., "Oncogenes and Cancer," The New England Journal of Medicine, Jan. 2008, pp. 502-511, vol. 358, No. 5.
Cui, S. et al., "MicroRNAs that Underlie Ovarian Cancer Development and Response to Chemotherapy," 98th AACR Annual Meeting, Apr. 14-18, 2007, Los Angeles, CA.
Dahiya, N. et al., "MicroRNA Expression and Identification of Putative miRNA Targets in Ovarian Cancer," Plos One, Jan. 2008, pp. 1-11, vol. 3, No. 6.
Dalmay, T. et al., "MicroRNAs and the Hallmarks of Cancer," Oncogene, 2006, pp. 6170-6175, vol. 25.
Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
Davies, F. E. et al., "Insights into the Multistep Transformation of MGUS to Myeloma Using Microarray Expression Analysis," Blood, Dec. 2003, pp. 4504-4511, vol. 102, No. 13.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Delott, et al., CDX2 Is a Useful Marker of Intestinal-Type Differentiation Arch. Pathol. Lab, Med, 2005 vol. 129, 9, pp. 1100-1105.
Dignam, et al., Accurate transcription initiation by RNA polymerase D in a soluble extract from isolated mammalian nuclei, Nucleic Acids Res., 11, 1983, pp. 1475-1489.
Dohner, H. et al., "Genomic Aberrations and Survival in Chronic Lymphocytic Leukemia," The New England Journal of Medicine, Dec. 2000, pp. 1910-1916, vol. 343, No. 26.
Druck, etal., "FHIT," Atlas of Genetics and Cytogenetics in Oncology and Haematology, 2007, pp. 171-178, vol. 2.
Enrich, et al., Quantitative High-Throughput Analysis of DNA Methylation Patterns by Base-Specific Cleavage and Mass Spectrometry, PNAS, vol. 102, 2005, pp. 15785-15790.
Eiriksdottir, G. et al., "Mapping Loss of Heterozygosity at Chromosome 13q: Loss at 13q12-q13 is Associated with Breast Tumour Progression and Poor Prognosis," European Journal of Cancer, 1998, pp. 2076-2081, vol. 34, No. 13.
Eis, P. S. et al., "Accumulation of miR-155 and BIC RNA in Human B Cell Lymphomas," PNAS, Mar. 2005, pp. 3627-3632, vol. 102, No. 10.
Esquela-Kerscher, A. et al., "Oncomirs—MicroRNAs with a Role in Cancer," Nature Reviews:Cancer, Apr. 2006, pp. 259-269, vol. 6.
Eychene, A. et al., "A New MAFia in Cancer," Nature Reviews Cancer, Sep. 2008, pp. 683-693, vol. 8.
Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.
Fabbri, M. et al., "MicroRNAs," The Cancer Journal, Jan./Feb. 2008, pp. 1-6, vol. 14, No. 1.
Fabbri, M. et al., "WWOX Gene Restoration Prevents Lung Cancer Growth In Vitro and In Vivo," PNAS, Oct. 2005, pp. 15611-15616, vol. 102, No. 43.
Faguet, Chronic Lymphocytic Leukemia: An Updated Review, Journal of Clinical Oncology, 1994, vol. 12, No. 9, pp. 1974-1990.
Farazi, et al., MicroRNA Sequence and Expression Analysis in Breast Tumors by Deep Sequencing, Cancer Research, 71(13), Jul. 1, 2011, pp. 4443-4453.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Feng, G. et al., "Elevated Serum-Circulating RNA in Patients with Conventional Renal Cell Cancer," Anticancer Research, 2008, pp. 321-326, vol. 28.
Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.
Fong, Y. et al., "Muir-Torre-Like Syndrome in FHIT-Deficient Mice," PNAS, Apr. 2000, pp. 4742-4747, vol. 97, No. 9.
Ford, L.P., "A MicroRNA Expression Signature of Human Solid Tumors Defines Cancer Gene Targets," Leukemia Research, 2006, pp. 511-513, vol. 30.
Fornari, et al., MiR-221 controls CDKNIC/p57 and CDKNIB/p27 expression in human hepatocellular carcinoma, Oncogene 2008, vol. 27, pp. 5651-5661.
Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Fulci, et al., Quantitative Technologies Establish a Novel MicroRNA Profile of Chronic Lymphocytic Leukemia, Blood, Jun. 1, 2007, vol. 109, pp. 4944-4951.
Gailiun, M., "Single MicroRNA Causes Cancer in Transgenic Mice," Research Communications, The Ohio State University, Apr. 2006, pp. 1-3.
Gang, M. et al., "Expression of Programmed Cell Death 4 and Its Clinicopathological Significance in Human Pancreatic Cancer," Acta Academae Medicinae Sinicae, Abstract, 2005, pp. 597-600, vol. 27.
Garcea, et al., Molecular prognostic markers in pancreatic cancer, A systematic review, Eur. J. Cancer, 2005, vol. 4, 15, pp. 2213-2236.
Garofalo, et al., MiR-221&222 enchance migration and invasiveness of NSCLC and hepatocarcinoma cells by targeting PTEN tumor suppressor, AACR, 2009.
Garofalo, et al., miR221/222 in Cancer: Their Role in Tumor Progression and Response to Therapy, Current Molecular Medicine, 2012, 12, pp. 27-33.
Garofalo, M. et al., "miR-221&222 Regulate Trail Resistance and Enhance Tumorigenicity through PTEN and TIMP3 Downregulation," Cancer Cell, Dec. 2009, pp. 498-509, vol. 16.
Garofalo, M. et al., "MicroRNA Signatures of TRAIL Resistance in Human Non-Small Cell Lung Cancer," Oncogene, 2008, pp. 3845-3855, vol. 27.
Garzon et al., MicroRNA signatures associated with cytogenetics and prognosis in acute myeloid leukemia; Blood, Mar. 15, 2008, vol. 111, No. 6.
Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, R. et al., "MicroRNA Expression and Function in Cancer," TRENDS in Molecular Medicine, Oct. 2006, pp. 580-587, vol. 12, No. 12.
Garzon, R. et al., "MicroRNA Fingerprints During Human Megakaryocytopoiesis," PNAS, Mar. 2006, pp. 5078-5083, vol. 103, No. 13.

(56) References Cited

OTHER PUBLICATIONS

Garzon, R. et al., "MicroRNA Signatures Associated with Cytogenetics and Prognosis in Acute Myeloid Leukemia," Blood, Published Online Jan. 2008, DOI: 10.1182/blood-2007-07-098749, pp. 1-34.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Ghaneh, et al., Molecular prognostic markers in pancreatic cancer, J. Hepatobiliary, Pancreat. Surg., 2002, vol. 9, pp. 1-11.
Ghoshal, et al., Up-regulation of oncogenic microRNAs and down-regulation of their tumor suppressor targets play a casual role in the initiation of hepatocarcinogenesis in mice fed choline-deficient and amino acid defined diet, AACR, 2008.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.
Goel, A., et al., A Novel Mechanism for Aspirin Mediated Growth Inhibition, Clin Cancer Res, 2003, vol. 9, pp. 383-390.
Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.
Greenbaum, D. et al., "Comparing Protein Abundance and mRNA Expression Levels on a Genomic Scale," Genome Biology, 2003, pp. 117.1-117.8, vol. 4, Issue 9.
Gregory, et al., MicroRNA Biogenesis and Cancer, Cancer Res, 2005, vol. 65, 9, pp. 3509-3512.
Gregory, et al., The Microprocessor complex mediates the genesis of microRNAs, Nature, 432, 2004, pp. 235-240.
Grier, D.G. et al., "The Pathophysiology of HIX Genes and Their Role in Cancer," Journal of Pathology, 2005, pp. 154-171, vol. 205.
Griffiths-Jones, S. et al., "miRBase: MicroRNA Sequences, Targets and Gene Nomenclature," Nucleic Acids Research, 2006, pp. D140-D144, vol. 34.
Griffths-Jones, S. et al., "miRBase: Tools for MicroRNA Genomics," Nucleic Acids Research, 2008, pp. D154-D157, vol. 36.
Griffths-Jones, S., "The MicroRNA Registry," Nucleic Acids Research, 2004, pp. D109-D111, vol. 32.
Gu, et al., The t(4;II) Chromosome Translocation of Human Acute Leukemias Fuses the ALL-7 Gene, Related to *Drosophila* trithorax, to the AF-4 Gene, Cell 71, 1992, pp. 701-709.
Guenther, et al., Global and Hox-specific roles for the MLL1 methyltransferase, PNAS, 102, 2005, pp. 8603-8608.
Guerrette, S. et al., "Interactions of Human hMSH2 with hMSH3 and hMSH2 with hMSH6: Examination of Mutations Found in Hereditary Nonpolyposis Colorectal Cancer," Molecular and Cellular Biology, Nov. 1998, pp. 6616-6623, vol. 18, No. 11.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Habbe, et al., MicroRNA miR-155 is a biomarker of early pancreatic neoplasia, Cancer Biol Therapy, 2009, pp. 340-346.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
He, H. et al., "The Role of MicroRNA Genes in Papillary Thyroid Carcinoma," PNAS, Dec. 2005, pp. 19075-19080, vol. 102, No. 52.
He, L. et al., "A MicroRNA Polycistron as a Potential Human Oncogene," Nature, Jun. 2005, pp. 828-833, vol. 435.
He, X. et al., "MicroRNA and Esophageal Carcinoma," Journal of Nanjing Medical University, 2007, pp. 201-206, vol. 21, No. 4.

Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hezel, et al., Genetics and biology of pancreatic ductal adenocarcinoma, Genes Dev., 2006, vol. 20, pp. 1218-1249.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Hu, et al., A miR-200 microRNA cluster as prognostic marker in advanced ovarian cancer, Gynecol Oncol, 2009, vol. 114, pp. 457-464.
Huang, et al., Evaluation of predictive value of CLIP, Okuda, TNM and JIS staging systems for hepatocellular carcinoma patients undergoing surgery, J. Gastroenterol Hepatol, 2005, vol. 20, 5, pp. 765-771.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Hudlebusch, H. et al., "Expression of HOXA Genes in Patients with Multiple Myeloma," Leukemia & Lumphoma, Jun. 2004, pp. 1215-1217, vol. 45, No. 6.
Hutvagner, et al., A MicroRNA in a Multiple Turnover RNAi Enzyme Complex, Science, 2002, vol. 297, 5589, pp. 2056-2060.
Iizuka, et al., Oligonucleotide microarray for prediction of early intrahepatic, Lancet, 2003, vol. 361, 9361, pp. 923-929.
Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.
Iliopoulos, D. et al., "Inhibition of Breast Cancer Growth In Vitro and In Vivo: Effect of Restoration of WWOX Expression," Clin. Cancer Research, Jan. 2007, pp. 268-274, vol. 13, No. 1.
Iorio et al., MicroRNAs in Cancer: Small Molecules With a Hugh Impact, Journal of Clinical Oncology, vol. 27, Dec. 1, 2009, pp. 5848-5856.
Iorio, et al., Causes and consequences of microRNA Dysregulation, Cancer Journal, 2012, vol. 18, pp. 215-222.
Iorio, et al., MicroRNA dysregulation in cancer: diagnostics, monitoring and therapeutics. A comprehensive review. EMBO Mol Med 4, pp. 143-159, 2012.
Iorio, et al., MicroRNA Involvement in Human Cancer, Advance Access, 2012, pp. 1126-1133.
Iorio, M. V. et al., "MicroRNA Signatures in Human Ovarian Cancer," Cancer Research, Sep. 2007, pp. 8699-8707, vol. 67, No. 18.
Iorio, M. V. et al., "MicroRNA Gene Expression Deregulation in Human Breast Cancer," Cancer Research, Aug. 2005, pp. 7065-7070, vol. 65, No. 16.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Izzotti, A. et al., Relationships of MicroRNA Expression in Mouse, FASEB Journal, vol. 23, Sep. 2009, pp. 3243-3250.
Jacobs, I.J. et al., "Progress and Challenges in Screening for Early Detection of Ovarian Cancer," Molecular & Cellular Proteomics, 2004, pp. 355-366, vol. 3.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Janis, L.S., Ephrin-A Binding and EphA Receptor Expression Delineate the Matrix Compartment of the Striatum, The Journal of Neuroscience, Jun. 15, 1999, 19(12), pp. 4962-4971.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Jazbutyte, V. et al., "MicroNRA-21: From Cancer to Cardiovascular Disease," Current Drug Targets, Abstract, 2010, pp. 926-935, vol. 11.
Jemal, A. et al., "Cancer Statistics," CA Cancer J. Clin., 2008, pp. 71-96, vol. 58, No. 2.

(56) References Cited

OTHER PUBLICATIONS

Jemal, et al., Cancer Statistics, Cancer Stats vol. 57, 2007, pp. 43-66.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.
Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.
Jiang, J. et al., "Real-Time Expression Profiling of MicroRNA Precursors in Human Cancer Cell Lines," Nucleic Acids Research, 2005, pp. 5394-5403, vol. 33, No. 17.
Johansson, et al., Hematologic malignancies with t(4;11)(q21;q23) a cytogenetic, morphologic, immunophenotypic and clinical study of 183 cases, Leukemia, 12, 1998, pp. 779-787.
John, B. et al., "Human MicroRNA Targets," PLOS Biology, Nov. 2004, pp. 1862-1879, vol. 2, Issue 11.
Johnson, et al., Treatment of Chronic Lymphocytic Leukemia by Total Body Irradiation Alone and Combined With Chemotherapy, International Journal of Radiation Oncology, 1979, vol. 5, No. 2, pp. 159-164.
Johnson, S. M. et al., "RAS is Regulated by the let-7 MicroRNA Family," Cell, Mar. 2005, pp. 635-647, vol. 120.
Jover, et al., The Efficacy of adjuvant chemotherapy with 5-fluorouracil in colorectal cancer depends on the mismatch repair status, European Journal of Cancer, Pergamon Press, Oxford, GB, vol. 45, No. 3, Feb. 1, 2009, pp. 365-373.
Kan, et al., Elevated Levels of Circulating MicroRNA, BMC, Cancer, 2012, vol. 12, pp. 2-9.
Kane, M.F. et al., "Methylation of the hMLH1 Promoter Correlates with Lack of Expression of hMLH1 in Sporadic Colon Tumors and Mismatch Repair-Defective Human Tumor Cell Lines," Cancer Research, 1997, pp. 808-811, vol. 57.
Kawasaki, H. et al., "MicroRNA-196 Inhibits HOXB8 Expression in Myeloid Differentiation of HL60 Cells," Nucleic Acids Symposium Series, 2004, pp. 211-212, No. 48.
Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.
Kim, et al., FHIT Protein Enhances Paclitaxel-Induced Apoptosis, Int. J. Cancer, vol. 118, pp. 1692-1698, 2006.
Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.
Kim, MicroRNA Biogenesis: Coordinated Cropping and Dicing, Nature Rev. Mol. Cell Bio, vol. 6, 2005, pp. 376-385.
Kim, Processing of intronic microRNAs, EMBO, 2007, vol. 26, 3, pp. 775-783.
Kluiver, et al., "Lack of BIC and MicroRNA miR-155 Expression in Primary Cases of Burkitt Lymphoma", Genes, Chromosomes & Cancer, 2006, vol. 45, 2, pp. 147-153.
Kluiver, et al., BIC and miR-155 are highly expressed in Hodgkin, primary mediastinal and diffuse large B cell lymphomas, J. Pathol., 2005, 207, 2, pp. 243-249.
Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.
Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.

Kozomara, A. et al., "miRBase: Integrating MicroRNA Annotation and Deep-Sequencing Data," Nucleic Acids Research, 2011, pp. D152-D157, vol. 39.
Krek, A. et al., "Combinatorial MicroRNA Target Predictions," Nature Genetics, May 2005, pp. 495-500, vol. 37, No. 5.
Kudo, et al., Prognostic staging system for hepatocellular carcinoma (CLIP score): its value and limitations, and a proposal for a new staging system, the Japan Integrated Staging Score (JIS score), J. Gastroenterol, 2003, vol. 38, 3, pp. 207-215.
Kulshreshtha, R. et al., "A MicroRNA Signature of Hypoxia," Molecular and Cellular Biology, Mar. 2007, pp. 1859-1867, vol. 27, No. 5.
Kuroki, et al., "Genetic Alterations of the Tumor Suppressor Gene WWOX in Esophageal Squamous Cell Carcinoma," Cancer Research, Apr. 2002, pp. 2258-2260, vol. 62.
Kutay, H. et al., "Downregulation of miR-122 in the Rodent and Human Hepatocellular Carcinomas," Journal of Cellular Biochemistry, 2006, pp. 671-678, vol. 99.
Lagos-Quintana, et al., Identification of Novel Genes Coding for Small Expressed RNA's, Science, 2001, vol. 294, 5543, pp. 853-858.
Lagos-Quintana, M. et al., "Identification of Tissue-Specific MicroRNAs from Mouse," Current Biology, Apr. 2002, pp. 735-739, vol. 12.
Lagos-Quintana, M. et al., "New MicroRNAs From Mouse to Human," RNA, 2003, pp. 175-179, vol. 9, No. 2.
Lall, et al., A Genome-Wide Map of Conserved MicroRNA Targets in *C. elegans*, Curr Biol 16, 2006, pp. 460-471.
Landgraf, P. et al., "A Mammalian MicroRNA Expression Atlas Based on Small RNA Library Sequencing," Cell, Jun. 2007, pp. 1401-1414, vol. 129.
Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.
Landthaler, et al., The Human DiGeorge Syndrome Critical Region Gene 8 and Its *D. melanogaster* Homolog are Required for miRNA Biogenesis, Current Biology, 14, 2004, pp. 2162-2167.
Lanza, G. et al., "mRNA/microRNA Gene Expression Profile in Microsatellite Unstable Colorectal Cancer," Molecular Cancer, 2007, pp. 1-11, vol. 6, No. 54.
Lau, et al., An Abundant Class of Tiny RNA's With Probable Regulatory Roles in *Caenorhabditis elegans*, Science 2001, vol. 294, 5543, pp. 858-862.
Lawrie, C. H. "MicroRNAs and Haematology: Small Molecules, Big Function," British Journal of Haematology, Jun. 2007, pp. 503-512, vol. 137, No. 6.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Lawrie, C.H., "MicroRNA, Expression in Lymphoma," Expert Opinoin on Biological Therapy, Sep. 2007, pp. 1363-1374, vol. 7, No. 9.
Lecellier, et al., A Cellular MicroRNA mediates Antiviral, Science, 2005, vol. 308, pp. 557-560.
Lee, E. J. et al., "Expression Profiling Identifies MicroRNA Signature in Pancreatic Cancer," Int. J. Cancer, 2006, pp. 1046-1054, vol. 120.
Lee, E.J., "Expression and Function of MicroRNA in Human Cancer," Dissertation, The Ohio State University, 2008.
Lee, et al., An Extensive Class of Small RNA's in *Caenorhabditis elegans*, Science, 2001, vol. 294, 5543, pp. 862-864.
Lee, et al., MicroRNA maturation: stepwise processing and subcellular localization, EMBO, J. 2002, vol. 21, 17, pp. 4663-4670.
Lee, Y.S. et al., "MicroRNAs: Small but Potent Onogenes or Tumor Suppressors," Current Opinion in Investigational Drugs, Jun. 2006, pp. 560-564, vol. 7, No. 6.
Levitt P, et al., Dissociation of corticothalamic and thalamocortical axon targeting by an ephA7-mediated mechanism, International Journal of Developmental Neuroscience, vol. 24, No. 8, Dec. 1, 2006, p. 489.
Levy, et al., Staging of hepatocellular carcinoma: assessment of the CLIP, Okuda, and Child-Pugh staging systems in a cohort of 257 patients in Toronto, Gut, 2002, vol. 50, 6, pp. 881-885.

(56) References Cited

OTHER PUBLICATIONS

Lewis, B. P. et al., "Prediction of Mammalian MicroRNA Targets," Cell, Dec. 2003, pp. 787-798, vol. 115.
Lewis, et al., Conserved Seed Pairing, Often Flanked by Adenosines, Indicates that Thousands of Human Genes are MicroRNA Targets, Cell, 2005, vol. 120, 1, pp. 15-20.
Li et al., miR-181a Is an Intrinsic Modulator of T Cell Sensitivity and Selection, Cell 2007, pp. 147-161.
Li, et al., DNA mismatch repair (MMR)-dependent 5-fluorouracil cytotoxicity and the potential for new therapeutic targets, British Journal of Pharmacology, 2009, vol. 158, pp. 679-692.
Li, et al., Expression of serum miR-221 in human heptocellular carcinoma and its prognostic significance, Biochemical Biophys Res Commun, 2011, vol. 406, pp. 70-73.
Li, S.-C. et al., "Bioinformatic Discovery of MicroRNA Precursors from Human ESTs and Introns," BMC Genomics, 2006, vol. 7.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Lin, et al., Alteration of DNA methyltransferases contributes to 5 CpG methylation and poor prognosis in lung cancer, LungCancer, vol. 55, 2007, pp. 205-213.
Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.
Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.
Liu, et al., Characterization of in vitro and in vivo hypomethylating effects of decitabine in acute myeloid leukemia by a rapid, specific and sensitive LC-MS/MS method, Nucleic Acids, vol. 35, 2007, e31.
Liu, et al., Increased Expression of MicroRNA-221 in Gastric Cancer and Its Clinical Significance, Journal of International Medical Research, 2012, vol. 40, pp. 467-474.
Liu, Tissue inhibitor of metalloproteinase-1 protects human breast epithelial cells from extrinsic cell death: a potential oncogenic activity of tissue inhibitor of metalloproteinase-1, Cancer Research, vol. 65, No. 3, pp. 898-906, 2003.
Loffler, D. et al., "Interleukin-6-Dependent Survival of Multiple Myeloma Cells Involves the Stat3-Mediated Induction of MicroRNA-21 Through a Highly Conserved Enhancer," Blood, 2007, pp. 1330-1333, vol. 110, No. 4.
Lu, J. et al., "MicroRNA Expression Profiles Classify Human Cancers," Nature, Jun. 2005, pp. 834-838, vol. 435.
Lujambio, A. et al., "A MicroRNA DNA Methylation Signature for Human Cancer Metastasis," PNAS, Sep. 2008, pp. 13556-13561, vol. 105, No. 36.
Ma, G. et al., "Expression of Programmed Cell Death 4 and Its Clinicopathological Significance in Human Pancreatic Cancer," Medline, Department of General Surgery, the First Affiliated Hospital, China Medical University, Oct. 2005, pp. 597-600.
Ma, X., et al., MicroRNAs in NF-kB signaling, Journal of Molecular Cell Biology, 2011, vol. 3, pp. 159-166.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Marsit, et al., MicroRNA Responses to Cellular Stress, Cancer Research, 2006, vol. 66, pp. 10843-10848.
Martin, M. et al., "MicroRNA-155 Regulates Human Angiotensin II Type 1 Receptor Expression in Fibroblasts," The Journal of Biological Chemistry, Jul. 2006, pp. 18277-18284, vol. 281, No. 27.
Mascellani, N. et al., "Using miRNA Expression Data for the Study of Human Cancer," Minerva Biotec, 2008, pp. 23-30, vol. 20.
Masri, A. et al., "MicroRNA Expression Analysis in Multiple Myeloma," Blood, Nov. 2005, p. 446A, vol. 106, No. 11, Abstract.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, 2007, vol. 282, No. 29, pp. 21337-21348.
McManus, M. T., "MicroRNAs and Cancer," Seminars in Cancer Biology, 2003, pp. 253-258, vol. 13.
Medina, et al., MicroRNA's 221 and 222 Bypass Quiescence and Compromise Cell Survival Cancer Research, 2008, vol. 68, pp. 2773-2780.
Medina, P.P. et al., "OncomiR Addiction in an In Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of MicroRNA-21-Induced Pre-B-Cell Lymphoma," Supplementary Information, Sep. 2010, p. 1-22.
Megraw, M. et al., "miRGen: A Database for the Study of Animal MicroRNA Genomic Organization and Function," Nucleic Acids Research, 2007, pp. D149-D155, vol. 35.
Mendell, J.T., "miRiad Roles for the miR-17-92 Cluster in Development and Disease," Cell, 2008, pp. 217.
Meng, F. et al., "MicroRNA-21 Regulates Expression of the PTEN Tumor Suppressor Gene in Human Hepatocellular Cancer," Gastroenterology, 2007, pp. 647-658, vol. 133.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mercatelli, et al., The Inhibition of the Highly Expressed Mir-221 and Mir-222 Impairs the Growth of Prostate Carcinoma Xenografts in Mice, Plos One, 2008, vol. 3, No. 12, pp. 21337-21348.
Metzler, et al., High Expression of Precursor MicroRNA-155/BIC RNA in Children with Burkitt Lymphoma, Genes, Chromosomes, Cancer, 2004, vol. 39, 2, pp. 167-169.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mishra, A. et al., "Cancer Biomarkers: Are We Ready for the Prime Time?" Cancers, 2010, pp. 190-208, vol. 2.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mizusawa, et al., Differentiation phenotypes of pancreatic islet h- and a-cells are closely related with homeotic genes and a group of differentially expressed genes, Gene 2004, vol. 331, pp. 53, 63.
Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.
Mueller, J. et al., "Comprehensive Molecular Analysis of Mismatch Repair Gene Defects in Suspected Lynch Syndrome (Hereditary Nonpoluposis Colorectal Cancer) Cases," Cancer Research, 2009, pp. 7053-7061, vol. 69, No. 17.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.

(56) References Cited

OTHER PUBLICATIONS

Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
Nakamura, et al., ALL-1 Is a Histone Methyltransferase that Assembles a Supercomplex of Proteins Involved in Transcriptional Regulation, Mol. Cell, 10, 2002, pp. 1119-1128.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Nam, E.J. et al., "MicroRNA Expression Profiles in Serous Ovarian Carcinoma," Clinical Cancer Research, 2008, pp. 2690-2695, vol. 14, No. 9.
Nana-Sinkam, et al., Clinical applications for microRNA's in cancer, Nature, 2013, vol. 93.
Nazarov, et al., Interplay of microRNAs, transcription factors and target genes: linking dynamic expression changes to function, Nucleic Acids Research, 2013, vol. 41, No. 5, pp. 2817-2831.
Negrini, M. et al., "MicroRNAs in Human Cancer: From Research to Therapy," Journal of Cell Science, Apr. 2007, pp. 1833-1840, vol. 120.
Nicoloso, M.S. et al., "MicroRNAs—The Micro Steering Wheel of Tumour Metastases," Nature Reviews: Cancer, Apr. 2009, pp. 293-302, vol. 9.
Nippon—Journal of the Japanese Society, 1993, vol. 82, pp. 1053-1057.
Nurden, A.T., "Qualitative Disorders of Platelets and Megakaryocytes," Journal of Thrombosis and Haemostasis, 2005, vol. 3, pp. 1773-1782.
O'Connell, R. et al., "Inositol Phosphatase SHIP1 is a Primary Target of miR-155," PNAS, Apr. 2009, pp. 7113-7118, vol. 106, No. 17.
O'Donnell, c-Myc-regulated microRNAs modulate E2F1 expression, Nature, 2005, pp. 839-843.
Okada, H. et al., "MicroRNAs in Immune Regulation—Opportunities for Cancer Immunotherapy," The International Journal of Biochemistry & Cell Biology, 2010, pp. 1256-1261, vol. 42.
Okuda, et al., Natural History of Hepatocellular Carcinoma and Prognosis in Relation to Treatment, Cancer, 1985, vol. 56, 4, pp. 918-928.
Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Palamarchuk, A. et al., "Akt Phosphorylates Tcl1 Oncoprotein and Inhibits Its Repressor Activity," Cancer Research, Jun. 2005, pp. 4515-4519, vol. 65, No. 11.
Pallante, et al., MicroRNA deregulation in human thyroid papillary carcinomas, Endocr. Relat. Cancer, 2006, vol. 13, 2, pp. 497-508.
Pan, M. R. et al. Non-Steroidal Anti-Inflammatory Drugs Suppress the ERK, Cellular Signaling, 20, 2008, pp. 1134-1141.
Panarelli, et al., MicroRNA Expression Aids the Preoperative Diagnosis of Pancreatic Ductal Adenocarcinoma, Pancreas, 2012, vol. 41, pp. 685-690.
Papageorgiou, et al., Interferon-α Induces TRAIL Expression and Cell Death via an IRF-1-Dependent Mechanism in Human Bladder Cancer Cells, Cancer Biol Ther, 2007, vol. 6, No. 6, pp. 872-879.
Park, et al., Antisense inhibition of microRNA-21 or -221 arrests cell cycle, induces apoptosis, and sensitizes the effects of gemcitabine in pancreatic adenocarcinoma, Pancreas, 2009, Abstract.
Park, J.-K. et al., "miR-221 Silencing Blocks Hepatocellular Carcinoma and Promotes Survival," Cancer Research, Dec. 2011, pp. 7608-7616, vol. 71, No. 24.
Parkin, et al., Global Cancer Statistics, 2002, CA, Cancer, J. Clin., 2005, vol. 55, 2, pp. 74-108.
Partha, D. et al., "Early Detection of Ovarian Cancer," Biomark Med., Jun. 2008, vol. 2, No. 3, pp. 291-303.
Pasquinelli, et al., MicroRNAs: a developing story, Current Opinion in Genetics and Development, vol. 15, 2005, pp. 200-205.
Pathi, S. S., et al., GT-094, a No-NSAID, Inhibits Colon, Molecular Cancer Research, 2011, vol. 9, pp. 195-202.
Pawelczyk, T. et al., "Expression in *Escherichia coli* and Simple Purification of Human Fhit Protein," Protein Expr. Purlf., Apr. 2000, pp. 320-326, vol. 18, No. 3.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Animal Models for Chronic Lymphocytic Leumekia," Journal of Cellular Biochemistry, 2007, pp. 1109-1118, vol. 100.
Petrocca, F. et al., "MicroRNAs Deregulation in Gastric Cancer," PNAS, Apr. 2006, p. 1338, vol. 47, Abstract # 5690.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.
Pichiorri, F. et al., "MicroRNAs Regulate Critical Genes Associated with Multiple Myeloma Pathogenesis," PNAS, Sep. 2008, pp. 12885-12890, vol. 105, No. 35.
Pichiorri, F. et al., "MicroRNA Signatures in Multiple Myeloma," 99th AACR Annual Meeting, Apr. 12-16, 2008, pp. 1203, vol. 49, Abstract.
Pineau, P. et al., "miR-221 Overexpression Contributes to Liver Tumorigenesis," PNAS, Jan. 2010, pp. 264-269, vol. 107, No. 1.
Poliseno, et al., MicroRNAs modulate the angiogenic properties of HUVECs, Blood.
Porkka, K.P. et al., "MicroRNA Expression Profiling in Prostate Cancer," Cancer Research, 2007, pp. 6130-6135, vol. 67, No. 13.
Pouponnot, C. et al., "Cell Context Reveals a Dual Role for Maf in Oncogenesis," Oncogene, 2006, pp. 1299-1310, vol. 25.
Poy, et al., A pancreatic islet-specific microRNA regulates insulin secretion, Nature, 2004, vol. 432, pp. 226-230.
Prueitt, R. L. et al., "Expression of MicroRNAs and Protein-Coding Genes Associated with Perineural Invasion in Prostate Cancer," The Prostate, 2008, pp. 1152-1164, vol. 68.
Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.
Pu, et al., Circulating miR-221 directly amplified from plasma is a potential diagnostic and prognostic marker of colorectal cancer and is correlated with p53 expression, J. Gastroenterol Hepatol, 2010, vol. 25, pp. 1674-1680.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Ren, et al., Co-delivery of as-miR-21 and 5-FU by Poly (amidoamine) Dendrimer Attenuates Human Glioma Cell Growth in Vitro, Journal of Biomedical Science, 2010, vol. 21, pp. 303-314.
Resnick, et al., The detection of differentially expressed microRNAs from the serum of ovarian cancer patients using a novel real-time PCR platform, Gynecologic Oncology, 2009, vol. 112, pp. 55-59.
Ribas, J. et al., "The Transcriptional Regulation of miR-21, Its Multiple Transcripts, and Their Implication in Prostate Cancer," Cell Cycle, 2010, pp. 923-929, vol. 9.

(56) References Cited

OTHER PUBLICATIONS

Rockerfeller, Science Daily, Web address: http://www.sciencedaily.com/release/2009/05/090522171001.html Nov. 2013.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rosa, et al., The miR-430/427/302 Family Controls Mesendodermal Fate Specification via Species-Specific Target Selection, Developmental Cell, 16, 2009, pp. 517-527.
Rossi, et al., Modification of MiR gene expression pattern in human colon cancer cells following exposure to 5-fluorouracil in vitro, Pharmacological Research, Academic Press, Londdon, GB, vol. 56, No. 3, Aug. 30, 2007, pp. 248-253.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Rozovskaia, T. et al., "Expression Profiles of Acute Lymphoblastic and Myeloblastic Leukemias with All-1 Rearrangements," PNAS, Jun. 2003, pp. 7853-7858, vol. 100, No. 13.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Sah., et al, Translation Inhibitors Sensitize Prostate Cancer Cells to Apoptosis Induced by Tumor Necrosis Factor-related Apoptosis-inducing Ligand (TRAIL) by Activating c-Jun N-terminal Kinase, J. Biol Chem 2003, vol. 278, pp. 20593-20602.
Saini, H. K. et al., "Annotation of Mammalian Primary MicroRNAs," BMC Genomics, 2008, vol. 9.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Salovaara, R. et al., "Population-Based Molecular Detection of Hereditary Nonpolyposis Colorectal Cancer," Journal of Clinical Oncology, Jun. 2000, pp. 2193-2200, vol. 18, No. 11.
Santanam, U. et al., "Chronic Lymphocytic Leukemia Modeled in Mouse by Targeted miR-29 Expression," PNAS, Jul. 2010, pp. 12210-12215, vol. 107, No. 27.
Sarver, A.L. et al., "Human Colon Cancer Profiles Show Differential microRNA Expression Depending on Mismatch Repair Status and are Characteristic of Undifferentiated Proliferative States," BMC Cancer, 2009, pp. 1-15, vol. 9. No. 401.
Sasaki, Y.T.F. et al., "Coordinated Expression of ncRNAs and HOX mRNAs in the Human HOXA Locus," Biochemical and Biophysical Research Communications, 2007, pp. 724-730, vol. 357.
Schagen, F. et al., "Genetic Targeting of Adenovirus Vectors Using a Reovirus Sigmal-Based Attachment Protein," Molecular Therapy, May 2006, pp. 997-1005, vol. 13, No. 5.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.
Schmittgen, T. D. et al., "A High-Throughput Method to Monitor the Expression of MicroRNA Precursors," Nucleic Acids Research, Feb. 2004, vol. 32, No. 4.
Schrump, et al.,Targeting the Epigenome for the Treatment and Prevention of Lung Cancer Semin Oncol, 32, 2005, pp. 488-502.
Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.
Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.
Selvendiran, K. et al. NCX-4016 a Nitro-derivative of Aspirin, Cell Cycle, 2008, 7:1, pp. 81-88.

Seth, P., "Vector-Mediated Cancer Gene Therapy," Cancer Biology & Therapy, May 2005, pp. 512-517, vol. 4, Issue 5.
Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.
Sharma, S. et al., "Development of Inhalational Agents for Oncologic Use," Journal of Clinical Oncology, Mar. 2001, Abstract, vol. 19, Issue 6.
Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.
Shih, K.K. et al., "Exosomal MicroRNAs Step into the Biomarker Arena," Gynecologic Oncology, Jul. 2008, pp. 1-2, vol. 110, No. 1.
Skalsky, R.L. et al., "Kaposi's Sarcoma-Associated Herpesvirus Encodes an Ortholog of miR-155," Journal of Virology, Dec. 2007, pp. 12836-12845, vol. 81, No. 23.
Slaby, et al., AlteredExpressionofmiR21-miR31, Oncology, 2007, vol. 72, pp. 1-6.
Slack, F.J., "Big Roles for Small RNAs," Nature, Feb. 2010, p. 616, vol. 463.
Sonoki, T. et al., "Insertion of MicroRNA-125b-1, A Human Homologue of lin-4, into a Rearranged Immunoglobulin Heavy Chain Gene Locus in a Patient with Precursor B-Cell Acute Lymphoblastic Leukemia," Leukemia, 2005, pp. 1-2, vol. 19.
Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.
Stenvang, et al., "The utility of LNA in microRNA-based cancer diagnostics and therapeutics", Seminars in Cancer Biology, 2008, pp. 89-102.
Suarez-Saiz, F.J. et al., "MicroRNA Expression Profiling in Acute Myelogenous Leukemia," Canada Blood, Nov. 2004, Abstract #1131, p. 320A.
Sugito, et al., RNASEN regulates Cell Proliferation and Affects Survival in Esophageal Cancer Patients, Clin Canc Res, 2006[1], vol. 12, pp. 7322-7328.
Suh, et al., Human embryonic stem cells express a unique set of microRNAs, Dev. Biol., 270, 2004, pp. 488-498.
Sun Kai, Analysis of microRNA expression patterns, Chinese Journal of Experimental Surgery, 2006, vol. 23, No. 8, pp. 945-947.
Sun, et al., MicroRNA-221 inhibits CDKN1C/p57 expression in human colorectal carcinoma, Acta Pharmacologica Sinica, 2011, vol. 32, pp. 375-384.
Suzuki, et al., RNA Interference-Mediated Knockdown of DNA Methyltransferase 1 Leads to Promoter Demethylation and Gene Re-Expression in Human Lung and Breast Cancer CellsCancer, Research, 64, 2004, pp. 3137-3143.
Szymanski M., et al., "A new frontier for molecular medicine: Noncoding RNAs", Biochimicae & Biophysica Acta, vol. 1756, No. 1, Sep. 25, 2005, pp. 65-75.
Taccioli, C. et al., "Ucbase & miRfunc: A Database of Ultraconserved Sequences and MicroRNA Function," Nucleic Acids Research, 2009, pp. D41-D48, vol. 37.
Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.
Tam, The Emergent Role of MicroRNA's in Molecular Diagnostics of Cancer, Journal of Molecular Diagnostics, 2008, vol. 10, pp. 411-414.
Tang, X. et al., "A Simple Array Platform for MicroRNA Analysis and Its Application in Mouse Tissues," RNA, Aug. 2007, pp. 1-20, vol. 13.
Tanner et al., BAALC, the human member of a novel mammalian neuroectoderm gene lineage, is implicated in hematopoiesis and acute leukemia, PNAS, Nov. 20, 2001, vol. 98, No. 24, pp. 13901-13906.
Tanzer, Molecular Evolution of a MicroRNA Cluster, J. Mol. Biol, 2004, vol. 339, 2, pp. 327-335.
Tatsuya, et al., Oncogenic All1 fusion proteins target Drosha-mediated microRNA processing, PNAS, 2007, vol. 104, pp. 10980-10985.

(56) References Cited

OTHER PUBLICATIONS

Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Teachey, et al., Mammalian target of rapamycin inhibitors and their potential role in therapy in leukemia and other haematogical malignancies, British Journal of Haematology, 2009[1], vol. 145, pp. 569-580.
Thomson, et al., Extensive post-transcriptional regulation of microRNAs and its implications for cancer Genes, Dev. 20, 2006, pp. 2202-2207.
Thomson, J. M. et al., "A Custom Microarray Platform for Analysis of MicroRNA Gene Expression," Nature Methods, Oct. 2004, pp. 1-7, vol. 1, No. 1.
Thomson, M., Supplementary data for "A Custon Microarray Platform for Analysis of MicroRNA Gene Expression," Nature Methods, Oct. 2004, pp. 47-53, vol. 1, No. 1.
Thorgeirsson, et al., Molecular pathogenesis of human hepatocellular carcinoma, Nat, Genet. 2002, vol. 31, 4, pp. 339-346.
Thorgeirsson, S. S. et al., "Functional Genomics of Hepatocellular Carcinoma," Hepatology, Feb. 2006, pp. S145-S150, vol. 43, No. 2, Suppl. 1.
Tibshirani, et al., Diagnosis of multiple cancer types by shrunken centroids of gene expression, PNAS, 2002, vol. 99, 10, pp. 6567-6572.
Tili, E. et al., "Expression and Function of Micro RNAs in Immune Cells During Normal or Disease State," International Journal of Medicine Sciences, 2008, pp. 73-79, vol. 5, No. 2.
Tili, E. et al., "Mutator Activity Induced by microRNA-155 (miR-155) Links Inflammation and Cancer," PNAS, Mar. 2011, pp. 4908-4913, vol. 108, No. 12.
Tkachuk, et al., Involvement of a Homolog of *Drosophila* Trithorax by 11 q23 Chromosomal Translocations in Acute Leukemias Cell, vol. 71, 1992, pp. 691-700.
Tockman, M. S. et al., "Considerations in Bringing a Cancer Biomarker to Clinical Application," Cancer Research, May 1992, pp. 2711s-2718s, vol. 52.
Tokarz, et al., The Role of microRNA in metastatic colorectal cancer and its significance in cancer prognosis and treatment, Acta Biochimica Polonica, 2012, vol. 59, pp. 467-474.
Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.
Tricoli, J. V. et al., "MicroRNA: Potential for Cancer Detection, Diagnosis, and Prognosis," Cancer Research, May 2007, pp. 4553-4555, vol. 67, No. 10.
Tsunoda, et al., Oncogenic KRAS regulates miR-200c and miR-221, 222 in a 3D-specific manner in colorectal cancer cells, Anticancer Research, 2011, Abstract.
Tusher, et al., Significance analysis of microarrays applied to the ionizing radiation response, PNAS, 2001, vol. 98, 9, pp. 5116-5121.
Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.
Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.
Ulivi, et al., p16INK4A and CDH13 Hypermethylation in Tumor and Serum of Non-Small Cell Lung Cancer Patients Journal of Cell, Physiol, 206, 2006, pp. 611-615.
Valeri, et al., MicroRNA-21 induces resistance to 5-fluorouracil by down-regulating human DNA MutS homolog 2 hMSH2 ,PNAS, 2010, vol. 107, No. 49, pp. 21098-21103.
Valeri, N. et al., "Pathogenetic and Clinical Relevance of microRNAs in Colorectal Cancer," Cancer Genomics Proteomics, Jul./Aug. 2009, pp. 195-204, vol. 6, No. 4.
Valeri, N. et al., "Modulation of Mismatch Repair and Genomic Stability by miR-155," PNAS, Apr. 2010, pp. 6982-6987, vol. 107, No. 15.
Valeri, N. et al., "Epigenetics, miRNAs, and Human Cancer: A New Chapter in Human Gene Regulation," Mamm Genome, Aug. 2009, pp. 573-580, vol. 20.
Vandeneynde, et al., Is Tailored Adjuvant Treatment for Colon Cancer Possible, Clinical Colorectal Cancer, 2010, vol. 9, pp. 15-21.
Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.
Varotti, et al., Comparison between the fifth and sixth editions of the AJCC/UICC TNM staging systems for hepatocellular carcinoma: multicentric study on 393 cirrhotic resected patients, Eur. J. Surg. Oncol, 2005, vol. 31, 7, pp. 760-767.
Vassilev et al., "Small-Molecule Antagonists of p53-MDM2 Binding," Cell Cycle, 2004, vol. 3, No. 4, pp. 419-421.
Vatolin, et al., A Novel Method to Detect Functional MicroRNA Targets, J. Mol. Biol., 358, 2006, pp. 983-996.
Verschuur, A.C., "Acute Megakaryoblastic Leukemia," May 2004, pp. 1-5, Retrieved from the Internet: URL: http://www.orpga.net/data/patho/GB/uk-AMLM7.pdf.
Virgilio, L. et al., "Identification of the TCL1 Gene Involved in T-Call Malignancies," Proc. Natl. Acad. Sci., Dec. 1994, pp. 12530-12534, vol. 91.
Visone, R. et al., "MiRNAs and Cancer," The American Journal of Pathology, Apr. 2009, pp. 1131-1138, vol. 174, No. 4.
Volinia, et al., "Reprogramming of MirRNA Networks in Cancer and Leukemia," Genome Research, 2010, pp. 589-599, vol. 20.
Volinia, et al., Breast cancer signatures for invasiveness and prognosis defined by deep sequencing of microRNA, PNAS, Feb. 21, 2012, vol. 109, No. 8, pp. 3024-3029.
Volinia, Prognostic microRNA/mRNA signature from the integrated analysis of patients with invasive breast cancer, PNAS, 2013, pp. 1-5.
Volinia, S. et al., "A MicroRNA Expression Signature of Human Solid Tumors Defines Cancer Gene Targets," PNAS, Feb. 2006, pp. 2257-2261, vol. 103, No. 7.
Wang, E. et al., "Ontogeny and Oncogenesis Balance the Transcriptional Profile of Renal Cell Cancer," Cancer Research, Oct. 2004, pp. 7279-7287, vol. 64.
Wang, X. et al., "Association Between CpG Island Methylation of the WWOX Gene and Its Expression in Breast Cancers," Tumor Biology, Feb. 2009, pp. 8-14, vol. 30.
Watson, D.I. et al., "MicroRNA Expression Profiles in Barrett's Oesophagus," RACS Annual Scientific Congress, 2007, pp. A45, vol. 77.
Weidhaas, J., "Using MicroRNAs to Understand Cancer Biology," Published Online Dec. 21, 2009, www.thelancet.com/oncology, DOI: 10.1016/S1470-2045(09)70386-9.
Wiemer et al., "The Role of MicroRNAs in Cancer: No Small Matter," European Journal of Cancer, Jun. 12, 2007, vol. 43, No. 10, pp. 1529-1544.
Wijermans, P.W., "Low Dose Azanucleosidesfor High Risk (s) MDS and AML," Haematologica Reports,Nov. 2006, pp. 74-76. vol. 2, Issue, 15.
Wildi, et al., Critical evaluation of the different staging systems for hepatocellular carcinoma, Br. J. Surg., 2004, vol. 91, 4, pp. 400-408.
Wu, D. et al., "Lenalidomide Enhances natural Killer Cell and Monocyte-Mediated Antibody-Dependent Cellular Cytotoxicity of Rituximab-Treated CD20+ Tumor Cells," Clin. Cancer Res., 2008, vol. 14, No. 14, pp. 4650-4657.
Xi, Y. et al., "Prognostic Values of MicroRNAs in Colorectal Cancer," Biomarker Insights, Jan. 2006, pp. 113-121, vol. 1.
Yamamichi, et al., Locked Nucleic Acid In Situ Hybridization Analysis of MiR-21 Expression during Colorectal Cancer Development, Clinical Cancer Research, vol. 15, No. 12, Jun. 15, 2009, pp. 4009-4016.
Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.
Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

(56) References Cited

OTHER PUBLICATIONS

Yanaihara, N. et al., "Unique MicroRNA Molecular Profiles in Lung Cancer Diagnosis and Prognosis," Cancer Cell, Mar. 2006, pp. 189-198, vol. 9.
Yang, J. et al., "Analysis of Sequence Variations in 59 MicroRNAs in Hepatocellular Carcinomas," Mutation Research, Aug. 2008, pp. 205-209, vol. 638.
Ye, et al., Predicting hepatitis B virus-positive metastatic hepatocellular carcinomas using gene expression profiling and supervised machine learning, Nat. Med., 2003, vol. 9, 4, pp. 416-423.
Yekta, et al., MicroRNA-Directed Cleavage of HOXB8 MRNA, Science, 2004, vol. 304, pp. 594-596.
Yendamuri, S. et al., "WW Domain Containing Oxidoreductase Gene Expression is Altered in Non-Small Cell Lung Cancer," Cancer Research, Feb. 2003, pp. 878-881, vol. 63.
Yi, et al., Exportin-5 mediates the nuclear export of pre-microRNAs and short hairpin RNAs, Genes Dev, 2003, vol. 17, 24, pp. 3011-3016.
Yoo, et al., Epigenetic therapy of cancer: past, present and future, Nature Reviews Drug Discov 5, 2006, pp. 37-50.
Yoon, S. et al., "Prediction of Regulatory Modules Comprising MicroRNAs and Target Genes," Bioinformatics Genes and Genomes, 2005. pp. ii93-ii100, vol. 21, Suppl. 2.
Yu, et al., Context-Dependent Bidirectional Regulation of the MutS Homolog 2 by Transforming Growth Factor Contributes to Chemoresistance in Breast Cancer Cells, Molecular Cancer Research, vol. 8, No. 12, Oct. 14, 2010, pp. 1633-1642.
Yu, et al., Human microRNA clusters: Genomic organization and expression profile in leukemia cell lines, Biomed Biophys Res Comm, 2006, pp. 59-68.
Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.
Yuki, et al., Growth and Spread of Hepatocellular Carcinoma, Cancer, 1990, vol. 66, 10, pp. 2174-2179.
Zaman, et al., Current status and implications of microRNAs in ovarian cancer diagnosis and therapy, J Ovarian Res, 2012[1].
Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX," Biotechnology Letters, Jun. 2007, pp. 877-883, vol. 29, No. 6.
Zeng, Y. et al., "Recognition and Cleavage of Primary MicroRNA Precursors by the Nuclear Processing Enzyme Drosha," The EMBO Journal, 2005, pp. 138-148, vol. 24.
Zhang, et al., Inhibitory effect of knocking down microRNA-221 and microRNA-222 on glioma cell growth in vitro and in vivo, Chinese Journal of Oncology, 2009, vol. 31, No. 10.
Zhang, In Vitro Study on effect of up-regulation of PETN expression by miR-221 and miR-222 knocked-down in lung cancer cell line A549 cells on radiosensitization, Proceedings of the 5th Chinese Academic Conf. on Tumors, the 7th Academic Conf. on Tumors Across the Taiwan Straits, Academic Conf. on Int'l Tumor Cells and Gene Therapy, and the 2nd Chinese and Japanese Academic Conf. on Tumor Interventional Therapy, p. 317, 2008.
Zhang, In vitro study on effect of up-regulation of TIMP3 expression by antisense miR-221 and miR-222 on inhibition of invasiveness of glioblastoma cell U251, The 8th Conference and Symposium Proceedings, China Genetic Association, 2004-2008, p. 139.
Zhang, L. et al., "Genomic and Epigenetic Alterations Deregulate MicroRNA Expression in Human Epithelial Ovarian Cancer," PNAS, May 2008, pp. 7004-7009, vol. 105, No. 19.
Zhang, L. et al., "MicroRNAs Exhibit High Frequency Genomic Alterations in Human Cancer," PNAS, Jun. 2006, pp. 9136-9141, vol. 103, No. 24.
Zhang, L. et al., Supporting Information, PNAS 2008, pp. 1-11.
Zhang, Z. et al., "Three Biomarkers Identified from Serum Proteomic Analysis for the Detection of Early Stage Ovarian Cancer," Cancer Research, Aug. 2004, pp. 5882-5890, vol. 64.
Zhao et al., "p53 Mediates the Negative Regulation of MDM2 by Orphan Receptor TR3," The EMBO Journal, 2006, pp. 5703-5715, vol. 25.
Zhou, et al., Binding of NF-kappaB p65 subunit to the promoter elements is involved in LPS-induced transactivation of miRNA genes in human biliary epithelial cells, Nucleic Acids Research, 2010, vol. 38, No. 10, pp. 3222-3232 [1].
Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

\* cited by examiner

```
                        SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cagaaagccc tggaacttga                                                 20

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttccatagt gttaactgtc agtgc                                           25

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cccagtaatg gaatgaaggg tctgtaatag ttttatattg                           40

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaatgttgct gtgcgccta                                                  19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaatgttgct gtgcgccta                                                  19

<210> SEQ ID NO 6
<211> LENGTH: 21
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 6
tcaattgcaa acagtcctca g                                                  21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcaattgcaa acagtcctca g                                                  21

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caatataaaa ctattacaga cccttcattc cattactggg                              40

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tagcttttcc tcccccattt                                                    20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccacctttgt cagaagtcaa ctc                                                23

<210> SEQ ID NO 11
<211> LENGTH: 26
<212> TYPE: RNA
<213> ORGANISM: Homo sapiens

<400> SEQUENCE: 11
gaaugaaggu aauauugaua agcuau                                             26

<210> SEQ ID NO 12
<211> LENGTH: 22
<212> TYPE: RNA
<213> ORGANISM: Homo sapiens

<400> SEQUENCE: 12
```

```
uagcuuauca gacugauguu ga                                              22

<210> SEQ ID NO 13
<211> LENGTH: 24
<212> TYPE: RNA
<213> ORGANISM: Homo sapiens

<400> SEQUENCE: 13
acaacauuau gaucuaauaa acuu                                            24

<210> SEQ ID NO 14
<211> LENGTH: 22
<212> TYPE: RNA
<213> ORGANISM: Homo sapiens

<400> SEQUENCE: 14
uagcuuauca gacugauguu ga                                              22
```

MATERIALS AND METHODS RELATED TO MICRORNA-21, MISMATCH REPAIR, AND COLORECTAL CANCER

CROSS-REFERENCE TO RELATED APPLICATIONS

This application is the United States National Stage Entry of International Application PCT/US2011/060349, filed Nov. 11, 2011, which claims the benefit of United States Provisional Application 61/413,180, filed Nov. 12, 2010. Each aforementioned application is incorporated herein by reference for all purposes.

SEQUENCE LISTING

The instant application contains a Sequence Listing which has been submitted in ASCII format via EFS-Web and is hereby incorporated by reference in its entirety. Said ASCII copy, created on Nov. 7, 2011, is named 53-52535_SEQ_LIST_OSURF 11085.txt and is 3,139 bytes in size.

FIELD OF THE INVENTION

This invention relates generally to the field of molecular biology. More particularly, it concerns cancer-related technology. Certain aspects of the invention include application in diagnostics, therapeutics, and prognostics of miR-21-associated colorectal cancers. In particular miR21, mismatch repair, and colorectal cancer are discussed herein.

BACKGROUND OF THE INVENTION

Colorectal cancer (CRC) is one of the most frequently occurring cancers in the U.S., with more than 140,000 new cases and about 50,000 deaths expected to occur in 201. 5-fluorouracil (5-FU) based chemotherapy represents the gold standard for CRC treatment both in the adjuvant and metastatic setting. However, primary or acquired resistance to pyrimidine analog treatments represents a common problem in the management of CRC patients. These observations highlight the need for a better understanding of resistance mechanisms and more effective therapies.

MicroRNAs are a class of small non-coding RNAs that act as post-transcriptional regulators of gene expression and cell homeostasis. Over-expression of miR-21 is a common trait of many solid and hematological malignancies. miR-21 over-expression has been found in blood and stool samples from patients affected by CRC. Moreover, miR-21 over-expression is associated with poor benefit from 5-FU adjuvant chemotherapy in stage II and III CRC.

The Mismatch Repair (MMR) System is involved in DNA damage recognition and repair. hMSH2 and hMLH1 function as core MMR proteins and form heterodimers with protein homologs hMSH3 or hMSH6 and hMLH3 or hPMS2 respectively. Heterodimer formation is fundamental for the DNA damage recognition and represents a crucial step for the stability of the MMR protein homologs. Defects in MMR proteins have been associated with reduced or absent benefit from 5-FU adjuvant chemotherapy in clinical trials. MMR impairment appears to cause reduced incorporation of 5-FU metabolites into DNA leading to reduced G2/M arrest and apoptosis after 5-FU treatment.

The over-expression of miR-21 is linked to a number of human tumors including colorectal cancer, where it appears to regulate the expression of tumor suppressor genes including p21, PTEN, TGFβRII and Bax.

SUMMARY OF THE INVENTION

The present invention demonstrates that miR-21 targets and down-regulates the core mismatch repair (MMR) recognition protein complex hMSH2 and hMSH6. Colorectal tumors that express a high level of miR-21 display reduced hMSH2 protein expression. Cells that overproduce miR-21 exhibit significantly reduced 5-fluorouracil (5-FU) induced G2/M damage arrest and apoptosis that is characteristic of defects in the core MMR component. Moreover, xenograft studies demonstrate that miR-21 over-expression dramatically reduces the therapeutic efficacy of 5-FU. The present studies show that MMR mutator gene down-regulation associated with miR-21 over-expression may be an important clinical indicator of therapeutic efficacy in colorectal cancer.

The present invention provides compositions of matter comprising at least one anti-sense miRNA and at least one additional composition, wherein the anti-sense miRNA is miR-21 and is capable of downregulating at least one core MMR protein, and wherein the at least one additional composition is useful to treat MMR-related disease. Preferably, the at least one additional composition is selected from the group consisting of: a chemotherapy drug; a stem cell; AG1478; gefitinib (Iressa); erlotinib (Tarceva); cetuximab; panitumab; zalutumamab; nimotuzamab; matuzumab; and lapatinib. Preferably, the at last one core MMR protein is selected from the group consisting of: hMSH1; hMSH6; and hMLH1.

The present invention therefore provides compositions of matter comprising antisense miR-21 and 5-fluorouracil, or pharmaceutically-acceptable formulations thereof.

Also provided are compositions of matter, comprising antisense miR-21 and means to increase human MutS homolog 2, or pharmaceutically-acceptable formulations thereof.

Also provided are compositions of matter comprising antisense miR-21 and a colorectal cancer treatment compound, or pharmaceutically-acceptable formulations thereof.

Also provided are compositions of matter comprising sense or antisense miR-21 and a pyrimidine analog.

Also provided are compositions of matter wherein the pyrimidine analog is 5-fluororouracil.

The present invention provides kits comprising a composition of claim 4.

Also provided are which further comprises means for identifying hMSH2 expression status.

Also provided are kits wherein the means for identifying hMSH2 expression status is an antibody.

Also provided are kits which further comprise instructions for screening test compounds as potential colorectal cancer treatments.

The present invention provides methods to affect at least one human cell, comprising introducing to at least one hMutSH2-underexpressing cell an underexpression-decreasing amount of antisense miR-21.

Also provided are methods wherein the at least one hMutSH2-underexpressing cell is at least one colorectal cancer cell.

Also provided are methods wherein the at least one hMutSH2-underexpressing cell is present in vitro.

Also provided are methods wherein the at least one hMutSH2-underexpressing cell is present in situ.

Also provided are methods wherein the at least one hMutSH2-underexpressing cell is present in vivo.

Also provided are methods which result in apoptosis of the at least one hMutSH2-underexpressing cell.

Also provided are methods wherein the at least one hMutSH2-underexpressing cell is many cells that form a tumor.

Also provided are methods wherein the tumor is decreased in size after introduction of the antisense miR-21.

Also provided are methods which further comprise introducing 5-fluorouracil to the at least one hMutSH2-underexpressing cell.

Also provided are methods which further comprise introducing 5-fluorouracil to the at least one hMutSH2-underexpressing cell.

The present invention provides methods to treat a patient with primary or acquired pyrimidine analog-resistant colorectal cancer, comprising administering antisense miR-21 to a patient with primary or acquired pyrimidine analog-resistant colorectal cancer.

Also provided are methods wherein the patient has down-regulated hMSH2.

Also provided are methods which further comprise administering an additional colorectal cancer adjuvant or treatment to the patient.

Also provided are methods which further comprise administering 5-fluorouracil to the patient.

Also provided are methods to treat a patient with stage II or stage III colorectal cancer, comprising administering antisense miR-21 to a patient with stage II or stage III colorectal cancer.

Also provided are methods wherein the patient has down-regulated hMSH2.

Also provided are methods which further comprise administering an additional colorectal cancer adjuvant or treatment to the patient.

Also provided are methods which further comprise administering 5-fluorouracil to the patient.

The present invention provides methods to treat a patient with colorectal cancer, comprising: a.) identifying if a patient with colorectal cancer has decreased hMSH2 expression, and b.) treating the patient with antisense miR-21 if the patient has decreased hMSH2 expression.

The present invention provides methods to treat a patient with colorectal cancer, comprising: a.) identifying if a patient with colorectal cancer has decreased hMSH2 expression compared to control, and b.) treating the patient with antisense miR-21 if the patient has decreased hMSH2 expression.

The present invention provides methods to treat a patient with colorectal cancer, comprising: a.) identifying if a patient with colorectal cancer has decreased hMSH2 expression compared to control, b.) identifying if the patient with colorectal cancer has increased miR-21 expression compared to control, and c.) treating the patient with antisense miR-21 if the patient has increased miR-21 expression and decreased hMSH2 expression compared to control.

The present invention provides methods to identify useful compounds, comprising a.) introducing a test compound and antisense and/or sense miR-21 to hMSH2-expressing cells, and b.) identifying test compounds useful to affect hMSH2-expressing cells.

The present invention provides methods to identify cancer cell sample status, comprising: a.) correlating hMSH2 and miR-21 status in a cell test sample with control, and b.) identifying cancer cell sample status.

The present invention provides methods to predict colorectal cancer cell sample status, comprising: a.) correlating hMSH2 and miR-21 status in a colorectal cancer cell-containing test sample with control, and b.) predicting colorectal cancer cell sample status.

The present invention provides methods to identify organism cancer status, comprising: a.) correlating hMSH2 and miR-21 status in an organism-derived test sample with control, and b.) identifying organism status.

The present invention provides methods to predict organism colorectal cancer status, comprising: a.) correlating hMSH2 and miR-21 status in a organism-derived test sample with control, and b.) identifying organism colorectal cancer status.

The present invention provides methods to inhibit G2/M arrest and apoptosis in 5-fluorouracil-resistant colorectal cancer cells, comprising introducing to 5-fluorouracil-resistant colorectal cancer cells a G2/M arrest and apoptosis-inhibiting amount of antisense miR-21.

The present invention provides methods to inhibit inflammation in 5-fluorouracil-resistant colorectal cancer cells, comprising introducing to 5-fluorouracil-resistant colorectal cancer cells an inflammation-inhibiting amount of antisense miR-21.

Various aspects of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 1A: miR-21 (SEQ ID NOS 12 and 14, respectively) predicted seed regions in hMSH2 (SEQ ID NO: 11) and hMSH6 (SEQ ID NO: 13) 3' UTR are shown.

FIG. 1B: Colo-320DM and SW620 were transiently transfected with miR-21, scrambled-miR, siRNA anti-MSH2 or anti-MSH6 for 48 hours. hMSH2 and hMSH6 mRNA expression was analyzed by Real Time-PCR.

FIG. 1C: Western blotting analysis of miR-21 dependent down-regulation of both hMSH2 and hMSH6. Transfections were similar to (FIG. 1B).

FIG. 1D: HCT-116, SW480 and RKO that contain high endogenous levels of miR-21 cells were transfected with an LNA anti-miR-21 or anti-miR control for 48 hours followed by western blotting analysis of hMSH2 and hMSH6 protein.

FIG. 1E: hMSH2 and hMSH6 3' UTR were sub-cloned downstream of the luciferase genes (MSH2-Luc-WT and MSH6-Luc-WT respectively) as well as hMSH2 and hMSH6 3' UTR containing a deletion of the miR-21 target site (MSH2-Luc-mutant and MSH6-Luc-mutant) respectively and co-transfected with miR-21 or scrambled miR. Luciferase activity was recorded after 24 hours. The data represent the mean and S.D from at least 3 determinations from 4 independent transfections. *p<0.01.

FIG. 1F: SW480 cells were co-transfected with the hMSH2 and hMSH6 3'-UTR luciferase reporter plus the LNA anti-miR-21 or anti-miR control. LNA silencing of miR-21 induced an increase in luciferase activity.

FIG. 2A: Paraffin-embedded, formalin-fixed CRC tissues were incubated with an LNA-probe anti-miR-21 or scrambled probe as well as IHC antibody against hMSH2. Representative photographs were captured with the Nuance system software. CRC samples where staining was positive for both miR-21 and hMSH2 are shown. Blue and red staining identifies miR-21 and hMSH2 protein respectively.

SW620 and Colo-320DM cells were synchronized at G0-G1 by serum starvation for 48 hours. Cells were then trypsinized, counted, transfected with scrambled miR, miR-21, siRNA anti-MSH2 or siRNA-control, and re-plated in medium containing 10% FBS. 5-FU was added at 16 h after release, corresponding to a time just prior to entry into S phase but after the p53-mediated G1-S cell cycle checkpoint. Cell cycle was analyzed 48 hours after 5-FU administration. Quantitation of percentage of G2/M arrested and apoptotic (sub-G1) cells are shown and represent mean and S.D. from 3 determinations from 3 independent transfections. *p<0.001.

Figure 4A:
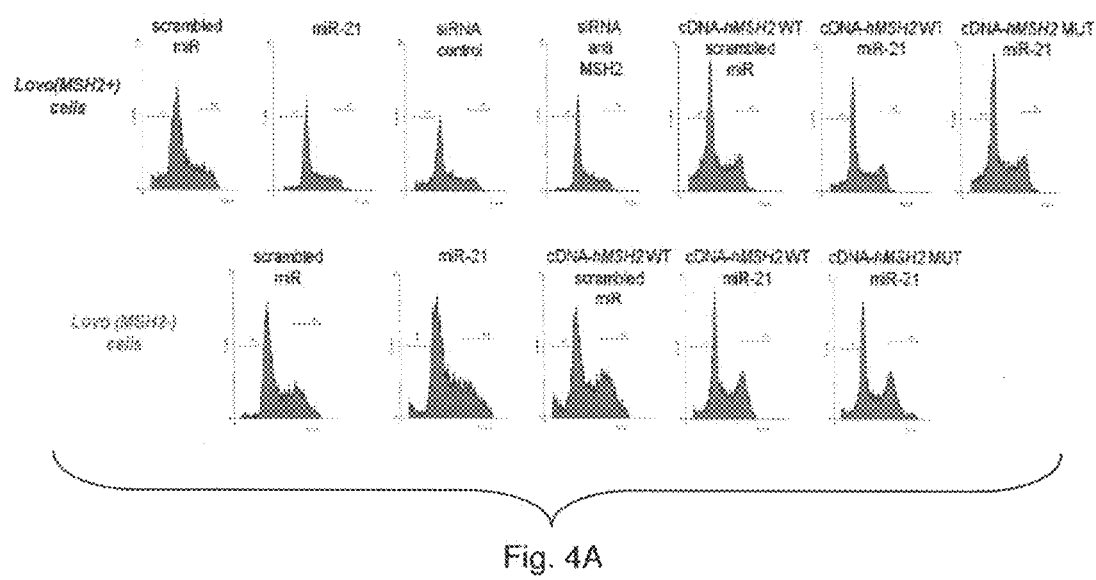
Figure 4B:
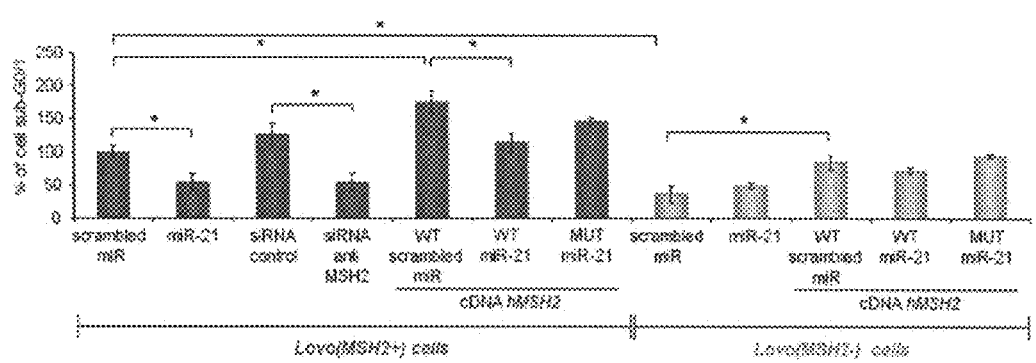
Figure 4C:
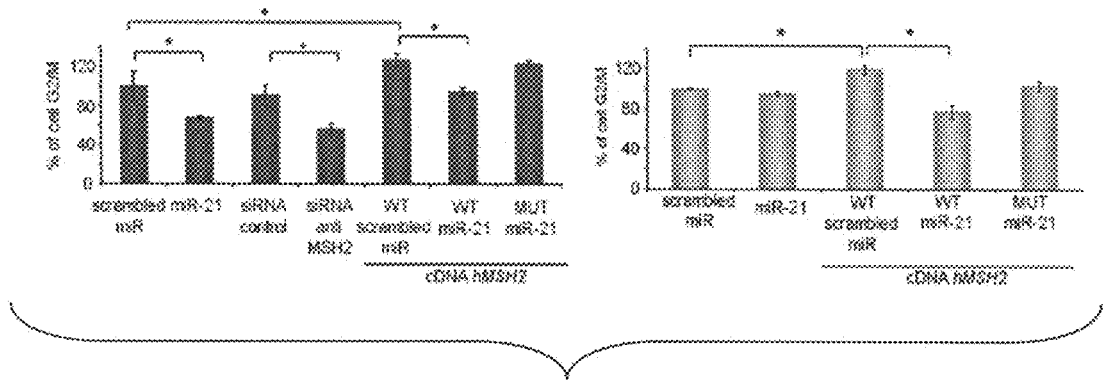

FIGS. 4A-4C. miR-21 mediated 5-FU resistance is dependent upon hMSH2 down-modulation.

Lovo(MSH2+) and Lovo(MSH2−) cells were synchronized at G0-G1 by serum starvation for 48 hours and transfected with miR-control, miR-21, siRNA anti-MSH2, siRNA-control, along with vectors encoding the full length hMSH2 cDNA (with or without miR-21 seed region). Cell cycle was analyzed 48 hours after 5-FU administration. Quantitation of percentage of G2M arrested and apoptotic (sub-G1) cells in both Lovo(MSH2+) cells (blue bars) and Lovo(MSH2−) cells (pink bars) are shown and represent mean and S.D. from 2 determinations from 3 independent experiments (*p<0.001).

Figure 5A:
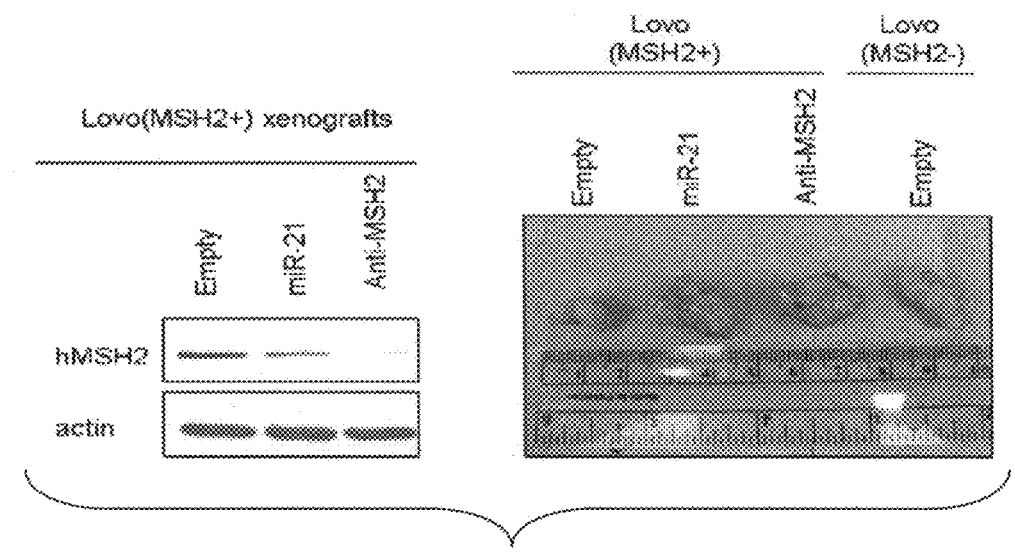
Figure 5B:
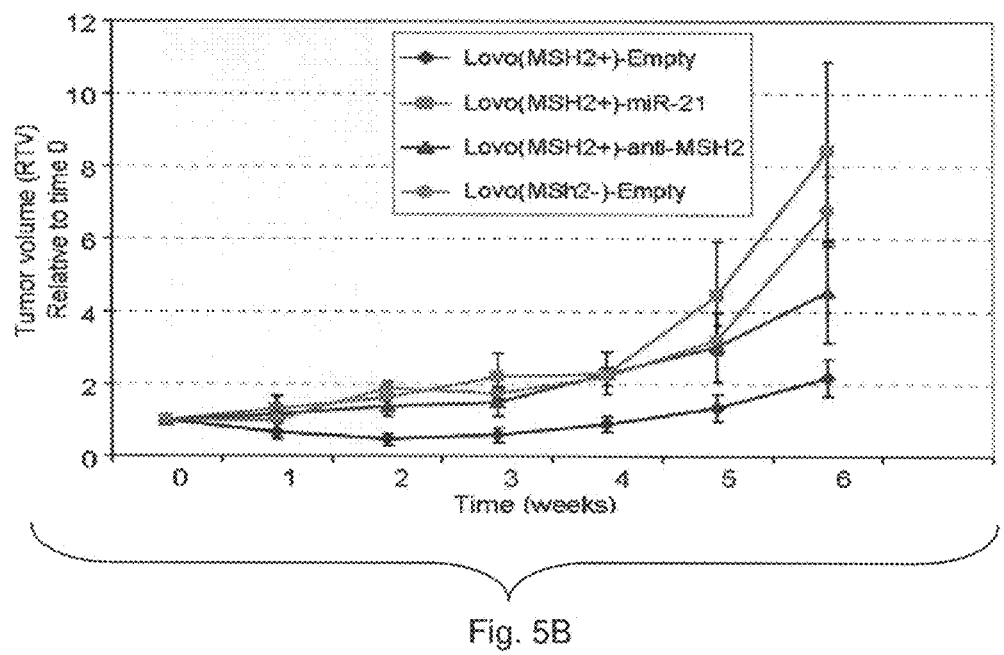

FIGS. 5A-5B: miR-21 causes resistance to 5-FU in vivo.

Lovo(MSH2+) cells were stably infected with a lentiviral vector encoding for either miR-21 or siRNA anti-MSH2. As a control, Lovo(MSH2+) and Lovo(MSH2−) cells were infected with empty vectors. Nude mice were injected with Lovo (MSH2+)-Empty (n=6), Lovo(MSH2+)-miR-21 (n=6), Lovo(MSH2+)-anti-MSH2(n=6) and Lovo(MSH2−)-Empty (n=6). When xenografts reached a palpable volume, 5-FU was administered by intraperitoneal injection for 5 consecutive days a week for 2 weeks (grey area). Tumor volume was measured before treatment and then once a week. The individual relative tumor volume (RTV) was calculated as follows RTV=Vx/V1 where Vx is the volume in cubic millimeters at a given time and V1 is the volume at the start of treatment. Results are expressed as the mean percentage of change in tumor volume for each group of mice with S.D.

FIG. 5A (left panel): Western analysis of hMSH2 protein expression in removed tumors.

FIG. 5B: Representative tumor xenografts at week 6.

FIG. 5A (right panel): tumor growth during and after 5-FU treatment.

FIGS. 6A-6B.

Figure 6A:
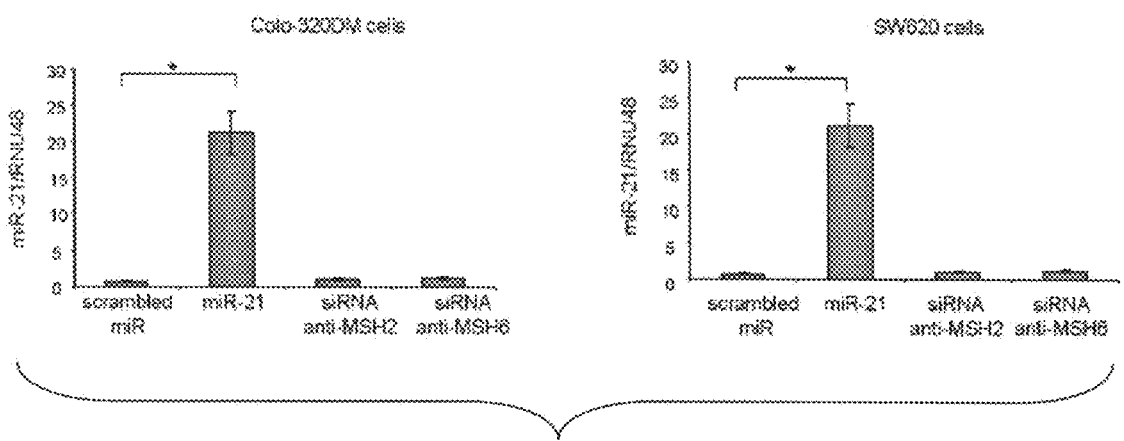

FIG. 6A: Colo-320DM and SW620 were transiently transfected with miR-21, scrambled-miR, siRNA anti-MSH2 or anti-MSH6 for 48 hours. miR-21 expression was assessed by real time PCR.

Figure 6B:
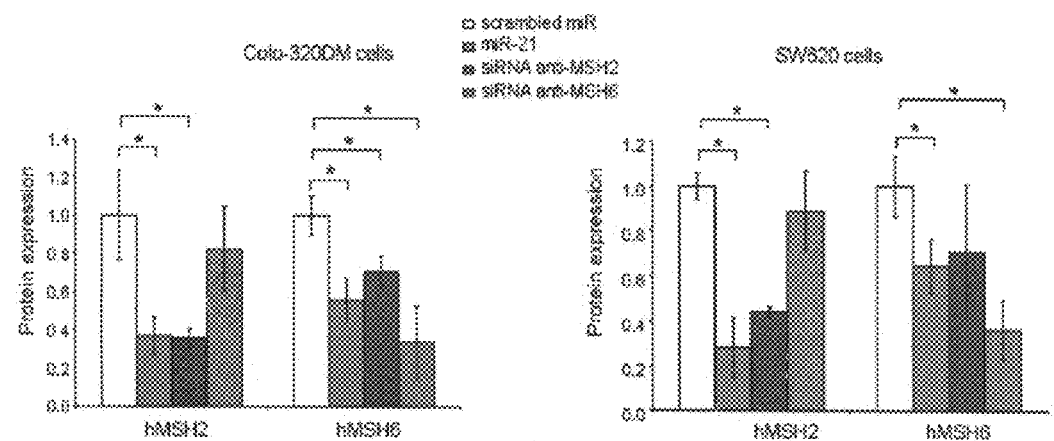

FIG. 6B: Protein expression was measured by densitometric analysis. Bars represent mean and S.D. of 3 experiments. *P<0.05.

Figure 7A:
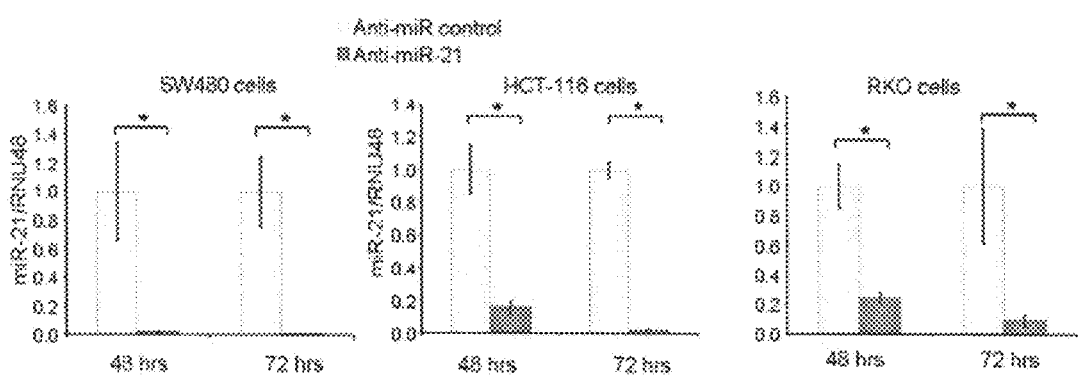
Figure 7B:
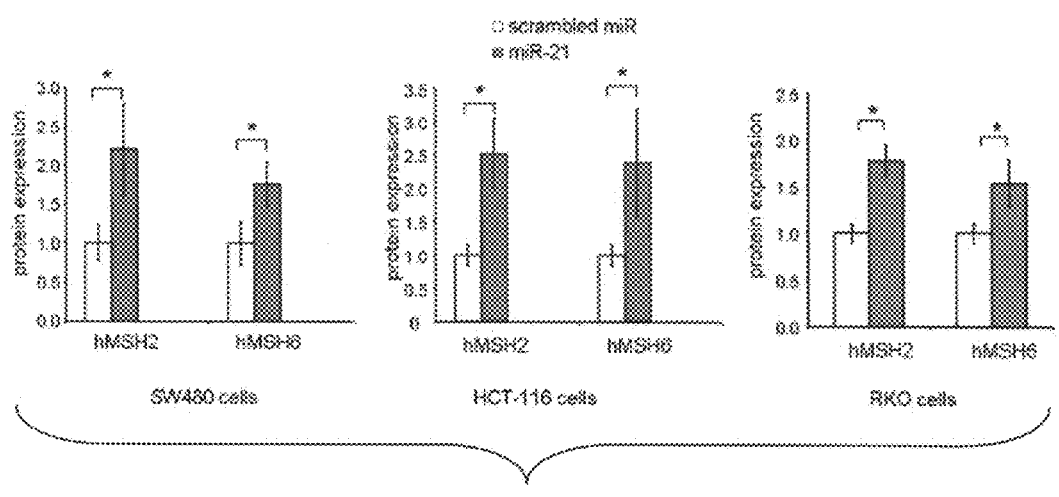
Figure 7C:
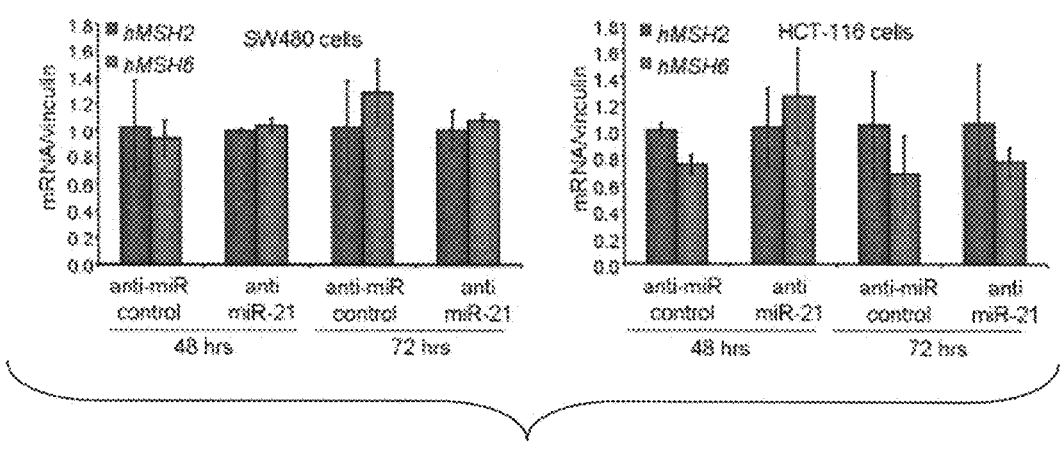

FIGS. 7A-7C. HCT-116, SW480 and RKO cells were transfected with an LNA to miR-21 (anti-miR-21) or LNA controls. 48 hours after transfection cells were harvested and RNAs and proteins were collected.

FIG. 7A: miR-21 expression analyzed by real time PCR in anti-miR-21 transfected cells compared to controls.

FIG. 7B: Protein expression was measured by densitometric analysis.

FIG. 7C: Real time PCR analysis of hMSH2 and hMSH6 mRNA expression. Bars represent mean and S.D. of 3 experiments. *P<0.05.

FIG. 8.

Scatter plot and regression curve plus confidence interval (red) of cases displaying high miR-21 and low hMSH2 expression. miR-21 was analyzed by Northern Blotting and hMSH2 by Western Blotting analysis in tumor and normal adjacent tissue. In the graph miR-21 and hMSH2 are expressed as ratio between tumor and normal tissue. Correlation is −0.81, 95% confidence Interval : −0.96 to −0.25, p<0.02.

FIG. 9.

SW620 and Colo-320DM cells were synchronized at G0-G1 by serum starvation for 48 hours. Cells were then trypsinized, counted, transfected with scrambled miR, miR-21, siRNA anti-MSH2 or siRNA-control, and re-plated in medium containing 10% FBS. 5-FU (50ug/ml) was added at 16 h after release, corresponding to a time just prior to entry into S phase but after the p53-mediated G1-S cell cycle checkpoint. The percentage of apoptotic cells was analyzed by FACS analysis after 48 hours following propidium iodine and Annexin V staining. Diagrams showing the percentage of G2/M arrested and apoptotic (sub-G1) cells. The data represent the mean and S.D. from at least 3 independent experiments. *p<0.01.

BRIEF DESCRIPTION OF THE SEQUENCE LISTING

The instant application contains a Sequence Listing which has been submitted via EFS-web and is hereby incorporated by reference in its entirety. The ASCII copy, created on Nov. 7, 2011, is named 53-52535_SEQ_LIST_OSURF 11085.txt, and is 3,139 bytes in size.

| Primers Name | Primer Fw 5'-3' | Primer Rv 5'-3' |
|---|---|---|
| SEQ ID NOS 1 and 6 hMSH2-LUC-WT | CAGAAAGCCCTGGAACTTGA | TCAATTGCAAACAGTCCTCAG |
| SEQ ID NOS 2 and 7 hMSH2-LUC-MUTANT | TTTCCATAGTGTTAACTGTCAGTGC | TCAATTGCAAACAGTCCTCAG |
| SEQ ID NOS 3 and 8 hMSH2-cDNA-Mutant | CCCAGTAATGGAATGAAGGGTCTG TAATAGTTTTATATTG | CAATATAAAACTATTACAGACCCTTC ATTCCATTACTGGG |
| SEQ ID NOS 4 and 9 hMSH6-LUC-WT | AAATGTTGCTGTGCGCCTA | TAGCTTTTCCTCCCCCATTT |

-continued

| Primers Name | Primer Fw 5'-3' | Primer Rv 5'-3' |
|---|---|---|
| SEQ ID NOS 5 and 10<br>hMSH6-LUC-MUTANT | AAATGTTGCTGTGCGCCTA | CCACCTTTGTCAGAAGTCAACTC |

DETAILED DESCRIPTION OF THE INVENTION

MiR-21 is commonly over-expressed in a number of human tumors including colorectal cancer. In recent years a several of miR-21 tumor suppressor targets have been identified that may accelerate the progression of cancer. The inventors herein found an inverse relationship between colorectal tumor cells that over-express miR-21 and those that express the hMSH2 tumor suppressor protein. Moreover, the inventors determined that miR-21 appears to directly target the 3'-UTR of both the hMSH2 and hMSH6 mRNA resulting in significant down-regulation of protein expression.

The state of the art therapeutic treatment of colorectal cancer includes 5-fluorouracil (5-FU). 5-FU exerts its cytotoxic effects by misincorporation of fluoronucleotides into RNA and DNA as well as inhibiting nucleotide synthesis by targeting the thymidylate synthetase (TS) enzyme. TS overexpression, defects in 5-FU metabolism, TP53 mutations and impairment of the MMR system are all hallmarks of 5-FU resistance and predictors of clinical outcome. More recently, both microRNA and gene expression analysis have revealed a higher level of complexity in predicting 5-FU benefit in stage II and III CRC patients who underwent adjuvant chemotherapy. Indeed, a retrospective analysis of stage II and III CRC patients treated with 5-FU analogs showed reduced survival in patients with high miR-21 expression. The same findings where confirmed in the subgroup of stage III CRC patients alone, while stage II CRC patients showed no statistically significant correlation. The low number of patients may account for this latter result. Cells with genetic or epigenetic defects of the MMR machinery appear to tolerate 5-FU metabolites as a result of defects in G2/M arrest and apoptosis.

The present invention show shows that down-regulation of hMSH2 by miR-21 induces resistance to 5-FU both in a cellular model and a xenograft tumor model. Taken together, the present results show that miR-21 tumor status is likely to be an important indicator of 5-FU therapeutic efficacy.

miR-21 appears to regulate a number of cell cycle and tumor suppressor genes. The present invention also shows that down-regulation of hMSH2 plays a central role in the development of 5-FU resistance. Indeed, inhibition of 5-FU-induced apoptosis and G2/M arrest by miR-21 was comparable to that caused by siRNA-mediated selective inhibition of hMSH2. Moreover, transfection of Lovo (MSH2-) cells with miR-21 did not alter cell cycle arrest or apoptosis, demonstrating that miR-21 induced effects are dependent upon hMSH2 expression. Taken together, the present results show that inhibition of miR-21 represents a synergic treatment to overcome 5-FU resistance.

The present invention also shows that miR-21 dependent down-regulation of hMSH2-hMSH6 is responsible for both primary and acquired resistance to 5-FU. In clinical practice, 5-FU is usually administered as a continuous infusion over a 48 hours period. Interestingly, miR-21 expression appears to increase in cell lines continuously exposed to 5-FU. In light of the present invention, the inventors contend that this over-expression may be a secondary mechanism of resistance and that cells acquire miR-21 over-expression to overcome 5-FU cytotoxicity. There is additional clinical relevance if one considers that hMSH2 is frequently down-regulated after primary chemotherapy including 5-FU or Cisplatin in rectal and ovarian cancers.

In summary, the inventors have shown 5-FU drug resistance in colorectal tumors due to the over-expression of miR-21 directly down-regulates the core MMR proteins hMSH2 and hMSH6, ultimately leading to a defect in damage-induced G2/M arrest and apoptosis.

Definitions And Abbreviations
DNA Deoxyribonucleic acid
mRNA Messenger RNA
PCR Polymerase chain reaction
pre-miRNA Precursor microRNA
qRT-PCR Quantitative reverse transcriptase polymerase chain reaction
RNA Ribonucleic acid It is to be understood that both the foregoing general description and the following detailed description are exemplary and explanatory only and are not intended to limit the scope of the current teachings. In this application, the use of the singular includes the plural unless specifically stated otherwise.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Decrease in survival: As used herein, "decrease in survival" refers to a decrease in the length of time before death of a patient, or an increase in the risk of death for the patient.

Detecting level of expression: For example, "detecting the level of miR or miRNA expression" refers to quantifying the amount of miR or miRNA present in a sample. Detecting expression of the specific miR, or any microRNA, can be achieved using any method known in the art or described herein, such as by qRT-PCR. Detecting expression of miR includes detecting expression of either a mature form of miRNA or a precursor form that is correlated with miRNA expression. Typically, miRNA detection methods involve sequence specific detection, such as by RT-PCR. miR-specific primers and probes can be designed using the precursor and mature miR nucleic acid sequences, which are known in the art and provided herein as in the SEQ ID NOs.

MicroRNA (miRNA): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially-complementary to one or more messenger RNA molecules, and their primary function is to down-regulate gene expression. MicroRNAs regulate gene expression through the RNAi pathway.

miR expression: As used herein, "low miR expression" and "high miR expression" are relative terms that refer to the level of miRNAs found in a sample. In some embodiments, low and high miR expression is determined by comparison of miRNA levels in a group of control samples and test samples. Low and high expression can then be assigned to each sample based on whether the expression of mi in a sample is above (high) or below (low) the average or median miR expression level. For individual samples, high or low miR expression can be determined by comparison of the sample to a control or reference sample known to have high or low expression, or by comparison to a standard value. Low and high miR expression can include expression of either the precursor or mature forms of miRNA, or both.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Screening: As used herein, "screening" refers to the process used to evaluate and identify candidate agents that affect such disease. Expression of a microRNA can be quantified using any one of a number of techniques known in the art and described herein, such as by microarray analysis or by qRT-PCR.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

As used herein, a "candidate agent" or "test compound" is a compound selected for screening to determine if it can function as a therapeutic agent. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically-effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

In some embodiments of the present methods, use of a control is desirable. In that regard, the control may be a non-cancerous tissue sample obtained from the same patient, or a tissue sample obtained from a healthy subject, such as a healthy tissue donor. In another example, the control is a standard calculated from historical values. Tumor samples and non-cancerous tissue samples can be obtained according to any method known in the art. For example, tumor and non-cancerous samples can be obtained from cancer patients that have undergone resection, or they can be obtained by extraction using a hypodermic needle, by microdissection, or by laser capture. Control (non-cancerous) samples can be obtained, for example, from a cadaveric donor or from a healthy donor.

In some embodiments, screening comprises contacting the candidate agents/test compounds with cells. The cells can be primary cells obtained from a patient, or the cells can be immortalized or transformed cells.

The candidate agent/test compounds can be any type of agent, such as a protein, peptide, small molecule, antibody or nucleic acid. In some embodiments, the candidate agent is a cytokine. In some embodiments, the candidate agent is a small molecule. Screening includes both high-throughout screening and screening individual or small groups of candidate agents.

MicroRNA Detection

In some methods herein, it is desirable to identify miRNAs present in a sample.

The sequences of precursor microRNAs (pre-miRNAs) and mature miRNAs are publicly available, such as through the miRBase database, available online by the Sanger Institute (see Griffiths-Jones et al., Nucleic Acids Res. 36:D154-D158, 2008; Griffiths-Jones et al., Nucleic Acids Res. 34:D140-D144, 2006; and Griffiths-Jones, Nucleic Acids Res. 32:D109-D111, 2004). The sequences of the precursor and mature forms of the presently disclosed preferred family members are provided herein.

Detection and quantification of RNA expression can be achieved by any one of a number of methods well known in the art (see, for example, U.S. Patent Application Publication Nos. 2006/0211000 and 2007/0299030, herein incorporated by reference) and described below. Using the known sequences for RNA family members, specific probes and primers can be designed for use in the detection methods described below as appropriate.

In some cases, the RNA detection method requires isolation of nucleic acid from a sample, such as a cell or tissue sample. Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs).

In some embodiments, use of a microarray is desirable. A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used, for example, to measure the expression levels of large numbers of messenger RNAs (mRNAs) and/or miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

Microarray analysis of miRNAs, for example (although these procedures can be used in modified form for any RNA analysis) can be accomplished according to any method known in the art (see, for example, PCT Publication No. WO 2008/054828; Ye et al., Nat. Med. 9(4):416-423, 2003; Calin et al., N. Engl. J. Med. 353(17):1793-1801, 2005, each of which is herein incorporated by reference). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described above.

There are several types of microarrays than be employed, including spotted oligonucleotide microarrays, pre-fabricated oligonucleotide microarrays and spotted long oligonucleotide arrays. In spotted oligonucleotide microarrays, the capture probes are oligonucleotides complementary to miRNA sequences. This type of array is typically hybridized with amplified PCR products of size-selected small RNAs from two samples to be compared (such as non-cancerous tissue and cancerous or sample tissue) that are labeled with two different fluorophores. Alternatively, total RNA containing the small RNA fraction (including the miRNAs) is extracted from the two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated miRNA genes in one assay.

In pre-fabricated oligonucleotide microarrays or single-channel microarrays, the probes are designed to match the sequences of known or predicted miRNAs. There are commercially available designs that cover complete genomes (for example, from Affymetrix or Agilent). These microarrays give estimations of the absolute value of gene expression and therefore the comparison of two conditions requires the use of two separate microarrays.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miR, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, three of which are described below.

Methods for quantitative polymerase chain reaction include, but are not limited to, via agarose gel electrophoresis, the use of SYBR Green (a double stranded DNA dye), and the use of a fluorescent reporter probe. The latter two can be analyzed in real-time.

With agarose gel electrophoresis, the unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown.

The use of SYBR Green dye is more accurate than the agarose gel method, and can give results in real time. A DNA binding dye binds all newly synthesized double stranded DNA and an increase in fluorescence intensity is measured, thus allowing initial concentrations to be determined However, SYBR Green will label all double-stranded DNA, including any unexpected PCR products as well as primer dimers, leading to potential complications and artifacts. The reaction is prepared as usual, with the addition of fluorescent double-stranded DNA dye. The reaction is run, and the levels of fluorescence are monitored (the dye only fluoresces when bound to the double-stranded DNA). With reference to a standard sample or a standard curve, the double-stranded DNA concentration in the PCR can be determined The fluorescent reporter probe method uses a sequence-specific nucleic acid based probe so as to only quantify the probe sequence and not all double stranded DNA. It is commonly carried out with DNA based probes with a fluorescent reporter and a quencher held in adjacent positions (so-called dual-labeled probes). The close proximity of the reporter to the quencher prevents its fluorescence; it is only on the breakdown of the probe that the fluorescence is detected. This process depends on the 5' to 3' exonuclease activity of the polymerase involved.

The real-time quantitative PCR reaction is prepared with the addition of the dual-labeled probe. On denaturation of the double-stranded DNA template, the probe is able to bind to its complementary sequence in the region of interest of the template DNA. When the PCR reaction mixture is heated to activate the polymerase, the polymerase starts synthesizing the complementary strand to the primed single stranded template DNA. As the polymerization continues, it reaches the probe bound to its complementary sequence, which is then hydrolyzed due to the 5'-3' exonuclease activity of the polymerase, thereby separating the fluorescent reporter and the quencher molecules. This results in an increase in fluorescence, which is detected. During thermal cycling of the real-time PCR reaction, the increase in fluorescence, as released from the hydrolyzed dual-labeled probe in each PCR cycle is monitored, which allows accurate determination of the final, and so initial, quantities of DNA.

In some embodiments, use of in situ hybridization is desirable. In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of miRNAs.

Sample cells or tissues are treated to increase their permeability to allow a probe, such as a miRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous or cancerous tissue sample. Since the sequences of miR-155 family members are known, miR-155 probes can be designed accordingly such that the probes specifically bind miR-155.

In some embodiments, use of in situ PCR is desirable. In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

Use of differentially-expressed miR5 and miRNAs as predictive markers of prognosis and for identification of therapeutic agents. It is disclosed herein that certain expression patterns of miR-155, along with status indicators are predictors of survival prognosis in certain patients. As used herein, "poor prognosis" generally refers to a decrease in survival, or in other words, an increase in risk of death or a decrease in the time until death. Poor prognosis can also refer to an increase in severity of the disease, such as an increase in spread (metastasis) of the cancer to other organs. In one embodiment, the respective markers show at least a 1.5-fold increase or decrease in expression relative to the control. In other embodiments, poor prognosis is indicated by at least a 2-fold, at least a 2.5-fold, at least a 3-fold, at least a 3.5-fold, or at least a 4-fold increase or decrease in the markers relative to the wild-type tumor control figures.

Methods of screening candidate agents to identify therapeutic agents for the treatment of disease are well known in the art. Methods of detecting expression levels of RNA and proteins are known in the art and are described herein, such as, but not limited to, microarray analysis, RT-PCR (including qRT-PCR), in situ hybridization, in situ PCR, and Northern blot analysis. In one embodiment, screening comprises a high-throughput screen. In another embodiment, candidate agents are screened individually.

The candidate agents can be any type of molecule, such as, but not limited to nucleic acid molecules, proteins, peptides, antibodies, lipids, small molecules, chemicals, cytokines, chemokines, hormones, or any other type of molecule that may alter cancer disease state(s) either directly or indirectly.

Typically, an endogenous gene, miRNA or mRNA is modulated in the cell. In particular embodiments, the nucleic acid sequence comprises at least one segment that is at least 70, 75, 80, 85, 90, 95, or 100% identical in nucleic acid sequence to one or more miRNA sequence listed in Table 1. Modulation of the expression or processing of an endogenous gene, miRNA, or mRNA can be through modulation of the processing of a mRNA, such processing including transcription, transportation and/or translation with in a cell. Modulation may also be effected by the inhibition or enhancement of miRNA activity with a cell, tissue, or organ. Such processing may effect the expression of an encoded product or the stability of the mRNA. In still other embodiments, a nucleic acid sequence can comprise a modified nucleic acid sequence. In certain aspects, one or more miRNA sequence may include or comprise a modified nucleobase or nucleic acid sequence.

It will be understood in methods of the invention that a cell or other biological matter such as an organism (including patients) can be provided an miRNA or miRNA molecule corresponding to a particular miRNA by administering to the cell or organism a nucleic acid molecule that functions as the corresponding miRNA once inside the cell. The form of the molecule provided to the cell may not be the form that acts a miRNA once inside the cell. Thus, it is contemplated that in some embodiments, biological matter is provided a synthetic miRNA or a nonsynthetic miRNA, such as one that becomes processed into a mature and active miRNA once it has access to the cell's miRNA processing machinery. In certain embodiments, it is specifically contemplated that the miRNA molecule provided to the biological matter is not a mature miRNA molecule but a nucleic acid molecule that can be processed into the mature miRNA once it is accessible to miRNA processing machinery. The term "nonsynthetic" in the context of miRNA means that the miRNA is not "synthetic," as defined herein. Furthermore, it is contemplated that in embodiments of the invention that concern the use of synthetic miRNAs, the use of corresponding nonsynthetic miRNAs is also considered an aspect of the invention, and vice versa. It will be understand that the term "providing" an agent is used to include "administering" the agent to a patient.

In certain embodiments, methods also include targeting a miRNA to modulate in a cell or organism. The term "targeting a miRNA to modulate" means a nucleic acid of the invention will be employed so as to modulate the selected miRNA. In some embodiments the modulation is achieved with a synthetic or non-synthetic miRNA that corresponds to the targeted miRNA, which effectively provides the targeted miRNA to the cell or organism (positive modulation). In other embodiments, the modulation is achieved with a miRNA inhibitor, which effectively inhibits the targeted miRNA in the cell or organism (negative modulation).

In some embodiments, the miRNA targeted to be modulated is a miRNA that affects a disease, condition, or pathway. In certain embodiments, the miRNA is targeted because a treatment can be provided by negative modulation of the targeted miRNA. In other embodiments, the miRNA is targeted because a treatment can be provided by positive modulation of the targeted miRNA.

In certain methods of the invention, there is a further step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result like decrease in cell viability). Consequently, in some methods of the invention there is a step of identifying a patient in need of treatment that can be provided by the miRNA modulator(s). It is contemplated that an effective amount of a miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

Furthermore, it is contemplated that the miRNA compositions may be provided as part of a therapy to a patient, in conjunction with traditional therapies or preventative agents. Moreover, it is contemplated that any method discussed in the context of therapy may be applied as preventatively, particularly in a patient identified to be potentially in need of the therapy or at risk of the condition or disease for which a therapy is needed.

In addition, methods of the invention concern employing one or more nucleic acids corresponding to a miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating cancer in a patient comprising administering to the patient the cancer therapeutic and an effective amount of at least one miRNA molecule that improves the efficacy of the cancer therapeutic or protects non-cancer cells. Cancer therapies also include a variety of combination therapies with both chemical and radiation based treatments. Combination chemotherapies include but are not limited to, for example, bevacizumab, cisplatin (CDDP), carboplatin, EGFR inhibitors (gefitinib and cetuximab), procarbazine, mechlorethamine, cyclophosphamide, camptothecin, COX-2 inhibitors (e.g., celecoxib) ifosfamide, melphalan, chlorambucil, busulfan, nitrosurea, dactinomycin, daunorubicin, doxorubicin (adriamycin), bleomycin, plicomycin, mitomycin, etoposide (VP16), tamoxifen, raloxifene, estrogen receptor binding agents, taxol, taxotere, gemcitabien, navelbine, farnesyl-protein transferase inhibitors, transplatinum, 5-fluorthe ouracil, vincristin, vinblastin and methotrexate, or any analog or derivative variant of the foregoing.

Generally, inhibitors of miRNAs can be given to achieve the opposite effect as compared to when nucleic acid molecules corresponding to the mature miRNA are given. Similarly, nucleic acid molecules corresponding to the mature miRNA can be given to achieve the opposite effect as compared to when inhibitors of the miRNA are given. For example, miRNA molecules that increase cell proliferation can be provided to cells to increase proliferation or inhibitors of such molecules can be provided to cells to decrease cell proliferation. The present invention contemplates these embodiments in the context of the different physiological effects observed with the different miRNA molecules and miRNA inhibitors disclosed herein. These include, but are not limited to, the following physiological effects: increase and decreasing cell proliferation, increasing or decreasing apoptosis, increasing transformation, increasing or decreasing cell viability, reduce or increase viable cell number, and increase or decrease number of cells at a particular phase of the cell cycle. Methods of the invention are generally contemplated to include providing or introducing one or more different nucleic acid molecules corresponding to one or more different miRNA molecules. It is contemplated that the following, at least the following, or at most the following number of different nucleic acid molecules may be provided or introduced: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. This also applies to the number of different miRNA molecules that can be provided or introduced into a cell.

The principle and mode of operation of this invention have been explained and illustrated in its preferred embodiment. However, it must be understood that this invention may be practiced otherwise than as specifically explained and illustrated without departing from its scope.

EXAMPLES

Example 1

Materials and Methods
Cell Cultures and Transfection
Colo-320DM, SW620, SW480, HCT-116 and RKO colorectal cancer (CRC) cells (American Type Culture Collection ATCC Manassas, Va.) were cultured in RPMI 1640 (Gibco, Carlsbad, Calif.), and packaging cells 293TN (System Biosciences, Mountain View, Calif.) were grown in DMEM (Gibco, Carlsbad, Calif.). Lovo+chr2hMSH2+/2 and Lovo(DT40.2)-4-1hMSH22/2 1 were grown in IMDM (Gibco, Carlsbad, Calif.) containing 700 mg/ml G418 (Gibco). All cells were supplemented with 10% fetal bovine serum (Sigma, St. Louis, Mo.) plus antibiotics. Cells were examined for Mycoplasma contamination periodically and were always found negative. Cells were transfected in 6-well plates by using Lipofectamine 2000 (Invitrogen, Carlsbad, Calif.) following manufacturer's protocol. For over-expression studies specific miRNA or control precursor oligonucleotides were purchased from Ambion (Austin, Tex.) and used at 50 nM. Ontarget-plus siRNA to hMSH2 and hMSH6 (Dharmacon, Colo.) were used as control. For silencing experiments miRCURY LNA™ anti-miR-21 or control miR-CURY knockdown probe (Exiqon, Vedbaek, Denmark) were used at 50 nM. miRNA expression was verified after 48 hours by quantitative real time PCR as described below. Plasmids encoding the full length MSH2 cDNA were purchased from Origene. The hMSH2 mutant for the miR-21 seed region was prepared using QuikChange site-directed mutagenesis kit (Stratagene, San Diego, Calif.) (Table 2).

TABLE 2

List of primers used for cloning

| Primers Name | Primer Fw 5'-3' | Primer Rv 5'-3' |
|---|---|---|
| SEQ ID NOS 1 and 6 hMSH2-LUC-WT | CAGAAAGCCCTGGAACTTGA | TCAATTGCAAACAGTCCTCAG |
| SEQ ID NOS 2 and 7 hMSH2-LUC-MUTANT | TTTCCATAGTGTTAACTGTCAGTGC | TCAATTGCAAACAGTCCTCAG |
| SEQ ID NOS 3 and 8 hMSH2-cDNA-Mutant | CCCAGTAATGGAATGAAGGGTCT GTAATAGTTTTATATTG | CAATATAAAACTATTACAGACC CTTCATTCCATTACTGGG |
| SEQ ID NOS 4 and 9 hMSH6-LUC-WT | AAATGTTGCTGTGCGCCTA | TAGCTTTTCCTCCCCCATTT |
| SEQ ID NOS 5 and 10 hMSH6-LUC-MUTANT | AAATGTTGCTGTGCGCCTA | CCACCTTTGTCAGAAGTCAACTC |

Luciferase Assay
The predicted miRNA binding sites in the 3'-UTR of hMSH2 and hMSH6 were cloned downstream of the firefly luciferase gene as follows. Complimentary DNA (cDNA) and genomic DNA from SW-480 cells was amplified by PCR using specific primers for hMSH2 and hMSH6 cloning respectively (Table 2). The product was then digested with SpeI and SacII (New England Biolabs Ipswich, Mass.) and inserted into the pGL3 control vector (Promega, Madison, Wis.) previously modified to harbor the SpeI and SacII sites immediately downstream of the stop codon of the firefly luciferase gene. Reporter constructs with mutated miRNA recognition sequences were constructed for each single gene (MUT-21). For both hMSH2 and hMSH6 miR-21 seed regions, mutant constructs were obtained using primers sited up or downstream of the predicted miRNA binding site in order to exclude the seed-region complementary sites.

Colo-320DM and SW480 cells were co-transfected in 12-well plates with 1 μg of pGL3 firefly luciferase reporter control vector, 0.1 μg of the phRL-SV40 control vector (Promega, Madison, Wis.), and 50 nM miRNA, control precursors, LNA against miR-21 or LNA control. Firefly and Renilla luciferase activities were measured consecutively by using the Dual Luciferase Assay (Promega) 24 hours after transfection.

Western Blotting
For immunoblotting analysis cells were lysed with ice-cold Cell Lysis Buffer plus protease inhibitor (Cell Signaling Technology Inc. Danvers, Mass.). Equivalent amounts of protein were resolved and mixed with 4×SDS-PAGE sample buffer, electrophoresed in a 4%-20% and 7.5% linear gradient Tris-HCL Criterion Precast Gels (Bio-Rad), and transferred to nitrocellulose or PVDF membranes (Bio-Rad). The membranes were blocked with 5% nonfat dry milk in Tris-buffered saline, pH 7.4, containing 0.05% Tween 20, and were incubated with primary and secondary antibodies according to the manufacturer's instructions. The following primary antibodies were used: mouse monoclonal anti-MSH2 (1:200, Invitrogen), mouse monoclonal anti-MSH6 (1:500, BD Biosciences San Jose, Calif.), mouse monoclonal anti-actin (1:5000, Sigma), mouse monoclonal anti-GAPDH (1:1000, SantaCruz Biotechnology).

Real Time PCR for Mature miRNAs and Genes

Total RNA was isolated with Trizol (Invitrogen). Mature miRNAs were assessed by the single-tube TaqMan MicroRNA Assay, while the expression of mRNAs of interest evaluated by the Gene Expression Assay with the following probes: hMSH2=Hs00953523_m1, hMSH6=Hs00943001_ml (Applied Biosystems, Foster City, Calif.). miRNA expression was normalized to that of RNU44 and RNU48. Gene expression was normalized to vinculin. All retrotranscriptase (RT) reactions, including no-template controls and RT minus controls, were run in a GeneAmp PCR 9700 Thermocycler (Applied Biosystems). Each sample was tested in triplicate unless otherwise specified.

Northern Blotting

For mature miRNA detection, acrilamide Northern blotting was performed as previously described 2.

MiRNA Locked Nucleic Acid (LNA) In Situ Hybridization of Formalin Fixed, Paraffin-Embedded Tissue Section.

MicroRNA detection was performed on colon cancer tissue array (US Biomax BCO05118) containing 50 normal and cancer colon cores in duplicate by in situ hybridization (ISH) as previously described3. The negative controls included omission of the probe and the use of a scrambled LNA probe. After in situ hybridization for the miRNAs, the slides were analyzed for immunohistochemistry using the optimal conditions for hMSH2 (Ventana cat #760-4265). For immunohistochemistry, the inventors used the Ultrasensitive Universal Fast Red system from Ventana Medical Systems (Tucson, Ariz.). Pictures of representative spots have been taken with the Nuance system (Ventana). Cancer cores were scored for miR-21 and hMSH2 proteins expression based on the number of positive cells in the core.

Tissue Collection

Fresh frozen tissues from tumor and normal adjacent tissue from 83 consecutive cases of CRC were collected at the Istituto Scientifico Romagnolo per lo Studio e la Cura dei Tumori, Meldola, Italy after approval of the ethical committee. Cell lysates for protein and RNA extraction were extracted as above mentioned, Cell Cycle Analyses and Apoptosis Analysis Propidium iodide (PI) staining: cells were detached with trypsin, washed with cold phosphate-buffered saline (PBS)-5% FCS and then fixed in 70% ethanol for 24 h. After washing with PBS, cells were incubated with 1 µg/ml PI for 3 h at 25° C. before FACS analysis by Coulter Epics XL flow cytometer (Beckman Coulter, Fullerton, Calif.). Cells were considered apoptotic when their DNA content was <2N. AnnexinV staining: Cells were detached with trypsin, washed with PBS-5% FCS and then placed in binding buffer containing 0.14 M NaCl, 2.5 mM CaCl2 and 0.01 M N-2-hydroxyethylpiperazine-N'-2-ethanesulfonic acid (pH 7.4) to which 7-aminoactinomycin D (7-AAD) and annexin V-FITC (Pharmingen, San Diego, Calif.) were added prior to FACS analysis. Cells were considered apoptotic when annexin V-FITC positive and 7-AAD negative.

Synchronization experiments were run as follow: Lovo-MSH2 positive, Lovo-MSH2 negative, SW620 and Colo-320DM cells were synchronized by arrest in G0-G1 via confluence and low serum treatments for 48 hours 4, cells were then dissociated with trypsin, counted, transfected with Pre-miR-control, Pre-miR-21, siRNA agains hMSH2, siRNA-control and vectors encoding for the full length MSH2 cDNA (with or without miR-21 seed region) using Cell Nucleofector® Kit (Lonza Walkersville, Inc ME) or Lipofectamine 2000TM (Invitrogen, Carlsbad, Calif.) following manufacturer instructions and replated in medium containing 10% FBS. 5-Fluorouracil (50 ug/ml 5) addition occurred at 16 h after release, corresponding to a time just prior to entry into S phase but after the p53-mediated G1-S cell cycle checkpoint.

Generation of Stable Clones Over-Expressing miR-21

Lovo-MSH2 positive and Lovo-MSH2 negative cells were stably infected with the pCDH-CMV-MCS-EF1-miRNA expression plasmid containing the full-length miR-21 and the GFP gene under the control of two different promoters (System Biosciences, Mountain View, Calif.). An empty vector was used as control. Pre-miR-21 expression and control constructs were packaged with pPACKH1 Lentivector Packaging Plasmid mix (System Biosciences) in 293-TN packaging cell line. Viruses were concentrated using PEG-It™ Virus Precipitation Solution and titers analyzed using UltraRapid Lentiviral Titer Kit (System Biosciences). Infected cells were selected by FACS analysis (FACS Calibur, Becton Dickinson Immunocytometry Systems). Infection efficiency >90% was verified by fluorescent microscopy and further confirmed by real time PCR for miR-21 expression.

Xenografts Studies.

Animal studies were performed according to institutional guidelines. Lovo MSH2-positive cells infected with lentiviral vectors encoding for either miR-21, siRNA to hMSH2 or empty vector as control and Lovo hMSH2-negative infected with empty virus were injected in the flank of nude mice (5×106). When xenografts (6 animals for each group) reached a palpable volume, 5-FU (50 mg/kg/day) was administered by intraperitoneal injection for 5 consecutive days a week for 2 weeks. Tumor volume was measured at the beginning of treatment and then once a week. The estimated tumor volume (V) was calculated by the following formula: V=W2×L×0.5, where W represents the largest tumor diameter in centimeters and L represents the next largest tumor diameter. The individual relative tumor volume (RTV) was calculated as follows RTV=Vx/V1 where Vx is the volume in cubic millimeters at a given time and V1 is the volume at the start of treatment.

Example 2

MiR-21 Directly Targets hMSH2 and hMSH6 Protein Expression

Figure 1A:
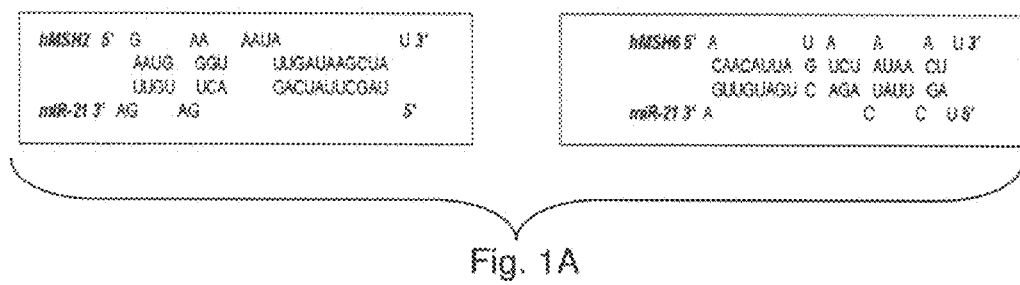
FIGS. 1A-1F. MSH2 and MSH6 are direct targets of miR-21.
Figure 1B:
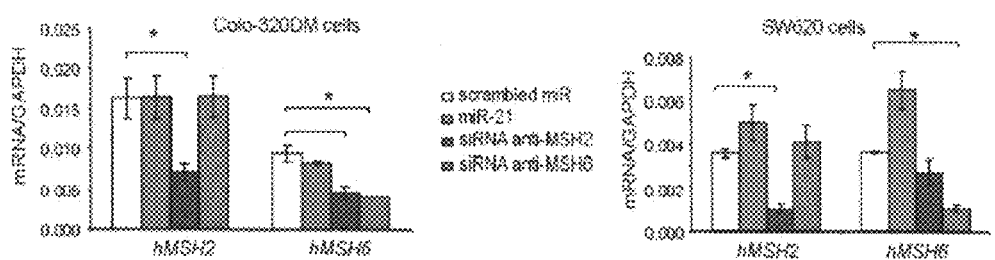

In silico analysis showed that miR-21 might target hMSH2 and hMSH6 mRNA (TargetScan, Whitehead Institute, MIT, FIG. 1A). The inventors identified a putative binding sites for miR-21 in both hMSH2 (NCBI NM_000249.2) and hMSH6 (NCBI NM_000179.2) 3'-UTR. The inventors examined the effect of miR-21 expression on endogenous hMSH2 and hMSH6 mRNA expression in CRC Colo-320DM and SW620 cells. Both cell lines display low basal miR-21 expression. The inventors transfected these cell lines with miR-21 precursor (miR-21) or a scrambled miR precursor control (FIG. 6). Over-expression of a specific small-interfering RNA (siRNA) to hMSH2 (anti-MSH2) or hMSH6 (anti-MSH6) did not affect the levels of miR-21 (FIG. 6A). The mRNA levels of hMSH2 and hMSH6 were unaffected by over-expression of miR-21 (FIG. 1B). In contrast, anti-MSH2 and anti-MSH6 siRNA specifically reduced the expression of hMSH2 and hMSH6 mRNA respectively (FIG. 1B). The inventors note a consistent reduction in the expression of hMSH6 mRNA with the anti-MSH2 siRNA. This reduction could be a result of degenerate hybridization of the anti-MSH2 siRNA with the hMSH6 mRNA or reduced hMSH6 mRNA stability resulting from the diminished heterodimeric protein partner hMSH2. The present results show that miR-21 over-expression does not affect the mRNA levels of hMSH2 or hMSH6.

Figure 1C:
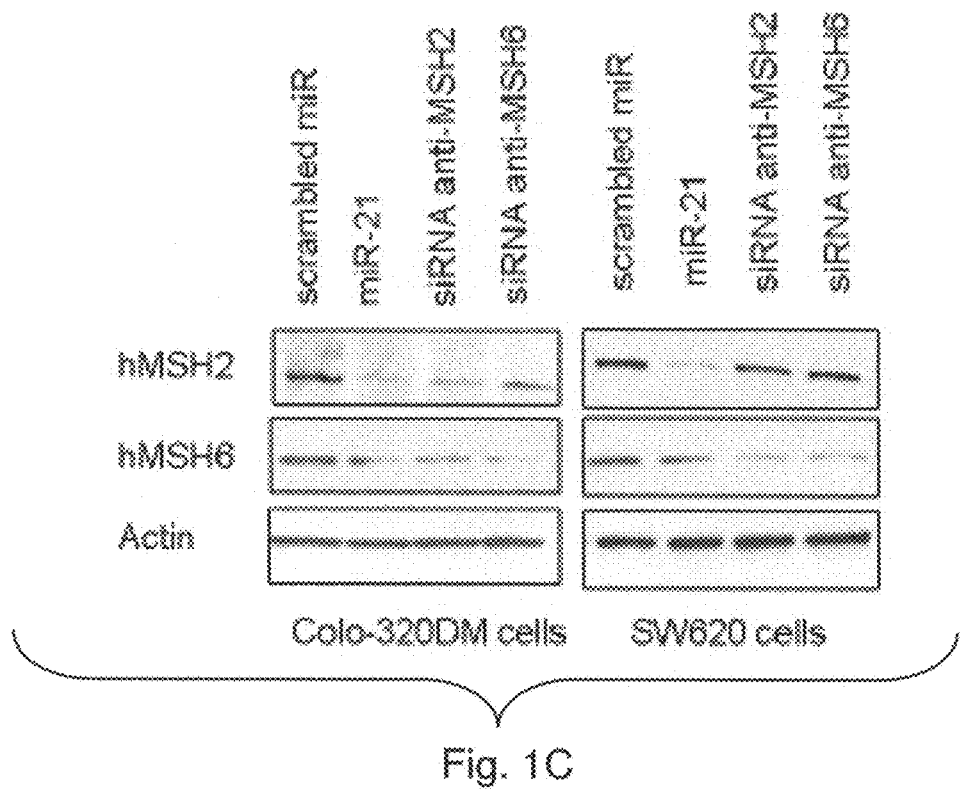
Figure 1D:
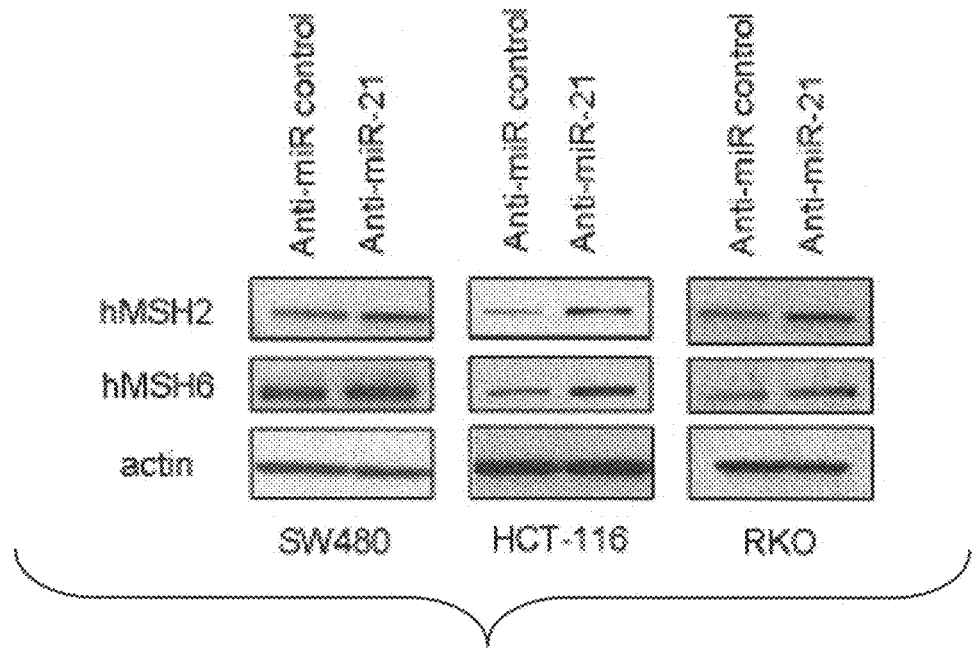

The inventors examined the protein levels of hMSH2 and hMSH6 following transfection of miR-21 in Colo-320DM and SW620 cells by western blotting analysis (FIG. 1C, FIG. 6B). hMSH2 and hMSH6 proteins were significantly reduced in cells over-expressing miR-21 compared to the scrambled miR. The anti-MSH2 and anti-MSH6 siRNA were transfected in these cell lines in parallel. The inventors observed that miR-21 transfected cells displayed a down-regulation of hMSH2 and hMSH6 that appeared comparable to cells transfected with siRNAs. Conversely, the inventors transfected CRC SW480, HCT116 and RKO cells that contain high levels of endogenous miR-21 with a locked nucleic acid (LNA) against miR-21 (anti-miR-21) or a scrambled LNA (anti-miR control). The inventors found that cells transfected with anti-miR-21 showed an increase in both hMSH2 and hMSH6 protein expression (FIG. 1D; FIG. 7B), while no changes in mRNA levels was observed (FIG. 7C).

Figure 1E:
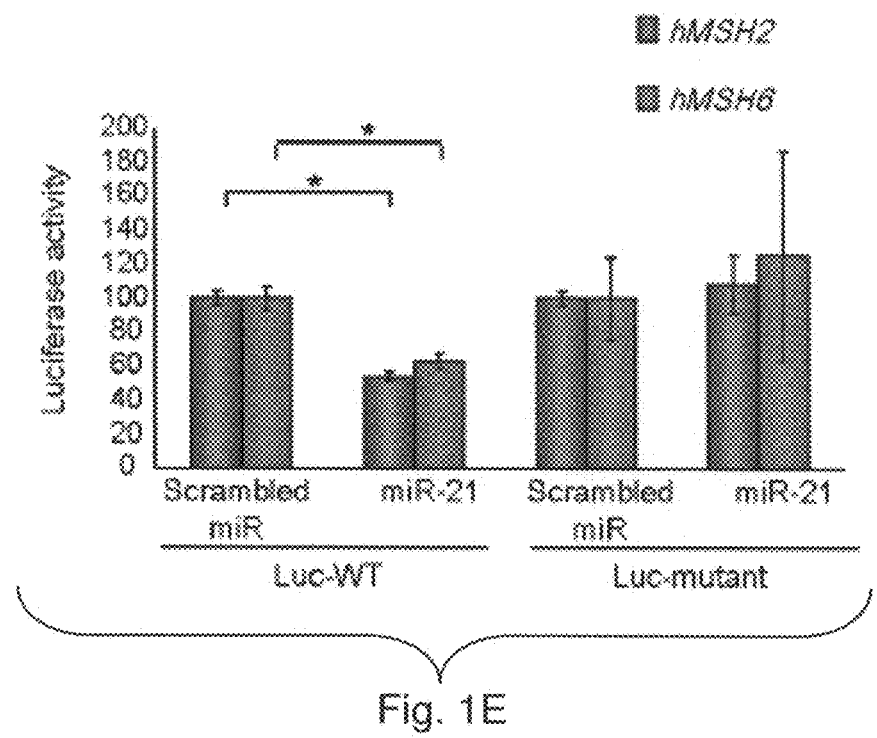
Figure 1F:
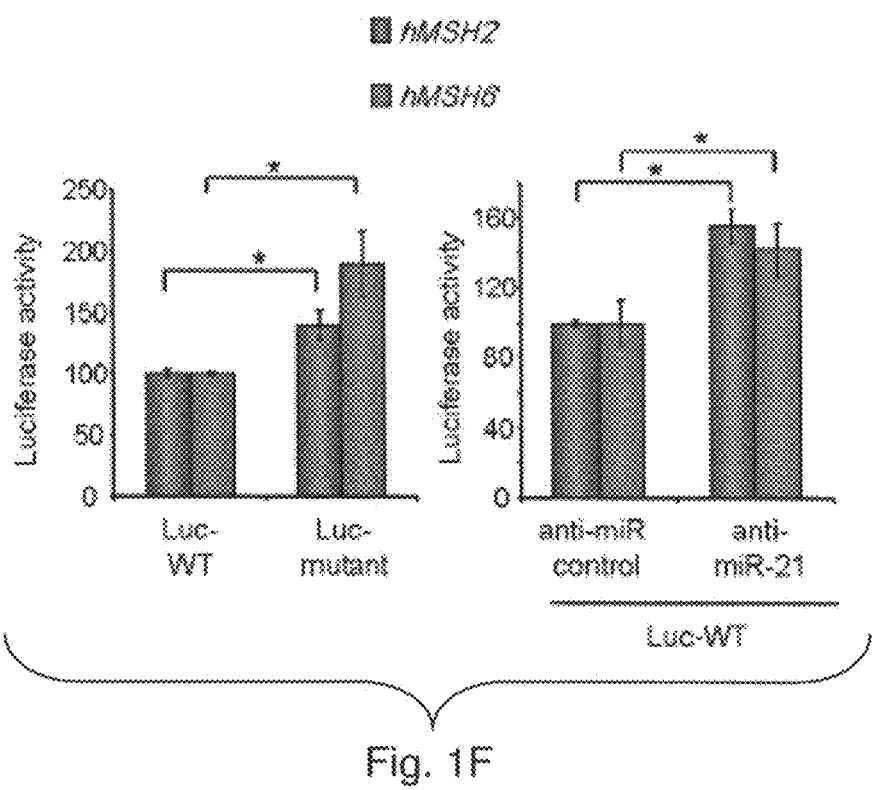

The entire 3'UTR of hMSH2 or hMSH6 was sub-cloned downstream of the luciferase gene. The luciferase reporter construct along with a precursor miR-21 (miR-21) or scrambled miR was then transfected into the Colo-320DM cells. The inventors observed a 50% and 37% reduction in the luciferase activity with constructs containing the miR-21 seed regions for hMSH2 or hMSH6 respectively (p<0.001; FIG. 1E). Deletion of the miR-21 seed regions resulted in the restoration of luciferase activity for both vectors containing hMSH2 or hMSH6 (FIG. 1E). The inventors transfected SW480 cells that displayed high levels of miR-21 expression with a luciferase reporter vector containing the wild type (WT) or mutated (mutant) hMSH2 and hMSH6 3'-UTR seed region (FIG. 1F). As expected, the inventors found that ablation of the miR-21 binding site resulted in increased luciferase activity for both the hMSH2 and hMSH6-vector transfected cells. To confirm these observations, SW480 cells were co-transfected with the hMSH2 and hMSH6 3'-UTR luciferase reporter plus the LNA anti-miR-21 or anti-miR control. LNA silencing of miR-21 induced an increase in luciferase activity (FIG. 1F). Taken as a whole, the present results show that miR-21 exerts a direct effect on the hMSH2 and hMSH6 3'-UTR that ultimately regulates hMSH2 and hMSH6 protein expression. Since hMSH2 protein status can affect hMSH6 protein stability and expression (9), the inventors cannot exclude the possibility that miR-21 regulation and hMSH2 protein loss can contribute to hMSH6 down-regulation.

Example 3 miR-21 is Inversely Correlated to the MMR Core Protein hMSH2 in CRC Tissues

Figure 2A:
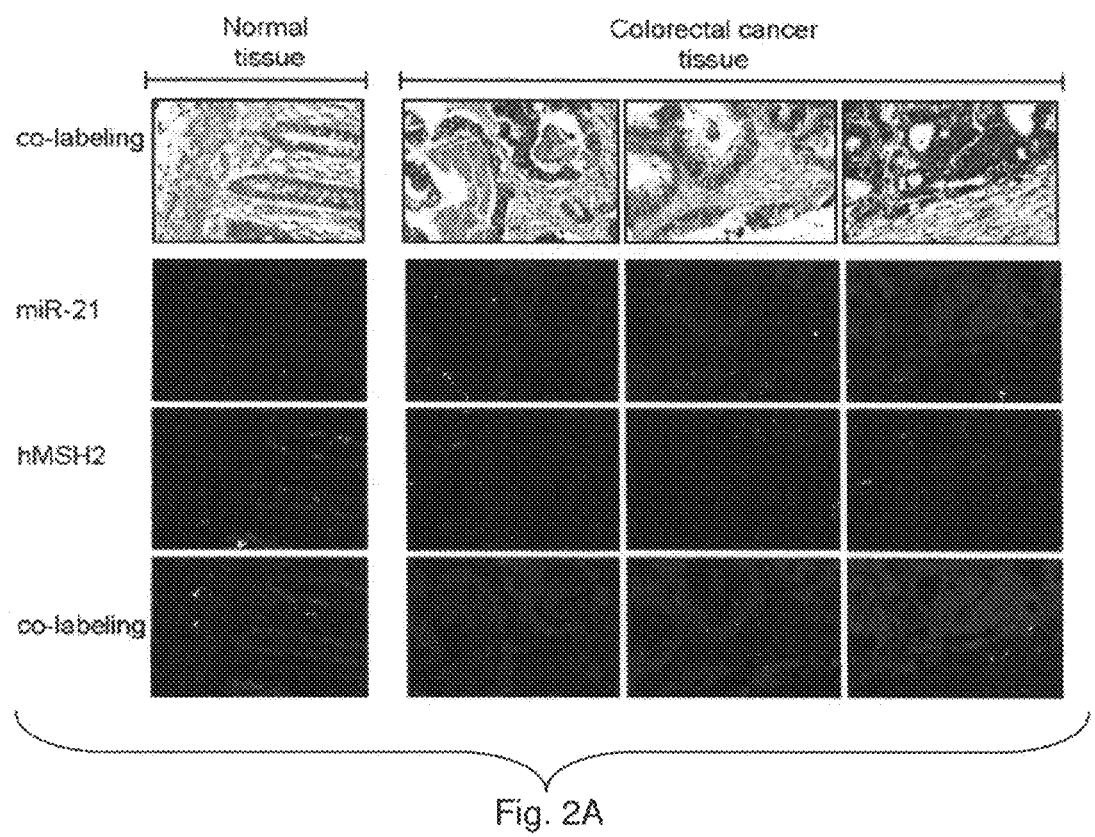
FIG. 2A. The MMR core protein hMSH2 expression is inversely correlated to mir-21, expression in CRC samples.
Figure 2B:
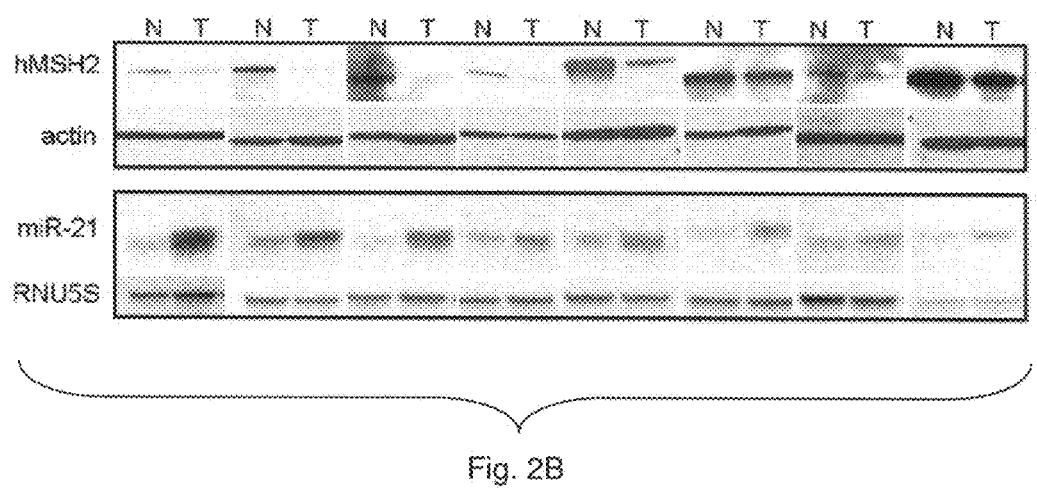
FIG. 2B: RNA and proteins were extracted from fresh frozen human colorectal tissues. miR-21 expression was assessed by northern blotting, and MMR proteins expression by western blotting in a series of human CRC.

The inventors examined miR-21 and hMSH2 expression in two different CRC cohorts (FIG. 2). A tissue microarray containing 50 unselected cases of CRC and paired normal adjacent tissue was hybridized with an LNA anti-miR-21 or nonspecific LNA anti-miR control combined with immuno-histochemical (1HC) staining for hMSH2 protein (FIG. 2A). A score for both miR-21 and hMSH2 protein expression was given according to the percentage of positive cell in the core. Forty-two out of fifty cores were available for matched analysis of tumor and paired normal tissue. The inventors found that miR-21 was up-regulated in 28 (66%) of these cases when tumor was compared to normal paired tissue. 14 out of 42 (33%) cases had a strong downregulation of hMSH2 in tumor compared to normal tissue. In all these cases miR-21 was found to be up-regulated. Parson correlation analysis in this sub-group of patients showed an r value of −0.82 (p<0.001). Correlation analysis on the entire cohort of cases showed an r value of −0.63. CRC tissues scored positive for both miR-21 and hMSH2 showed no co-expression in the same cancer nest (see FIG. 2A, co-labeling).

Figure 8:
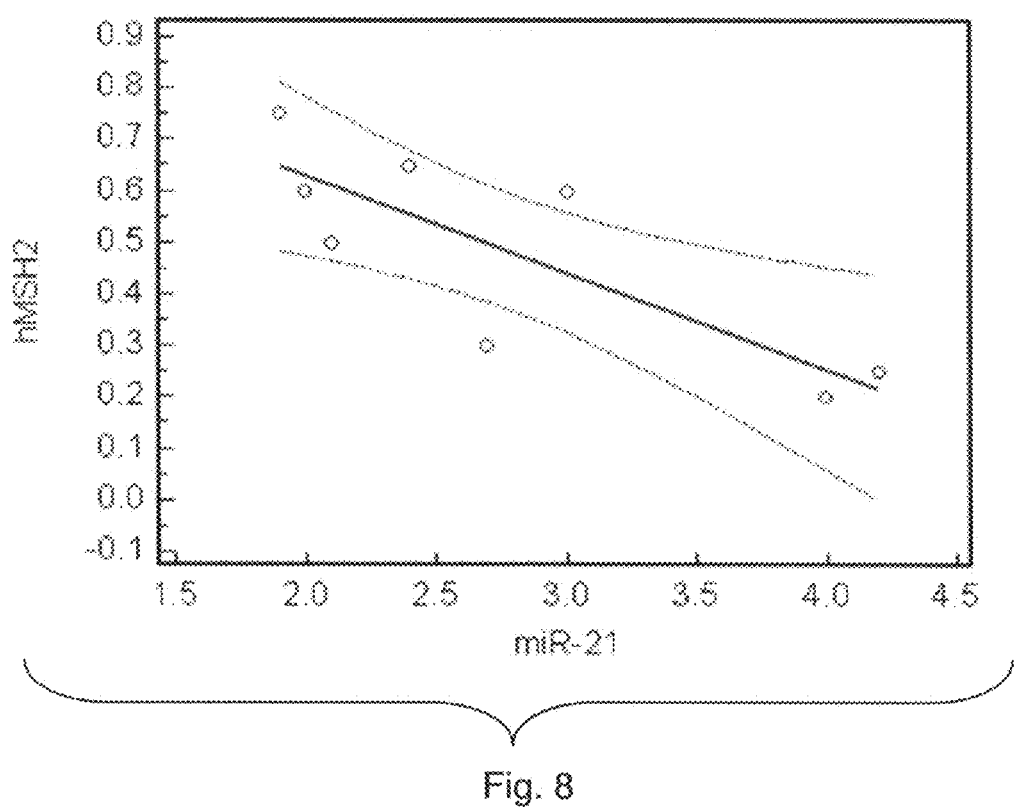

The inventors examined fresh frozen tumors from a second cohort of CRC samples for which cancer and normal adjacent tissues were available (FIG. 2B). miR-21 expression was determined by northern analysis and RT-PCR, while hMSH2 protein expression was determined by western analysis. Twenty-six cases showed hMSH2 down-regulation in tumors compared to normal adjacent tissue. miR-21 expression was found to be increased in 24 of these cases (90%) when tumor was compared to adjacent normal tissues. Since miR-155 can affect the expression of hMSH2 and other MMR proteins, the inventors excluded those cases showing simultaneous over-expression of miR-155 and miR-21 (16 cases) from this analysis. An inverse correlation (r=−0.81 p<0.02) was still evident in remaining 8 cases highlighting the inverse correlation between miR-21 over-expression and hMSH2 down-regulation in CRC tumors (FIG. 2B: FIG. 8).

Example 4 miR-21 Reduces G2/M Arrest and Apoptosis Following Exposure to 5-Fluorouracil

Figure 3A:
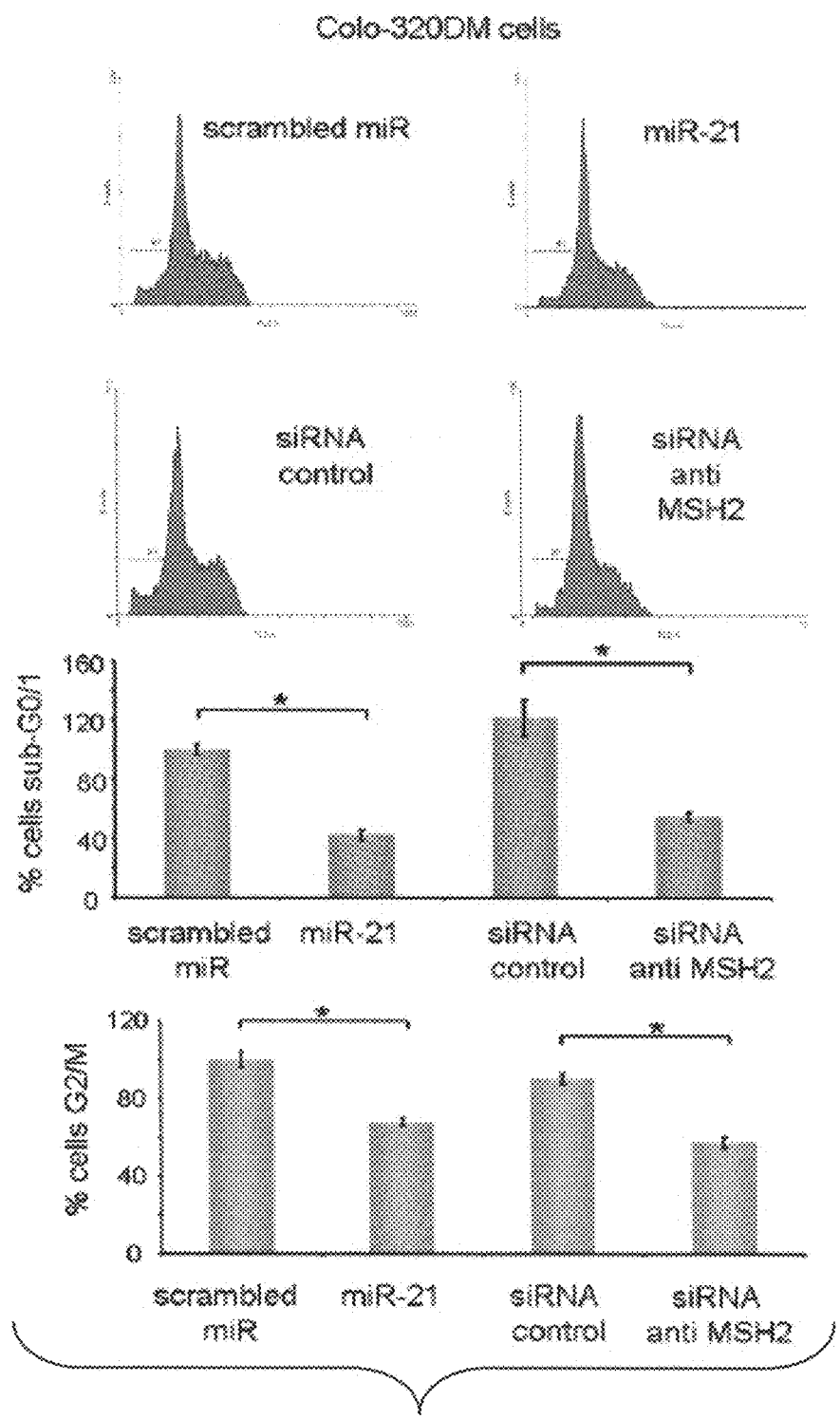
FIGS. 3A-3B. miR-21 inhibits 5-FU induced apoptosis in vitro.
Figure 3B:
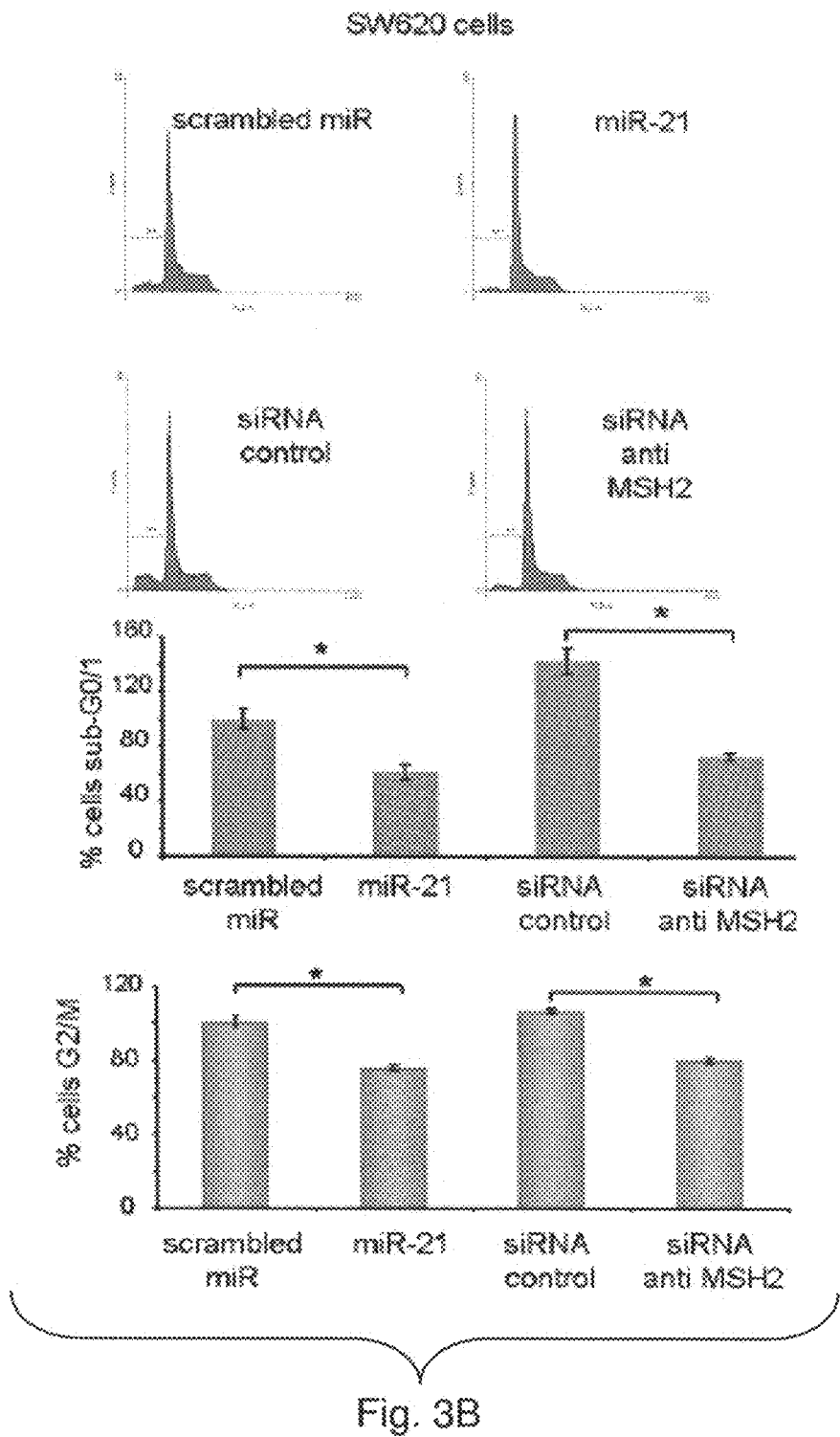
Figure 9:
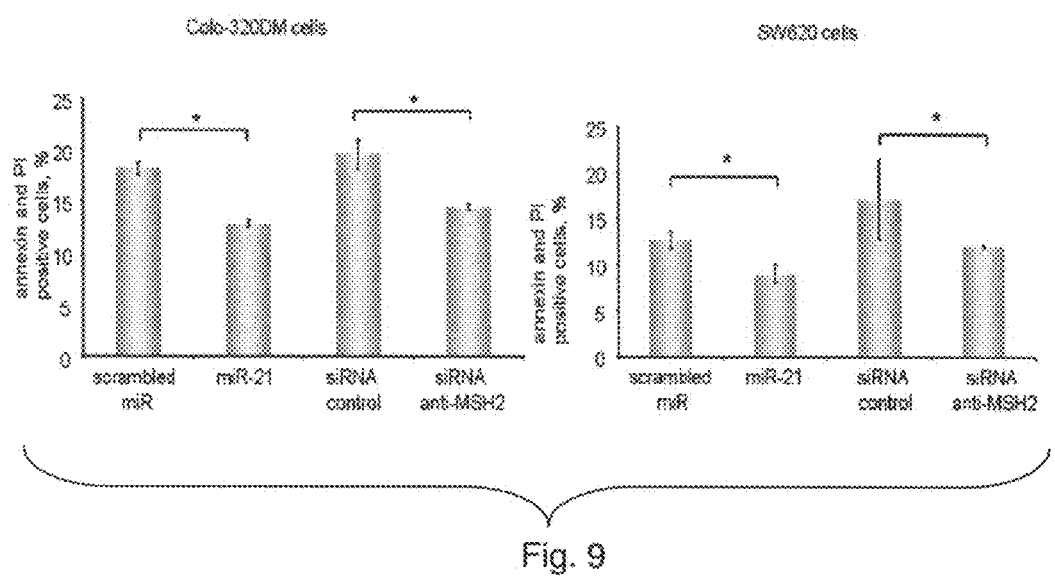

MMR-defective cell lines display resistance to a variety of therapeutic drugs including 5-fluorouracil (5-FU). The present studies have demonstrated that resistance was the result of defective incorporation of 5-FU metabolites into DNA leading to reduced damage-dependent G2/M arrest and subsequent apoptosis. The inventors examined 5-FU induced cell cycle arrest and apoptosis in Colo-320DM and SW620 cells following transfection of miR-21. The inventors used a scrambled miR as a control and compared these results to a similar transfection with a siRNA anti-MSH2 (FIG. 3). The inventors found that miR-21 over-expression decreased the percentage of sub-G1 (apoptosis) and G2/M cells following treatment with 5-FU. miR-21 transfected cells displayed reduced G2/M arrest and apoptosis similar to cells transfected with siRNA to hMSH2 (FIG. 3). The effect of miR-21 expression on 5-FU mediated apoptosis was further confirmed in Colo-320DM and SW620 by Annexin V staining (FIG. 9). A similar response was observed in isogenic Lovo cells where the hMSH2 mutation [Lovo(MSH2−)] has been complemented with the introduction of chromosome 2 [Lovo (MSH2+)] (FIG. 4). miR-21 over-expression, as well as siRNA to hMSH2 reduced sub-G1 and G2/M accumulation in Lovo(MSH2+) cells while no effects were observed in Lovo (MSH2−) cells (FIG. 4). Co-transfection of Lovo(MSH2+) and Lovo(MSH2−) cells with a plasmid encoding the full length hMSH2 cDNA promoted 5-FU induced apoptosis and cell cycle arrest. Co-transfection of the same plasmid along with miR-21 markedly reduced G2/M arrest and apoptosis (FIG. 4). Moreover, deletion of the target site in the hMSH2 cDNA rendered the message insensitive to miR-21 regulation and cells retained a normal damage-induced G2/M arrest and apoptosis. Taken as a whole, the present results are consistent with the conclusion that down-regulation of hMSH2 expression by miR-21 results in cellular resistance to 5-FU.

Example 5

Over-Expression of miR-21 Induces 5-FU Resistance in a Colorectal Cancer Xenograft Model The present cellular studies showed that miR-21 inhibits 5-FU induced G2/M arrest and apoptosis by reducing the expression of hMSH2. The inventors developed a xenograft colon cancer tumor model in which the inventors generated stable clones of Lovo(MSH2+) cells that overexpressed miR-21 [Lovo(MSH2+)-miR-21] or a siRNA to hMSH2 [Lovo(MSH2+)-anti-MSH2] using a lentiviral expression system. Lovo(MSH2−) cells and Lovo(MSH2+) containing the stable insertion

TABLE 1

Statistical analysis of in vivo experiments.

| | week 1 | week 2 | week 3 | week 4 | week 5 | week 6 |
|---|---|---|---|---|---|---|
| Lovo(MSH2+)-miR-21 | 0.136 | 0.008 | 0.026 | 0.040 | 0.048 | 0.035 |
| Lovo(MSH2+)-anti-MSH2 | 0.183 | 0.019 | 0.049 | 0.004 | 0.080 | 0.159 |
| Lovo(MSh2−)-Empty | 0.186 | <0.001 | 0.003 | 0.004 | 0.008 | 0.003 | of an empty vector served as controls. Cells containing stable lentiviral expression were injected in the flank of nude mice (5×106 cells). When xenografts reached a palpable volume, 5-FU (50 mg/kg/day) was administered by intraperitoneal injection for 5 consecutive days per week for 2 weeks. The inventors confirmed that the expression of hMSH2 was dramatically reduced in Lovo(MSH2+) tumor xenografts expressing miR-21 or the anti-MSH2 siRNA compared to the empty vector (FIG. 4A).

The 5-FU treatment proved to be more efficacious with Lovo(MSH2+) tumor xenografts compared to Lovo(MSH2−) tumor xenografts (FIG. 5; Table 1). The present results show that MMR-proficient cells respond better to 5-FU therapy. Importantly, stable over-expression of miR-21 [Lovo(MSH2+)-miR-21] resulted in a reduced response to 5-FU and caused a tumor growth rate comparable to those of Lovo(MSH2+) tumor cells infected with siRNA to hMSH2 [Lovo(MSH2+)-anti-MSH2] (FIG. 5; Table 1). Furthermore, following 5-FU discontinuation (2 weeks) the tumor growth of the Lovo(MSH2+)-miR-21 infected cells appeared significantly greater compared to controls; showing that miR-21 overexpression enhanced cancer progression. Taken together the present results support a central role for miR-21-dependent down-regulation of the hMSH2-hMSH6 heterodimer MMR protein in 5-FU resistance.

P values are shown and have been calculated by comparing each group to the control group (Lovo(MSH2+)-Empty) by using a T-Test analysis.

Example 6

Therapeutic/Prophylactic Methods and Compositions

The invention provides methods of treatment and prophylaxis by administration to a subject an effective amount of a therapeutic antisense miR-21 of the present invention, with or without combination therapy. In a preferred aspect, the therapeutic is substantially purified. The subject is preferably an animal, including but not limited to, animals such as cows, pigs, chickens, etc., and is preferably a mammal, and most preferably human.

Various delivery systems are known and are used to administer a therapeutic of the invention, e.g., encapsulation in liposomes, microparticles, microcapsules, expression by recombinant cells, receptor-mediated endocytosis, construction of a therapeutic nucleic acid as part of a retroviral or other vector, etc. Methods of introduction include, but are not limited to, intradermal, intramuscular, intraperitoneal, intravenous, subcutaneous, intranasal, and oral routes. The compounds are administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. In one embodiment, administration is by direct injection at the site (or former site) of a malignant tumor or neoplastic or pre-neoplastic tissue.

In a specific embodiment where the therapeutic is a nucleic acid encoding a protein therapeutic the nucleic acid is administered in vivo to promote expression of its encoded protein, by constructing it as part of an appropriate nucleic acid expression vector and administering it so that it becomes intracellular, or coating with lipids or cell-surface receptors or transfecting agents, or by administering it in linkage to a homeobox-like peptide which is known to enter the nucleus. Alternatively, a nucleic acid therapeutic can be introduced intracellularly and incorporated within host cell DNA for expression, by homologous recombination.

The present invention also provides pharmaceutical compositions. Such compositions comprise a therapeutically effective amount of a therapeutic, and a pharmaceutically acceptable carrier or excipient. Such a carrier includes, but is not limited to, saline, buffered saline, dextrose, water, glycerol, ethanol, and combinations thereof. The carrier and composition can be sterile. The formulation will suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition also includes a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it is be dispensed with an infusion bottle containing sterile pharmaceutical grade water or saline. Where the composition is administered by injection, an ampoule of sterile water for injection or saline is provided so that the ingredients are mixed prior to administration.

The therapeutics of the invention are formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic of the invention which will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation will also depend on the route of administration, and the seriousness of the disease or disorder, and is decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

Example 7

Method of Treating Cancer Patients

This example describes a method of selecting and treating patients that are likely to have a favorable response to treatments with compositions herein.

A patient diagnosed with cancer ordinarily first undergoes tissue resection with an intent to cure. Tumor samples are obtained from the portion of the tissue removed from the patient. RNA is then isolated from the tissue samples using any appropriate method for extraction of small RNAs that are well known in the art, such as by using TRIZOL™. Purified RNA is then subjected to RT-PCR using primers specific miR21 or other differentially expressed miRNAs disclosed, optionally in conjunction with genetic analysis. These assays are run to determine the expression level of the pertinent RNA in the tumor. If differentially expressed miR expression pattern is determined, especially if mutant status is ascertained, the patient is a candidate for treatment with the compositions herein.

Accordingly, the patient is treated with a therapeutically effective amount of the compositions according to methods known in the art. The dose and dosing regimen of the compositions will vary depending on a variety of factors, such as health status of the patient and the stage of the cancer. Typically, treatment is administered in many doses over time.

Example 8

Methods of Diagnosing Cancer Patients

In one particular aspect, there is provided herein a method of diagnosing whether a subject has, or is at risk for developing, cancer. The method generally includes measuring the differential miR expression pattern of the miR-21 and/or MMR protein expression compared to control. If a differential miR/MMR protein expression pattern is ascertained, the results are indicative of the subject either having, or being at risk for developing, colorectal cancer. In certain embodiments, the level of the at least one gene product is measured using Northern blot analysis. Also, in certain embodiments, the level of the at least one gene product in the test sample is less than the level of the corresponding miR gene product and/or MMR protein expression in the control sample, and/or the level of the at least one miR gene product and/or MMR protein expression in the test sample is greater than the level of the corresponding miR gene product and/or MMR protein expression in the control sample.

Example 9

Measuring miR Gene Products

The level of the at least one miR gene product can be measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, colorectal cancer.

Example 10

Diagnostic and Therapeutic Applications

In another aspect, there is provided herein are methods of treating a cancer in a subject, where the signal of at least one miRNA, relative to the signal generated from the control sample, is de-regulated (e.g., down-regulated and/or up-regulated).

Also provided herein are methods of diagnosing whether a subject has, or is at risk for developing, a cancer associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

Example 11

Kits

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of the sequences herein.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container means. The kits may also include components that facilitate isolation of the labeled miRNA. It may also include components that preserve or maintain the miRNA or that protect against its degradation. The components may be RNAse-free or protect against RNAses.

Also, the kits can generally comprise, in suitable means, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated by the inventors herein. The kits can include an miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Example 12

Array Preparation and Screening

Also provided herein are the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Microarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample.

A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g. covalent or non-covalent, and the like. The labeling and screening methods described herein and the arrays are not limited in its utility with respect to any parameter except that the probes detect miRNA; consequently, methods and compositions may be used with a variety of different types of miRNA arrays.

In view of the many possible embodiments to which the principles of the inventors' invention may be applied, it should be recognized that the illustrated embodiments are only preferred examples of the invention and should not be taken as a limitation on the scope of the invention. Rather, the scope of the invention is defined by the following claims. The inventors therefore claim as the inventors' invention all that comes within the scope and spirit of these claims.

What is claimed is:

1. A method of modulating hMSH2 protein expression in tumor cells of a subject, wherein the subject has been diagnosed with colorectal cancer (CRC), the method comprising:
   administering a pharmaceutical composition of an effective amount of antisense miR-21; and
   increasing hMSH2 protein expression.

2. A method to treat a patient with colorectal cancer, comprising:
   identifying a patient with colorectal cancer having decreased hMSH2 expression;
   administering a pharmaceutical composition of an effective amount of antisense miR-21 to the patient having decreased hMSH2 expression, thereby increasing hMSH2 expression; and
   thereafter, administering a pyrimidine analog.

3. The method of claim 2, wherein the pyrimidine analog is 5-fluorouracil.

4. The method of claim 2, wherein the antisense miR-21 further comprises a locked nucleic acid (LNA).

5. The method of claim 2, wherein the patient has at least one condition selected from the group consisting of: primary pyrimidine analog-resistant colorectal cancer, acquired pyrimidine analog-resistant colorectal cancer, defective mismatch repair proteins, stage II colorectal cancer, and stage III colorectal cancer.

6. A method of reducing tumor volume in a subject, wherein the tumor comprises at least one tumor cell having decreased hMSH2 expression compared to a control, the method comprising:
   administering a pharmaceutical composition of an effective amount of antisense miR-21 to the subject, thereby increasing hMSH2 expression; and
   administering a pyrimidine analog to the subject.

7. The method of claim 6, wherein the tumor is a colorectal tumor.

8. The method of claim 6, which results in increased apoptosis of the tumor cell.

9. The method of claim 6, wherein the hMSH2 expression is increased.

10. The method of claim 6, wherein the pyrimidine analog is 5-flurouracil.

* * * * *